(12) United States Patent
Malcolmson et al.

(10) Patent No.: US 9,687,834 B2
(45) Date of Patent: *Jun. 27, 2017

(54) CATALYSTS FOR METATHESIS REACTIONS INCLUDING ENANTIOSELECTIVE OLEFIN METATHESIS, AND RELATED METHODS

(75) Inventors: Steven J. Malcolmson, Brighton, MA (US); Amir H. Hoveyda, Lincoln, MA (US); Simon J. Meek, Newtonville, MA (US); Richard R. Schrock, Winchester, MA (US)

(73) Assignees: Trustees of Boston College, Chestnut Hill, MA (US); Massachusetts Institute of Technology, Cambridge, MA (US)

(*) Notice: Subject to any disclaimer, the term of this patent is extended or adjusted under 35 U.S.C. 154(b) by 1245 days.

This patent is subject to a terminal disclaimer.

(21) Appl. No.: 12/864,261

(22) PCT Filed: Jan. 23, 2009

(86) PCT No.: PCT/US2009/000465
§ 371 (c)(1),
(2), (4) Date: Oct. 12, 2010

(87) PCT Pub. No.: WO2009/094201
PCT Pub. Date: Jul. 30, 2009

(65) Prior Publication Data
US 2011/0065915 A1 Mar. 17, 2011

Related U.S. Application Data

(60) Provisional application No. 61/062,322, filed on Jan. 25, 2008.

(51) Int. Cl.
| | | |
|---|---|---|
| *C07D 487/18* | (2006.01) | |
| *C07D 211/02* | (2006.01) | |
| *C07D 233/04* | (2006.01) | |
| *C07D 487/04* | (2006.01) | |
| *C07D 471/04* | (2006.01) | |
| *C07F 7/18* | (2006.01) | |
| *C07D 309/18* | (2006.01) | |
| *C07D 309/20* | (2006.01) | |
| *B01J 31/12* | (2006.01) | |
| *B01J 31/18* | (2006.01) | |
| *B01J 31/22* | (2006.01) | |
| *C07F 11/00* | (2006.01) | |

(52) U.S. Cl.
CPC ........ *B01J 31/1805* (2013.01); *B01J 31/181* (2013.01); *B01J 31/2208* (2013.01); *B01J 31/2265* (2013.01); *C07F 11/005* (2013.01); *B01J 2231/54* (2013.01); *B01J 2531/64* (2013.01); *B01J 2531/66* (2013.01)

(58) Field of Classification Search
None
See application file for complete search history.

(56) References Cited

U.S. PATENT DOCUMENTS

| | | |
|---|---|---|
| 5,055,628 A | 10/1991 | Lin et al. |
| 5,889,128 A | 3/1999 | Schrock et al. |
| 6,121,473 A | 9/2000 | Schrock et al. |
| 6,271,325 B1 | 8/2001 | McConville et al. |
| 6,316,555 B1 | 11/2001 | Schrock et al. |
| 6,346,652 B1 | 2/2002 | Schrock et al. |
| 6,610,806 B2 | 8/2003 | Schrock et al. |
| 6,855,839 B2 | 2/2005 | McConville et al. |
| 6,939,982 B2 * | 9/2005 | Hoveyda et al. ............... 556/21 |
| 7,135,544 B2 | 11/2006 | Schrock et al. |
| 7,932,397 B2 * | 4/2011 | Hock et al. ................... 548/101 |
| 2008/0119678 A1 | 5/2008 | Hock et al. |

OTHER PUBLICATIONS

Cooksey et al., Org. Biomol. Chem, 2004, 2, 1719-1731.*
[No Author Listed] New catalysts promise faster, cleaner, and more efficient research platform. Science Daily. Nov. 16, 2008. 2 pages.
Aeilts et al., A readily available and user-friendly chrial catalyst for efficient enantioselective olefin metathesis. Angew Chem Int Ed. 2001;40(8):1452-6.
Agbossou et al., Synthesis and Reactivity of Chiral Rhenium Alcohol Complexes of the Formula [($\eta^5$-$C_5H_5$)Re(NO)(PPh$_3$)(ROH)]⊕ BF$_4$⊖. Chem Berichte. 1990;123(6):1293-9.
Al Obaidi et al., Steric and electronic effects on the chemistry of molybdenum octahedrally co-ordinated by six nitrogen atoms. The molecular structure of [Mo{HB(3,5-Me$_2$C$_3$N$_2$H)$_3$}(NO)(pyrollide)$_2$]. J Chem Soc Chem Commun. 1984;(11): 690-2.
Anderson et al., Kinetic selectivity of olefin metathesis catalysts bearing cyclic (alkyl)(amino)carbenes. Organometallics. 2008;27(4):563-6.
Ascenso et al., Synthesis and characterization of [W(NC$_4$Me$_4$)$_2$Cl$_2$] and [W(NC$_4$Me$_4$)$_2$(CH$_3$)$_2$], the first azametallocene tungsten complexes with pyrrolyl ligands. Electronic structure and bonding of tungsten bispyrrolyl complexes. Inorg Chem Acta. 2003; 356: 249-58.
Bailey et al., Evaluation of molybdenum and tungsten metathesis catalysts for homogeneous tandem alkane metathesisorganometallics. 2009;28(1):355-60.
Bazan et al., Living ring-opening metathesis polymerization of 2,3-difunctionalized 7-oxanorbornenes and 7-oxanorbornadienes by Mo(CHCMe2R)(NC6H3-iso-Pr2-2,6)(O-tert-Bu)2 and Mo(CHCMe2R)(NC6H3-iso-Pr2-2,6)(OCMe2CF3)2. J Am Chem Soc. 1991;113(18):6899-907.
Bei et al., Highly efficient olefin-metathesis catalysts. Pharm Technol. 2008:s18.
Blackwell et al., Enediynes via sequential acetylide reductive coupling and alkyne metathesis: Easy access to well-defined molybdenum initiators for alkyne metathesis. Organometallics. 2003;22: 3351-53.
Blackwell et al., New approaches to olefin cross-metathesis. J Am Chem Soc. 2000;122:58-71.

(Continued)

*Primary Examiner* — Matthew Coughlin
*Assistant Examiner* — Po-Chih Chen
(74) *Attorney, Agent, or Firm* — Stoel Rives LLP

(57) ABSTRACT

The present invention provides compositions comprising metal complexes, and related methods. In some embodiments, metal complexes of the invention may be useful as catalysts for chemical reactions, including metathesis reactions, wherein the catalysts exhibit enhanced activity and stereoselectivity. In some embodiments, the invention may advantageously provide metal complexes comprising a stereogenic metal atom. Such metal complexes may be useful in enantioselective catalysis.

16 Claims, 34 Drawing Sheets

(56) References Cited

OTHER PUBLICATIONS

Blanc et al., Dramatic improvements of well-defined silica supported mo-based olefin metathesis catalysts by tuning the n-containing ligands. J Am Chem Soc. 2007;129(27):8434-5.
Blanc et al., Highly active, stable, and selective well-defined silica supported mo imido olefin metathesis catalysts. J Am Chem Soc. 2007; 129(17):1044-1045.
Blanc et al., Surface versus molecular siloxy ligands in well-defined olefin metathesis catalysis: [{(RO)$_3$SiO}Mo(=NAr)(=CH$t$Bu)(CH$_2t$Bu)]. Angew Chem Int Ed. 2006;45:1216-20.
Bornand et al., Mechanism-based design of a ROMP catalyst for sequence-selective copolymerization. Angew Chem Int Ed Engl. Dec. 9, 2005;44(48):7909-11.
Brunner et al., Catalytic hydrosilylation or hydrogenation at one coordination site of [Cp'Fe(CO)(X)] fragments. Angewandte Chemie Intl Ed Engl. Oct. 1990;29(10):1131-2.
Brunner et al., Optisch aktive Übergangsmetall-Komplexe, LI: P-Liganden als optisch aktive Hilfsstoffe in den Komplexen C5H5M(CO)(NO)L, M=Cr, Mo, W. Chem Ber. 1978;111:673-91.
Brunner, Optical activity at an asymmetrical manganese atom. Angew Chem, Int Ed Engl. 1969;8:382-3.
Brunner, Optically active organometallic compounds of transition elements with chiral metal atoms. Angew Chemie Intl Ed. May 3, 1999;38(9):1194-1208.
Brunner, Stability of the metal configuration in chiral-at-metal half-sandwich compounds. Eur J Inorg Chem. 2001:905-12.
Burdett et al., Renewable monomer feedstocks via olefin metathesis: fundamental mechanistic studies of methyl oleate ethenolysis with the first-generation grubbs catalyst. Organometallics. 2004;23(9):2027-47.
Cantrell et al., Ring-opening Metathesis of a cyclic imine. Organometallics. Aug. 2, 2000;19(18):3562-68.
Chatterjee et al., Olefin Cross-Metathesis. Handbook Metathesis. 2003;2:246-95.
Connon et al., Recent developments in olefin cross-metathesis. Angew Chem Int Ed Engl. Apr. 29, 2003;42(17):1900-23.
Corma et al., Chemical routes for the transformation of biomass into chemicals. Chem Rev. Jun. 2007;107(6):2411-502. Epub May 30, 2007.
Dias et al., Synthesis, characterisation, crystal structure, reactivity and bonding in titanium complexes containing 2,3,4,5-tetramethylpyrrolyl. J Chem Soc, Dalton Trans. 1997;1055-61.
Dinger et al., High turnover numbers with ruthenium-based metathesis catalysts. Adv Synth Catal. Aug. 2002;344(6-7):671-7.
Dolman et al., Efficient catalytic enantioselective synthesis of unsaturated amines: preparation of small- and medium-ring cyclic amines through mo-catalyzed asymmetric ring-closing metathesis in the absence of solvent. J Am Chem Soc. Jun. 19, 2002;124(24):6991-7.
Dolman, New chiral molybdenum metathesis catalysts; application of the enantioselective preparation of cyclic amines. Ph.D. Thesis. MIT. Jun. 2004. 234 pages.
Duarte et al., Chlorobis(dimethylamido)($\eta^5$-2,5-dimethylpyrrolyl)titanium(IV), [Ti(NMe$_2$)$_2$(DMP)Cl]. Acta Cryst. 2005;C61:m104-6.
Feldman et al., Recent advances in the chemistry of "d$^0$" alkylidine metallacyclobutane complexes. Prog Inorg Chem. 1991;39:1-74.
Flook et al., Z-selective olefin metathesis processes catalyzed by a molybdenum hexaisopropylterphenoxide monopyrrolide complex. J Am Chem Soc. Jun. 17, 2009;131(23):7962-3.
Fontecave et al., Chiral-at-metal complexes as asymmetric catalysts. In Chiral Diazaligands for Asymmetric Synthesis. Top Organometallic Chem. 2005;15(2005):271-88.
Forman et al., A stable ruthenium catalyst for productive olefin metathesis. Organometallics. 2004;23(21):4824-7.
Fürstner et al., Alkyne metathesis: Development of a novel molybdenum-based catalyst system and its application to the total synthesis of epothilone A and C. Chem Eur J. 2001;7(24):5299-5317.
Fürstner et al., Mo[N($t$-Bu)(Ar)]$_3$ complexes as catalyst precursors: in situ activation and application to metathesis reactions of alkynes and diynes. J Am Chem Soc. 1999;121(40):9453-54.
Furstner et al., Cationic ruthenium allenylidene complexes as catalysts for ring closing olefin metathesis. Chemistry. May 15, 2000;6(10):1847-57.
Ganter, Chiral organometallic half-sandwich complexes with defined metal configuration. Chem Soc Rev. May 2003;32(3):130-8.
Giessert et al., Intermolecular enol ether-alkyne metathesis. Org Lett. May 15, 2003;5(10):1793-6.
Gillingham et al., Chiral N-heterocyclic carbenes in natural product synthesis: application of Ru-catalyzed asymmetric ring-opening/cross-metathesis and Cu-catalyzed allylic alkylation to total synthesis of baconipyrone C. Angew Chem Int Ed Engl. 2007;46(21):3860-4.
Giudici et al., Directed catalytic asymmetric olefin metathesis. Selectivity control by enoate and ynoate groups in Ru-catalyzed asymmetric ring-opening/cross-metathesis. J Am Chem Soc. Apr. 4, 2007;129(13):3824-5. Epub Mar. 8, 2007.
Hadlington et al., Catalyst flexes for extra control. Chemistry World. Nov. 17, 2008. Last accessed online. Dec. 1, 2008.
Hesek et al., The first asymmetric synthesis of chiral ruthenium tris(bipyridine) from racemic ruthenium bis(bipyridine) complexes. Tetrahedron Lett. Apr. 8, 2000;41(15):2617-20.
Hock et al., Dipyrrolyl precursors to bisalkoxide molybdenum olefin metathesis catalysts. J Am Chem Soc. 2006:128(50):16373-5.
Ibrahem et al., Highly Z- and enantioselective ring-opening/cross-metathesis reactions catalyzed by stereogenic-at-Mo adamantylimido complexes. J Am Chem Soc. Mar. 25, 2009;131(11):3844-5.
Jiang et al., Fundamental studies of tungsten alkylidene imido monoalkoxidepyrrolide complexes. J Am Chem Soc. Jun. 10, 2009;131(22):7770-80.
Jiang et al., Highly Z-selective metathesis homocoupling of terminal olefins. J Am Chem Soc. Nov. 25, 2009;131(46):16630-1.
Kershner et al., $\eta^5$-Heterocyclic metal carbonyls. Coord Chem Rev. 1987;79(1987):279-92.
Kiely et al., Enantioselective synthesis of medium-ring heterocycles, tertiary ethers, and tertiary alcohols by Mo-catalyzed ring-closing metathesis. J Am Chem Soc. Mar. 27, 2002;124(12):2868-9.
Knof et al., Predetermined chirality at metal centers. Angew Chemie Intl Ed. Feb. 1, 1999;38(3):302-22.
Kreickmann et al., Imido alkylidene bispyrrolyl complexes of tungsten. Organometallics. 2007;26: 5702-11.
Lacour et al., Recent developments in chiral anion mediated asymmetric chemistry. Chem Soc Rev. Nov. 2003;32(6):373-82.
Lee et al., Enantioselective synthesis of cyclic enol ethers and all-carbon quaternary stereogenic centers through catalytic asymmetric ring-closing metathesis. J Am Chem Soc. Apr. 19, 2006;128(15):5153-7.
Lee et al., Endo-selective enyne ring-closing metathesis promoted by stereogenic-at-Mo monoalkoxide and monoaryloxide complexes. Efficient synthesis of cyclic dienes not accessible through reactions with Ru carbenes. J Am Chem Soc. Aug. 5, 2009;131(30):10652-61.
Liu et al., Regioselective ring-opening/cross-metathesis reactions of norbornene derivatives with electron-rich olefins. Org Lett. Jan. 6, 2005;7(1):131-3.
Lokare et al., Synthesis, properties, and structure of tethered molybdenum alkylidenes. Organometallics. 2008;27(19):5130-8.
Malcolmson et al., Highly efficient molybdenum-based catalysts for enantioselective alkene metathesis. Nature. Dec. 18, 2008;456(7224):933-7. Epub Nov. 16, 2008.
Marinescu et al., Ethenolysis reactions catalyzed by imido alkylidene monoaryloxide monopyrrolide (MAP) complexes of molybdenum. J Am Chem Soc. Aug. 12, 2009;131(31):10840-1.
Marinescu et al., Inversion of configuration at the metal in diastereomeric imido alkylidene monoaryloxide monopyrrolide complexes of molybdenum. J Am Chem Soc. Jan. 14, 2009;131(1):58-9.
Maruoka et al., Efficient synthesis of sterically hindered chiral binaphthol derivatives. Bull Chem Soc Jpn. 1988;61(8):2975-6.

(56) References Cited

OTHER PUBLICATIONS

McDougal et al., Asymmetric Morita-Baylis-Hillman reactions catalyzed by chiral Brønsted acids. J Am Chem Soc. Oct. 8, 2003;125(40):12094-5.

McDougal et al., The development of the asymmetric morita-baylis-hillman reaction catalyzed by chiral brønsted acids. Adv Synth Cat. 2004;346:1231-40.

Meek et al., The significance of degenerate processes to enantioselective olefin metathesis reactions promoted by stereogenic-at-Mo complexes. J Am Chem Soc. Nov. 18, 2009;131(45):16407-9.

Monchaud et al., Ion-pair-mediated asymmetric synthesis of a configurationally stable mononuclear tris(diimine)-iron(II) complex. Angew Chem Int Ed Engl. Jul. 2, 2002;41(13):2317-9.

Nicolaou et al., Metathesis reactions in total synthesis. Angew Chem Int Ed Engl. Jul. 18, 2005;44(29):4490-527.

Pezet et al., Highly diastereoselective preparation of ruthenium bis(diimine) sulfoxide complexes: new concept in the preparation of optically active octahedral ruthenium complexes. Organometallics. 2000;19(20):4008-15.

Poater et al., Understanding d(0)-olefin metathesis catalysts: which metal, which ligands? J Am Chem Soc. Jul. 4, 2007;129(26):8207-16. Epub Jun. 9, 2007.

Rhers et al., A well-defined, silica-supported tungsten imido alkylidene olefin metathesis catalyst. Organometallics. 2006;25(15):3554-7.

Sattely et al., Design and stereoselective preparation of a new class of chiral olefin metathesis catalysts and application to enantioselective synthesis of quebrachamine: catalyst development inspired by natural product synthesis. J Am Chem Soc. Jan. 28, 2009;131(3):943-53.

Sattely et al., Enantioselective synthesis of cyclic amides and amines through mo-catalyzed asymmetric ring-closing metathesis. J Am Chem Soc. Jun. 15, 2005;127(23):8526-33.

Sattely, Cyclic amines and amides through molybdenum-catalyzed asymmetric olefin metathesis: A total synthesis of quebrachamine. Jan. 1, 2007. Boston College Dissertations and Theses. Paper AAI3256831. http://escholarship.bc.edu/dissertations/AAI3256831. 340 pages.

Schrock et al., Further studies of imido alkylidene complexes of tungsten, well-characterized olefin metathesis catalysts with controllable activity. Organometallics. Aug. 1990;9(8):2262-75.

Schrock et al., Molybdenum alkylidyne complexes that contain 3,3'-di-$t$-butyl-5,5', 6,6'-tetramethyl-1, 1'-biphenyl-2,2'-diolate ([Biphen]$^2$) ligand. J Organomet Chem. 2003;684:56-67.

Schrock et al., Molybdenum and tungsten imido alkylidene complexes as efficient olefin-metathesis catalysts. Angew Chem Int Ed Engl. 2003;42(38):4592-33.

Schrock et al., Preparation of molybdenum and tungsten neopentylidyne complexes of the type $M(CCMe_3)(O_2CR)_3$, their reactions with acetylenes, and the X-ray structure of the $\eta^3$-cyclopropenyl complex $W[C_3(CMe_3)Et_2]O_2CCH_3)_3^1$. Organometallics. 1986;5:25-33.

Schrock et al., Synthesis of molybdenum imido alkylidene complexes and some reactions involving acyclic olefins. J Am Chem Soc. 1990;112:3875-86.

Schrock et al., Thousands of catalysts for olefin metathesis: variability, longevity and asymmetry at the metal. Abstract. Presented Oct. 24, 2008 at Technical University of Berlin.

Schrock, High oxidation state multiple metal-carbon bonds. Chem Rev. 2002;102:145-79.

Schrock, Recent advances in high oxidation state mo and w imido alkylidene chemistry. Chem Rev. 2009;109(8):3211-26.

Schrodi et al., Ruthenium olefin metathesis catalysts for the ethenolysis of renewable feedstocks. Clean: Soil, Air, Water. 2008;36:669-673.

Singh et al., Molybdenum imido alkylidene metathesis catalysts that contain electron-withdrawing biphenolates or binaphtholates. Organometallics. 2007;26(10):2528-39.

Singh et al., Synthesis of monoalkoxide monopyrrolyl complexes $Mo(NR)(CHR')(OR'')$(pyrrolyl): enyne metathesis with high oxidation state catalysts. J Am Chem Soc. Oct. 24, 2007;129(42):12654-5. Epub Sep. 29, 2007.

Sinha et al., Diphenylamido precursors to bisalkoxide molybdenum olefin catalysts. Organometallics. 2006;25(19):4621-6.

Sinha et al., Reactions of $M(N-2,6-i-Pr_2C_6H_3)(CHR)(CH_2R')_2$ (M=Mo, W) complexes with alcohols to give olefin metathesis catalysts of the type $M(N-2,6-i-Pr_2C_6H_3)(CHR)(CH_2R')(OR'')$. Organometallics. 2006;25:1412-23.

Solans-Monfort et al., $d^0$ Re-based olefin metathesis catalysts, $Re(\equiv CR)(=CHR)(X)(Y)$: The key role of X and Y ligands for efficient active sites. J Am Chem Soc. 2005;127(40):14015-25.

Takano et al., Enantioselective route to both (+)- and (−)-enantiomers of quebrachamine using a single chiral synthon. J Chem Soc Chem Commun. 1981:1153-5.

Takemura et al., Stereochemical aspects of asymmetric Diels-Alder reaction catalyzed by chiral alkoxyaluminum dichlorides. Tetrahedron Lett. 1987;28(46):5687-90.

Tallarico et al., Selectivity in ring-opening metatheses. Tetrahedron. Dec. 1, 1997;53(48):16511-20.

Tayama et al., Activation of ether functionality of allyl vinyl ethers by chiral bis(organoaluminum) Lewis acids: application to asymmetric Claisen rearrangement. Tetrahedron. Oct. 7, 2002;58(41):8307-12.

Tonzetich et al., Reaction of phosphoranes with $Mo(N-2,6-i-Pr_2C_6H_3)(CHCMe_3)[OCMe(CF_3)_2]_2$: Synthesis and reactivity of an anionic imido alkylidyne complex. Organometallics. 2006;25:4301-6.

Tsai et al, Facile synthesis of trialkoxymolybdenum(VI) alkylidyne complexes for alkyne metathesis. Organometallics. 2000;19:5260-62.

Van Veldhuizen et al., A readily available chiral Ag-based N-heterocyclic carbene complex for use in efficient and highly enantioselective Ru-catalyzed olefin metathesis and Cu-catalyzed allylic alkylation reactions. J Am Chem Soc. May 11, 2005;127(18):6877-82.

Van Veldhuizen et al., A recyclable chiral Ru catalyst for enantioselective olefin metathesis. Efficient catalytic asymmetric ring-opening/cross metathesis in air. J Am Chem Soc. May 8, 2002;124(18):4954-5. Erratum in: J Am Chem Soc. Oct. 15, 2003;125(41):12666.

Walls et al., Alkaloids from stemmadenia species-I : The alkaloids of S. Donnell-Smithii and S. Galeottiana. Tetrahedron. May 1958;2(3-4):173-82.

Weatherhead et al., Mo-catalyzed asymmetric olefin metathesis in target-oriented synthesis: enantioselective synthesis of (+)-africanol. Proc Natl Acad Sci U S A. Apr. 20, 2004;101(16):5805-9. Epub Mar. 31, 2004.

Werner et al., Bur Kennfnie dee asymmetrimhen Kobaltatoms. I. Ber Dtsch Chem Ges. 1911;44:1887-98. German.

Yashiro et al., Efficient stereochemical regulation of octahedral cobalt(III) complexes by a chiral bidentate ligand. Part 2. Remarkable effect of the chelate-ring size in the stereoselective formation of sym-cis-(ethylenediamine-N,N'-diacetato)(pentane-2,4-diamine)cobalt(III). J Chem Soc. Dalton Trans. 1994;10:1511-6.

Yashiro et al., Efficient stereochemical regulation of octahedral cobalt(III) complexes by a chiral bidentate ligand. Part 1. Effect of N-alkyl substitutions. J Chem Soc, Dalton Trans. 1994;7:1073-7.

Yi et al., The ruthenium acetylide catalyzed cross-coupling reaction of terminal and internal alkynes: isolation of a catalytically active β-agostic intermediate species. Organometallics. 1998;17(15):3158-60.

Zhang et al., A reductive recycle strategy for the facile synthesis of molybdenum(VI) alkylidyne catalysts for alkyne metathesis. Chem Commun. 2003:832-3.

Zhou et al., Synthesis and reactivity of chiral rhenium indenyl complexes of the formula $[(\eta^5-C_9H_7)Re(NO)(PPh3)(X)]n+$. Organometallics. 1993;12(10):3918-23.

Zhu et al., Chiral Mo-Binol complexes: activity, synthesis, and structure. efficient enantioselective six-membered ring synthesis through catalytic metathesis. J Am Chem Soc. 1999;121:8251-9.

(56) References Cited

OTHER PUBLICATIONS

International Preliminary Report on Patentability from International Patent Application Serial No. PCT/US2007/024318, filed Nov. 21, 2007, mailed May 26, 2009.
International Search Report and Written Opinion in PCT/US2007/024318, issued on May 7, 2008.
International Preliminary Report on Patentability in connection with Application Serial No. PCT/US2009/000465 issued Jul. 27, 2010.
International Search Report and Written Opinion in connection with Application Serial No. PCT/US2009/000465 mailed Jul. 13, 2009.
Invitation to Pay Additional Fees in connection with Application Serial No. PCT/US2009/000465 mailed May 11, 2009.
Wampler et al., Synthesis of Molybdenum Imido Alkylidene Complexes that Contain Siloxides, Organometallics, 26: 6674-6680 (2007).
Wampler, Synthesis Investigations of Molybdenum Pyrrolide and Related Complexes, Massachusetts Institute of Technology: 1-260 (2010).

\* cited by examiner

37a: 22 °C, >98% conv, single diastereomer
37b: 60 °C, <2% conv

CATALYSTS FOR METATHESIS REACTIONS INCLUDING ENANTIOSELECTIVE OLEFIN METATHESIS, AND RELATED METHODS

RELATED APPLICATIONS

The present application is a national stage filing under 35 U.S.C. §371 of international PCT application, PCT/US2009/00465, filed Jan. 23, 2009, which claims priority under 35 U.S.C. §119(e) to U.S. provisional application, U.S. Ser. No. 61/062,322, filed Jan. 25, 2008.

STATEMENT REGARDING FEDERALLY SPONSORED RESEARCH OR DEVELOPMENT

This invention was made with government support under grant number R01 GM059426 awarded by the National Institutes of Health. The government has certain rights in this invention.

FIELD OF THE INVENTION

The present invention generally relates to compositions useful as organometallic catalysts, and related methods.

BACKGROUND OF THE INVENTION

The selective synthesis of stereogenic metal centers is less developed than carbon stereogenic centers. The first synthesis of a stereogenic metal complex, 1, was accomplished in 1911. As shown in FIG. 1, complex 1 is chiral due to the arrangement of the two bidentate ethylenediamine ligands; the complex is prepared as a racemic mixture and the enantiomers separated by classical resolution.

Other complexes comprising a stereogenic metal center have also been stereoselectively synthesized using chiral polydentate ligands, sometimes in conjunction with at least one achiral ligand. One such example is complex 2, shown in FIG. 1. A class of Ru-based olefin metathesis catalysts containing a stereogenic metal center and synthesized using a chiral bidentate ligand has been reported, including structures 3 and 4 shown in FIG. 1. Using this method, a single diastereomer can be isolated in high yield. In some cases, a preference for the formation of a particular diastereomer can be attributed to steric factors.

Additionally, there are a number of stereogenic-at-metal complexes bearing achiral polydentate ligands, where stereochemistry at the metal center can be partially controlled by means of a chiral monodentate ligand. For example, FIG. 2 shows the transformation of a racemic Ru complex 5 to complex 6 through a dynamic enantioselective process upon reaction with an enantiopure sulfoxide. The reaction proceeded in high yield and with modest diastereoselectivity (74% d.e.). It has also been shown that the chloride and sulfoxide ligands of complexes such as 6 may be displaced by an additional bipyridyl ligand with retention of configuration, thus generating an enantioenriched chiral complex bearing only achiral ligands.

Although less common, the stereoselective self-assembly of achiral polydentate ligands about a metal center has also been controlled by means of a chiral counterion. For example, an octahedral Fe complex has been synthesized, bearing a bidentate and a tetradentate ligand, with high selectivity (>20:1 d.r.) by means of a P stereogenic phosphate counterion (trisphat).

Examples of stereogenic metal complexes, bearing all monodentate ligands, however, are rare, and generally have been prepared only in racemic form. FIG. 3 shows examples of such metal complexes. One of the challenges faced when preparing enantiopure stereogenic metal complexes with all monodentate ligands is the lability of many of these ligands, leading to racemization of the complex. In addition, the complexes often require a separate purification step in order to separate the enantiomers and/or diastereomers. Re complex 7, shown in FIG. 4, is a "piano stool" complex, which is stereogenic at the metal (but racemic) and carries all monodentate ligands. One of the ligands in the complex is an alkoxide. As shown by the synthesis in FIG. 4, this complex may be reacted with $HBF_4 \cdot OEt_2$ to generate cationic complex 8, which contains a datively-bound alcohol ligand; several complexes of this type have been reported.

Another example of an enantioselective synthesis of complex having a stereogenic metal center and bearing only monodentate ligands is shown in FIG. 5. However, diastereomers formed from the reaction of Na mentholate with racemic complex 9 were separated by crystallization. Saponification was performed to regenerate complex 9, now enantioenriched, whose only stereogenic element is the metal center. Prochiral complexes, such as 10, can be desymmetrized by displacement of one of the carbonyl ligands with a chiral monodentate phosphine, as shown in FIG. 6. The reaction was not stereoselective and the two diastereomers generated, 11a and 11b, were separated by chromatography or fractional crystallization. It should also be noted that "piano stool" complexes, such as complexes 7-11, have an octahedral geometry (i.e. they are not tetrahedral).

Complexes 13-15, as shown in FIG. 3, are olefin metathesis catalysts. Complexes 14-15, as well as Re complex 7, are stereogenic metal complexes with an alkoxide ligand, however, all of these complexes comprise of racemic mixtures. Complex 14 has shown unique reactivity for enyne metathesis.

Previous studies have focused on the use of chiral, terpene-derived, alcohols for stereoselective synthesis of tetrahedral Mo alkylidenes. Generally, Mo monoalkoxide complexes are generated as a 1:1 mixture of diastereomers. Additionally, reaction of many alcohols with Mo bis(pyrrolide) complexes may result in substitution of both pyrrolide ligands to generate a bis(alkoxide) complex (e.g., Mo is not a stereogenic center). However, FIG. 7 shows the reaction of Mo bis(pyrrolide) 16a with one equivalent of borneol 17, resulting in the generation of monoalkoxide complex 18 with 3:1 diastereoselectivity.

Chiral ligands typically used for enantioselective Mo-catalyzed olefin metathesis have been diols derived from BINOL or a chiral biphenol, as shown in FIG. 8.

The use of a chiral alcohol in enantioselective catalysis has been attempted before. For example, a mono-protected BINOL derivative was employed in a Brnsted acid-catalyzed enantioselective Morita-Baylis-Hillman reaction, as shown in FIG. 9A. The catalysts were relatively unreactive (up to 43% yield) and the products racemic; chiral diols proved to be more reactive and selective catalysts. Monodentate alcohols have also been used in the synthesis of organometallic compounds, as shown in FIG. 9B.

In some cases, it may be desirable to utilize a chiral metal complex having a stereogenic metal center. However, there are often challenges associated with synthesizing and/or utilizing such metal complexes. For example, the stereoselective synthesis of metal complexes having a stereogenic metal center has been shown to be difficult. Also, such metal complexes have exhibited stereomutation at the metal center and/or loss of stereochemistry due to labile ligands. For example, in an olefin metathesis cycle, the metal center may undergo "inversion" or racemization by non-productive olefin metathesis.

Accordingly, improved compositions and methods are needed.

SUMMARY OF THE INVENTION

The present invention relates to compositions comprising a metal complex comprising a stereogenic metal atom and two or more ligands, wherein each ligand associated with the metal complex comprises an organic group and binds the stereogenic metal atom via one site of the ligand, wherein the composition comprises the metal complex in a diastereomeric ratio greater than 1:1.

The present invention also provides methods for synthesizing a metal complex comprising a stereogenic metal atom comprising reacting, in a reaction vessel, an organometallic composition having a plane of symmetry or a racemic mixture of an organometallic composition comprising a stereogenic metal center, with a monodentate ligand lacking a plane of symmetry, to produce a metal complex comprising a stereogenic metal atom and two or more ligands, wherein the metal complex is produced in a diastereomeric ratio greater than 1:1, in the reaction vessel, and each ligand of the metal complex binds the stereogenic metal atom via one bond.

The present invention also provides methods for catalyzing a reaction comprising catalyzing a metathesis reaction in a reaction vessel with a catalyst comprising a stereogenic metal atom and two or more ligands, wherein each ligand associated with the metal complex binds the stereogenic metal atom via one site of the ligand, and wherein the metathesis reaction produces a product in an enantiomeric excess greater than 50%.

The present invention also provides methods for catalyzing a reaction comprising catalyzing a metathesis reaction in a reaction vessel with a catalyst comprising a stereogenic metal atom and a monodentate alcohol lacking a plane of symmetry, in the reaction vessel, wherein the metathesis reaction produces a product in an enantiomeric excess greater than 50%.

In some embodiments, the present invention provides methods comprising reacting a first species comprising a cyclic olefin and a second species comprising an olefin via a ring-opening cross-metathesis reaction to produce a product comprising a double bond, the double bond comprising an atom of the first species and an atom of the second species, wherein the double bond is produced in a Z:E ratio greater than about 3:1 in favor of the Z-isomer.

The present invention also provides methods comprising reacting a first species comprising an olefin and a second species comprising an olefin via a cross-metathesis reaction to produce a product comprising a double bond, the double bond comprising an atom of the first species and an atom of the second species, wherein the double bond is produced in a Z:E ratio greater than about 1:1 in favor of the Z-isomer.

In some embodiments, the present invention provides methods comprising reacting a first species comprising an olefin and a second species comprising an alkyne via a metathesis reaction to produce a product comprising a double bond and at least one stereogenic carbon, the double bond comprising an atom of the first species and an atom of the second species, wherein the at least one stereogenic carbon atom is produced in an enantiomeric excess greater than about 50%.

The present invention also provides methods comprising reacting a first species comprising an olefin and a second species comprising a vinyl ether via a metathesis reaction to produce a product comprising a double bond, the double bond comprising an atom of the first species and an atom of the second species, wherein the double bond is produced in a Z:E ratio greater than about 4:1 in favor of the Z-isomer.

Figure 1:
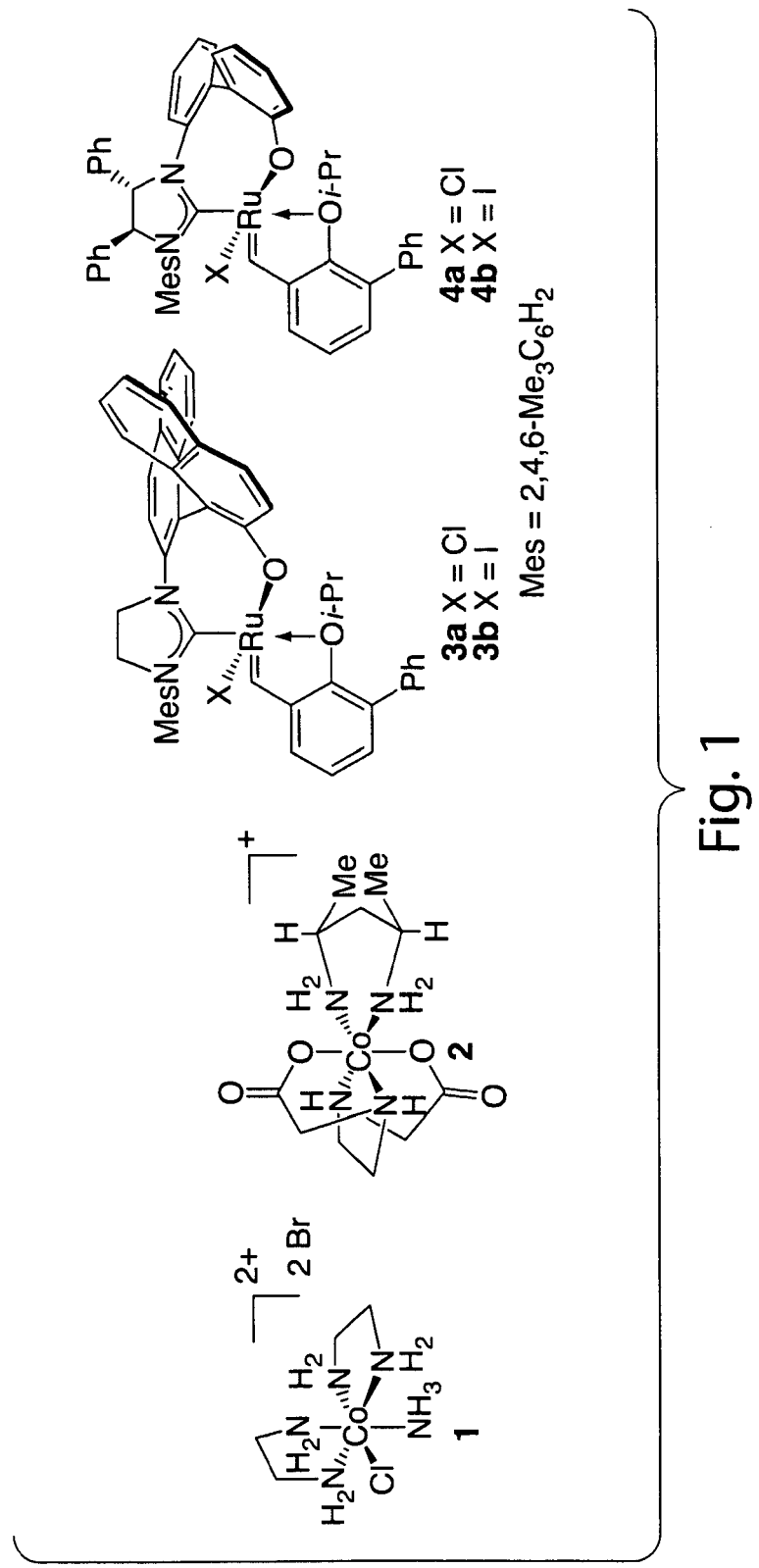
FIG. 1 shows examples of stereogenic metal complexes bearing polydentate ligands.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to metal complexes and related methods. In some cases, metal complexes of the invention useful as catalysts for chemical reactions, including metathesis reactions, are provided. The catalysts may exhibit enhanced activity and stereoselectivity, relative to known methods.

In some embodiments, the invention provides methods for enantioselective or stereoselective metathesis reactions. As used herein, the term "metathesis reaction" is given its ordinary meaning in the art and refers to a chemical reaction in which two reacting species exchange partners in the presence of a transition-metal catalyst. In some cases, a byproduct of a metathesis reaction may be ethylene. A metathesis reaction may involve reaction between species comprising, for example, olefins and/or alkynes. Examples of different kinds of metathesis reactions include cross metathesis, ring-closing metathesis, ring-opening metathesis, acyclic diene metathesis, alkyne metathesis, enyne metathesis, and the like. In some cases, the methods of the present invention allow for the formation of a metathesis product with high enantioselectivity and/or high ratio of Z:E isomers, as described herein.

In some cases, the present invention also provides the ability to produce metal complexes comprising a stereogenic metal atom. As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In a particular embodiment, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral, molecular product. Such metal complexes may exhibit improved catalytic activity and stereoselectivity, relative to previous systems, and undesired side reactions (e.g., dimerization or oligomerization of the metal complex) may be reduced.

Some aspects of the invention can be realized with metal complexes comprising two or more ligands, wherein each ligand is a monodentate ligand, i.e., each ligand binds or coordinates the metal center via one coordination site of the metal only, or via one site of the ligand only. That is, in some cases, the metal complex does not comprise one or more bidentate, a tridentate, a quatradentate, etc., ligands. Metal complexes comprising primarily monodentate ligands, as described herein, may exhibit enhanced catalytic activity and stability relative to a similar complex comprising a bidentate or other multidentate ligand. For example, catalysts comprising only monodentate ligands may be prepared in high yields using the methods of the invention.

In some cases, the present invention may also provide one-pot procedures involving the formation of a catalyst and subsequent use of the catalyst in a chemical reaction. The term "one-pot" reaction is known in the art and refers to a chemical reaction which can produce a product in one step which may otherwise have required a multiple-step synthesis, and/or a chemical reaction comprising a series of steps that may be performed in a single reaction vessel. One-pot procedures may eliminate the need for isolation (e.g., purification) of catalysts and/or intermediates, while reducing the number of synthetic steps and the production of waste materials (e.g., solvents, impurities). Additionally, the time and cost required to synthesize catalysts and/or other products may be reduced. In some embodiments, a one-pot synthesis may comprise simultaneous addition of at least some components of the reaction to a single reaction chamber. In one embodiment, the one-pot synthesis may comprise sequential addition of various reagents to a single reaction chamber. Some embodiments of the invention may provide compositions comprising a metal complex. In some cases, the metal complex comprises a stereogenic metal atom, and two or more ligands that bind the metal atom. In some embodiments, each ligand associated with the metal complex comprises an organic group. The ligands may be monodentate ligands, i.e., the ligands bind the stereogenic metal atom via one site of the ligand (e.g., a carbon atom or a heteroatom of the ligand). In some cases, a monodentate ligand may bind the metal center via a single bond or a multiple bond. In some cases, the metal complex comprises at least one ligand lacking a plane of symmetry. That is, at least one ligand bound to the stereogenic metal atom is a chiral ligand. In some cases, the metal complex comprises an oxygen-containing ligand, including chiral and/or achiral oxygen-containing ligands. In some cases, the metal complex comprises a nitrogen-containing ligand, including chiral and/or achiral nitrogen-containing ligands. For example, the ligand may be a chiral or achiral nitrogen heterocycle, such as a pyrrolide. In some cases, the metal atom may be bound to at least one carbon atom.

In some embodiments, the composition comprises the metal complex in a diastereomeric ratio greater than 1:1. In some cases, the composition comprises the metal complex in a diastereomeric ratio greater than about 5:1, greater than about 7:1, greater than about 10:1, greater than about 20:1, or, in some cases, greater.

In some embodiments, the metal complex has the structure,

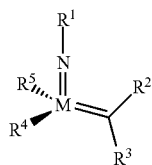

wherein M is Mo or W; $R^1$ is aryl, heteroaryl, alkyl, heteroalkyl, optionally substituted; $R^2$ and $R^3$ can be the same or different and are hydrogen, alkyl, heteroalkyl, aryl, or heteroaryl, optionally substituted; and $R^4$ and $R^5$ can be the same or different and are alkyl, heteroalkyl, aryl, or heteroaryl, optionally substituted.

In some cases, $R^1$ is aryl or alkyl, optionally substituted with one or more of $R^5$; $R^2$ is hydrogen, alkyl, or aryl, optionally substituted; $R^3$ is alkyl, dialkyl amine, achiral alkoxide, or heteroaryl, optionally substituted; $R^4$ comprises a chiral biaryl group, optionally substituted; and $R^5$ is alkyl, heteroalkyl, aryl, heteroaryl, halogen, or a silyl group, optionally substituted. However, in some cases, $R^1$ is aryl or alkyl, optionally substituted with one or more of $R^4$; $R^2$ is hydrogen, alkyl, or aryl, optionally substituted; $R^3$ is alkyl, dialkyl amine, achiral alkoxide, or heteroaryl, optionally substituted; $R^4$ is alkyl, heteroalkyl, aryl, heteroaryl, halogen, or a silyl group, optionally substituted; and $R^5$ comprises a chiral biaryl group, optionally substituted.

In some cases, $R^2$ is alkyl.

In one set of embodiments, $R^4$ is an oxygen-containing ligand lacking a plane of symmetry or nitrogen-containing ligand lacking a plane of symmetry; and $R^5$ is alkyl, dialkyl amine, achiral alkoxide, or a group having the structure,

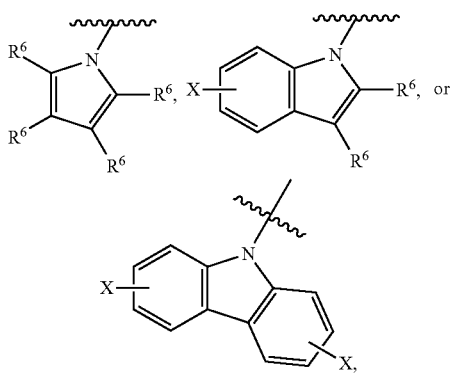

wherein each $R^6$ can be the same or different and is hydrogen, alkyl, heteroalkyl, aryl, heteroaryl, or is an oxygen-containing ligand lacking a plane of symmetry or a nitrogen-containing ligand lacking a plane of symmetry, optionally substituted; and X may be present or absent and is any non-interfering group. As used herein, the term "non-interfering group," refers to any group (e.g., an organic group or permissible substituent to an organic group) which does not significantly effect or alter the properties (e.g., catalytic activity, solubility, etc.) of the compound. For example, a metal complex including a non-interfering group may exhibit at least 90% of the catalytic activity of an essentially identical metal complex lacking the non-interfering group. Non-limiting examples of non-interfering groups includes methyl, ethyl, protecting groups, and the like.

In some cases, the metal complex may comprise one or more oxygen-containing ligands lacking a plane of symmetry or nitrogen-containing ligands lacking a plane of symmetry. In some embodiments, such ligands may coordinate the metal atom via an oxygen atom (e.g., via a hydroxyl group), or other atom of the ligand. The oxygen-containing ligand may coordinate the metal atom via one site of the ligand, i.e., the ligand may be a monodentate ligand.

Figure 10:
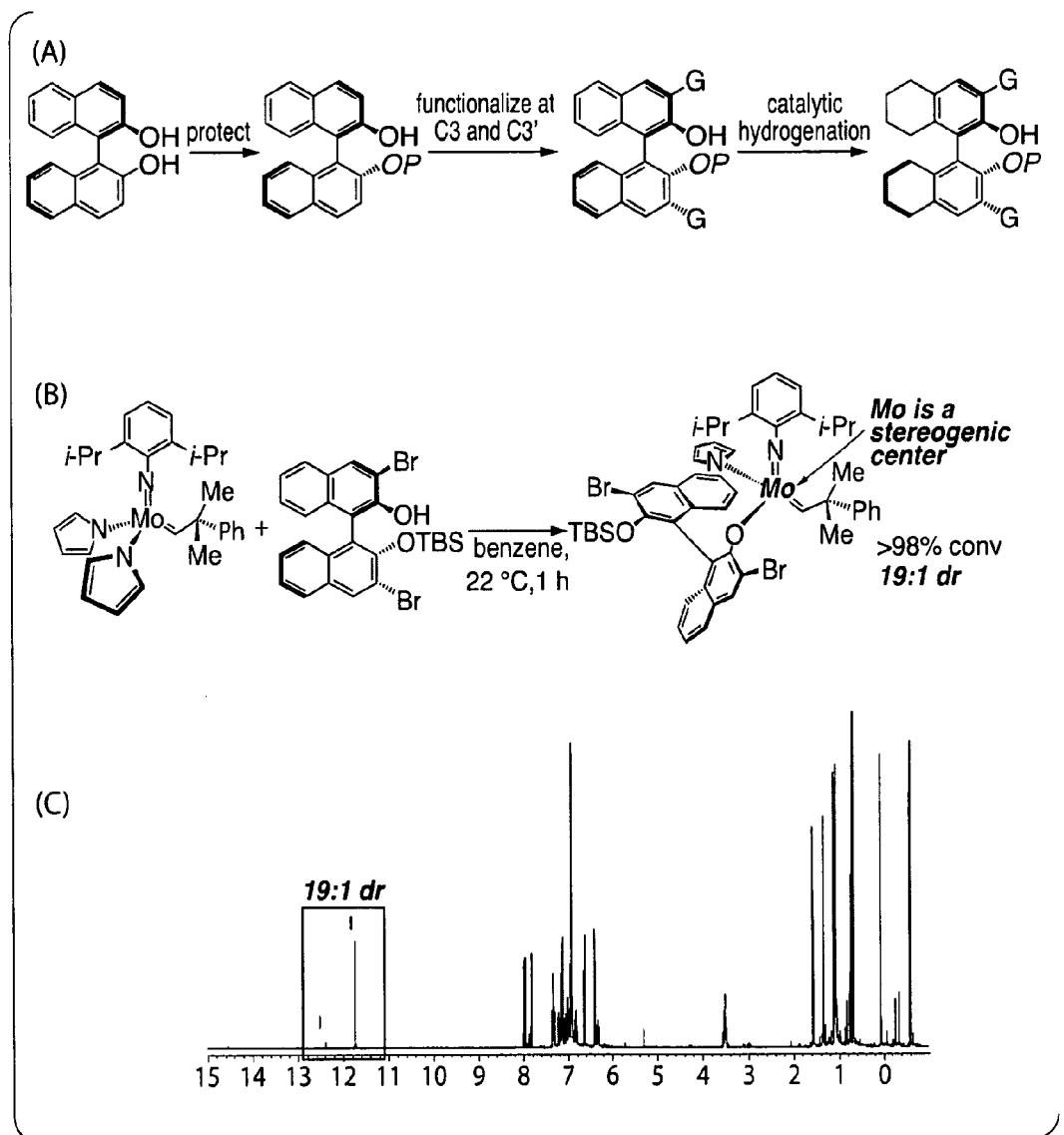
FIG. 10 shows (A) the synthesis of a chiral alcohol, (B) the synthesis of a Mo complex comprising the chiral alcohol, and (C) a $^1$H NMR of the Mo complex comprising the chiral alcohol.

In one set of embodiments, a ligand may comprise two sites capable of binding the metal center, wherein a first site is bonded to a protecting group, or other group, that may reduce the ability of the first site to coordinate the metal, and the second site coordinates the metal center. For example, the ligand may be a BINOL derivative comprising two hydroxyl groups, wherein one hydroxyl group is bonded to a protecting group (e.g., a silyl protecting group) and another hydroxyl group coordinates the metal center. A non-limiting example of the synthesis of a BINOL or hydrogenated BINOL derivative comprising a protecting group is shown in FIG. 10A.

In some cases, the oxygen-containing ligand lacking a plan of symmetry may comprise the following structure,

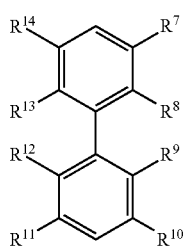

wherein $R^7$ is aryl, heteroaryl, alkyl, or heteroalkyl, optionally substituted; $R^8$ is hydrogen, —OH, halogen, alkyl, heteroalkyl, aryl, heteroaryl, acyl, acyloxy, or —OP, optionally substituted; or, together $R^7$ and $R^8$ are joined to form a ring, optionally substituted; $R^9$ is —OH, —OP, or amino, optionally substituted; $R^{10}$ is hydrogen, halogen, alkyl, heteroalkyl, aryl, heteroaryl, or acyl, optionally substituted; each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted; and P is a protecting group. The ring may be an aromatic or a non-aromatic ring. In some embodiments, the ring may be a heterocycle. In some cases, the protecting group may be a Si protecting group (e.g., tri-butyl silyl or TBS). In some embodiments, the oxygen-containing ligand may comprise a substituted alkyl group, such as $CF_3$.

In some embodiments, $R^8$ and $R^9$ are attached to the biaryl parent structure via a heteroatom, such as an oxygen atom. For example, $R^8$ and $R^9$ can be —OH, alkoxy, aryloxy, acyloxy, or —OP, where P is a protecting group (e.g., Si protecting group). In some cases, $R^8$ is —OP and $R^9$ is —OH or amino.

Examples of oxygen-containing ligands lacking a plane of symmetry or nitrogen-containing ligands lacking a plane of symmetry include ligands shown in the Examples below, as well as the following structures,

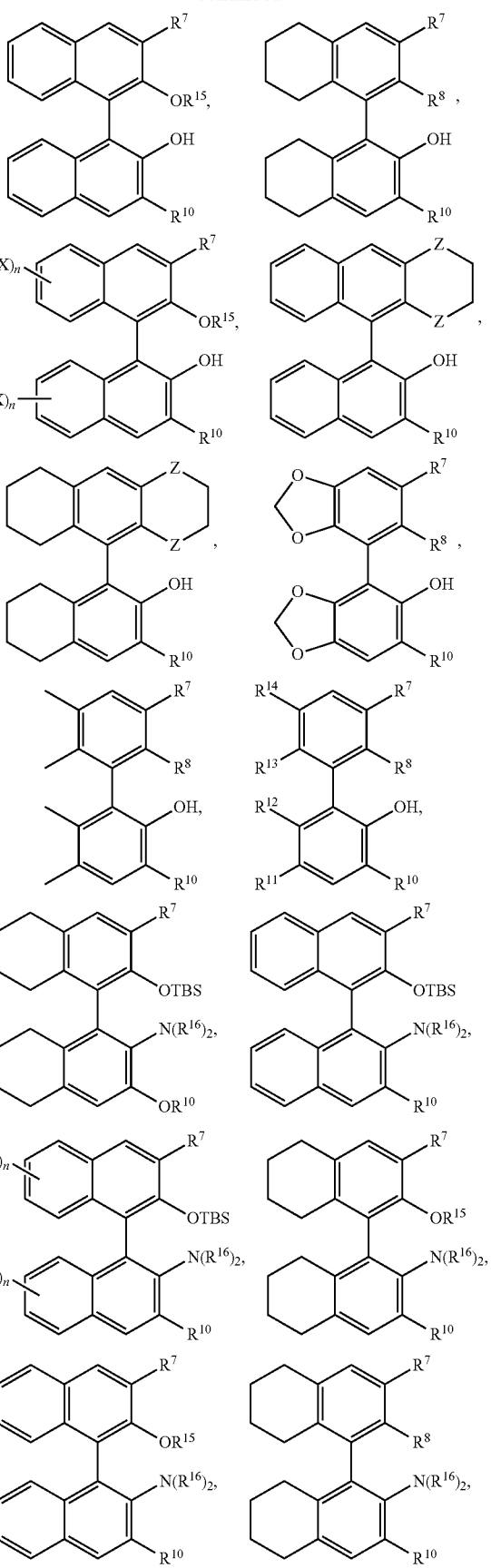

-continued

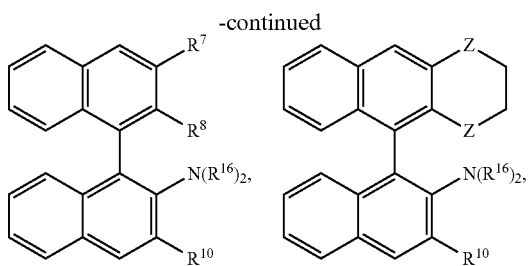

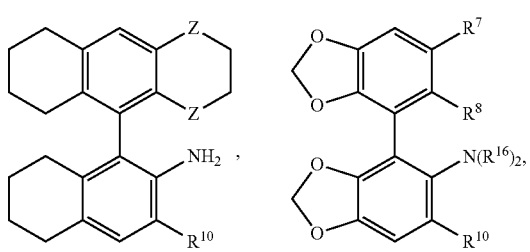

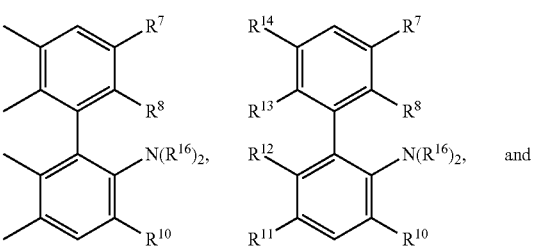

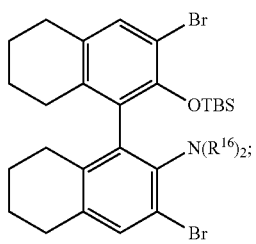

wherein each $R^7$ and $R^8$ can be the same or different and is hydrogen, halogen, alkyl, alkoxy, aryl, $CF_3$, Si-tri-alkyl, Si-tri-aryl, Si-alkyl-diphenyl, Si-phenyl-dialkyl, or acyl (e.g., ester); $R^{10}$ is hydrogen, halogen, alkyl, heteroalkyl, aryl, heteroaryl, or acyl, optionally substituted; each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted; $R^{15}$ is alkyl, aryl, Si-trialkyl, Si-triaryl, Si-alkyldiphenyl, Si-phenyldialkyl, or acyl; $R^{16}$ is hydrogen or an amine protecting group; X can be any non-interfering group; each Z can be the same or different and is $(CH_2)_m$, N, O, optionally substituted; n is 0-5; and m is 1-4.

In some cases, each $R^7$ and $R^{10}$ is the same or different and is halogen, methyl, t-butyl, $CF^3$, or aryl, optionally substituted.

In some embodiments, $R^4$ is silyl-protected BINOL derivative.

In some embodiments, $R^1$ is

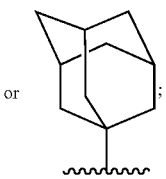

to wherein each $R^{17}$ can be the same or different and is hydrogen, halogen, alkyl, heteroalkyl (e.g., alkoxy), aryl, acyl, or —OP, optionally substituted, where P is a protecting group.

In some embodiments, $R^1$ is

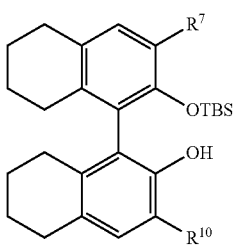

$R^2$ is $CMe_2Ph$ or $CMe_3$; and $R^4$ is an enantiomer of the following structure,

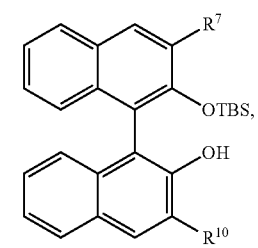

wherein each $R^{17}$ is the same or different and is halogen, methyl, t-butyl, $CF_3$, or aryl, optionally substituted. In some cases, $R^2$ is $CMe_2Ph$ or $CMe_3$, and $R^3$ is hydrogen.

In some embodiments, the metal complex comprises one of the following structures,

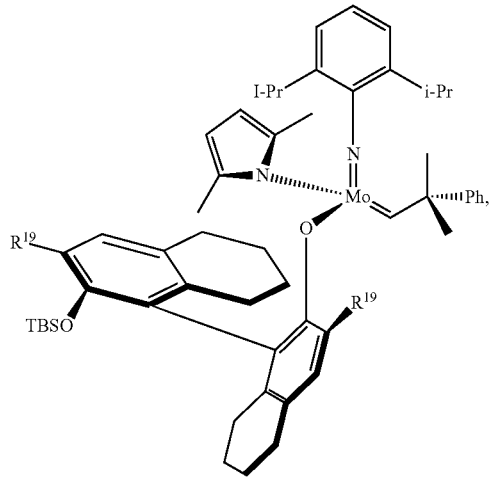

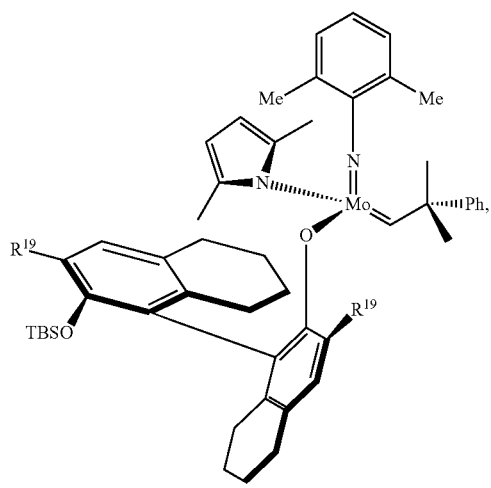

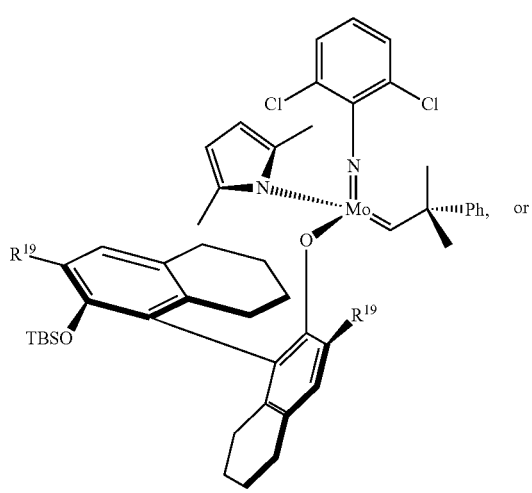

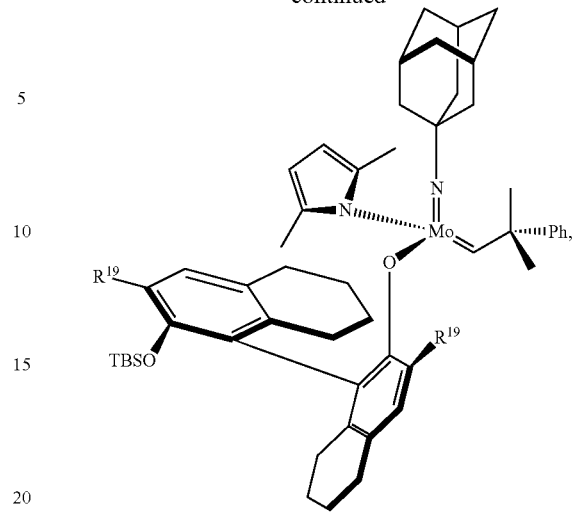

wherein $R^{19}$ is F, Cl, Br, or I.

In some cases, $R^1$ may be linked to form a ring with $R^2$ or $R^3$. For example, the metal complex may comprise $R^1$ linked to form a ring with $R^2$ or $R^3$ prior to use as a catalyst, and, upon initiation of the catalyst in a metathesis reaction, the linkage between $R^1$ and $R^2$ or $R^3$ may be broken, therefore rendering each of the ligands monodentate. The ring may comprise any number of carbon atoms and/or heteroatoms. In some cases, the cyclic olefin may comprise more than one ring. The ring may comprise at least 4, at least 5, at least 6, at least 7, at least 8, at least 9, at least 10, or more, atoms.

In some embodiments, the invention provides methods for synthesizing a metal complex comprising a stereogenic metal atom. For example, the method may comprise reacting an organometallic composition (e.g., a precatalyst) having a plane of symmetry with a monodentate ligand lacking a plane of symmetry, to produce a metal complex (e.g., catalyst) comprising a stereogenic metal atom. In some cases the method may comprise reacting a racemic mixture of an organometallic composition comprising a stereogenic metal center with a monodentate ligand lacking a plane of symmetry, to produce a metal complex comprising a stereogenic metal atom. The metal complex may comprise two or more ligands, wherein each ligand binds the stereogenic metal atom via one bond, i.e., each ligand is a monodentate ligand.

Figure 11:
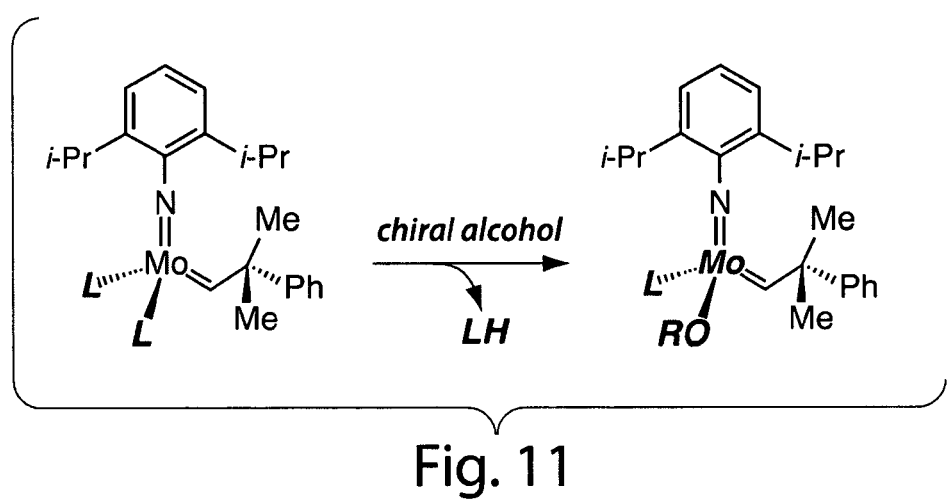
FIG. 11 shows an example of the synthesis of a stereogenic-at-Mo complex, according to one embodiment.

In some cases, the method may comprise providing a catalyst precursor comprising an organometallic composition having a plane of symmetry and including two or more ligands, in a reaction vessel. At least one ligand may be replaced by a monodentate ligand (e.g., oxygen-containing or nitrogen-containing ligand), thereby synthesizing a metal complex comprising the stereogenic metal atom. In some cases, the metal complex may be used as a catalyst for a metathesis reaction, as described more fully below. A non-limiting example of the synthesis of a metal complex comprising a stereogenic metal atom is shown in FIG. 11.

Figure 12A:
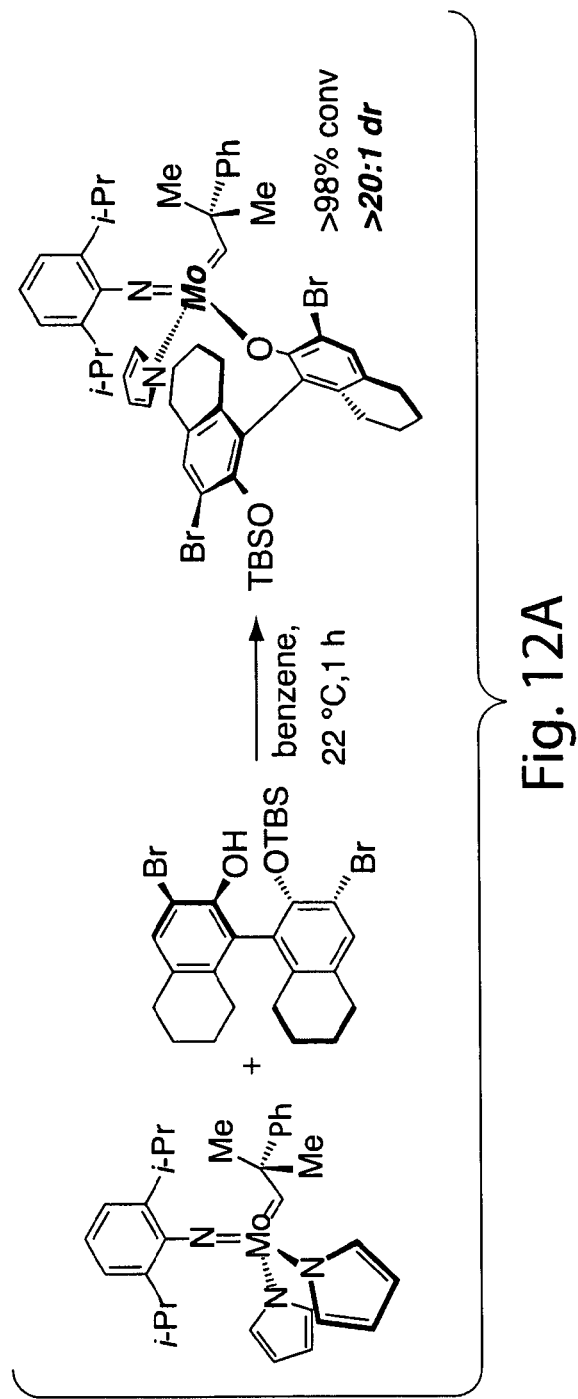
FIGS. 12A and 12B show the syntheses of stereogenic-at-Mo complexes for enantioselective olefin metathesis.
Figure 12B:
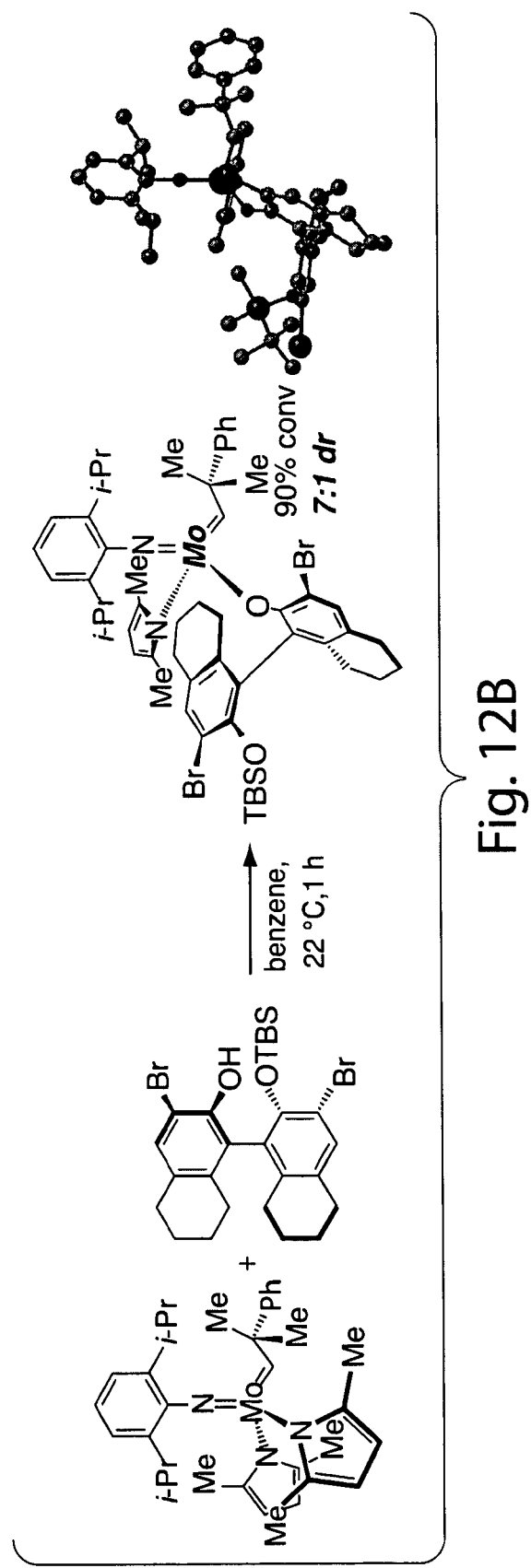
Figure 35:
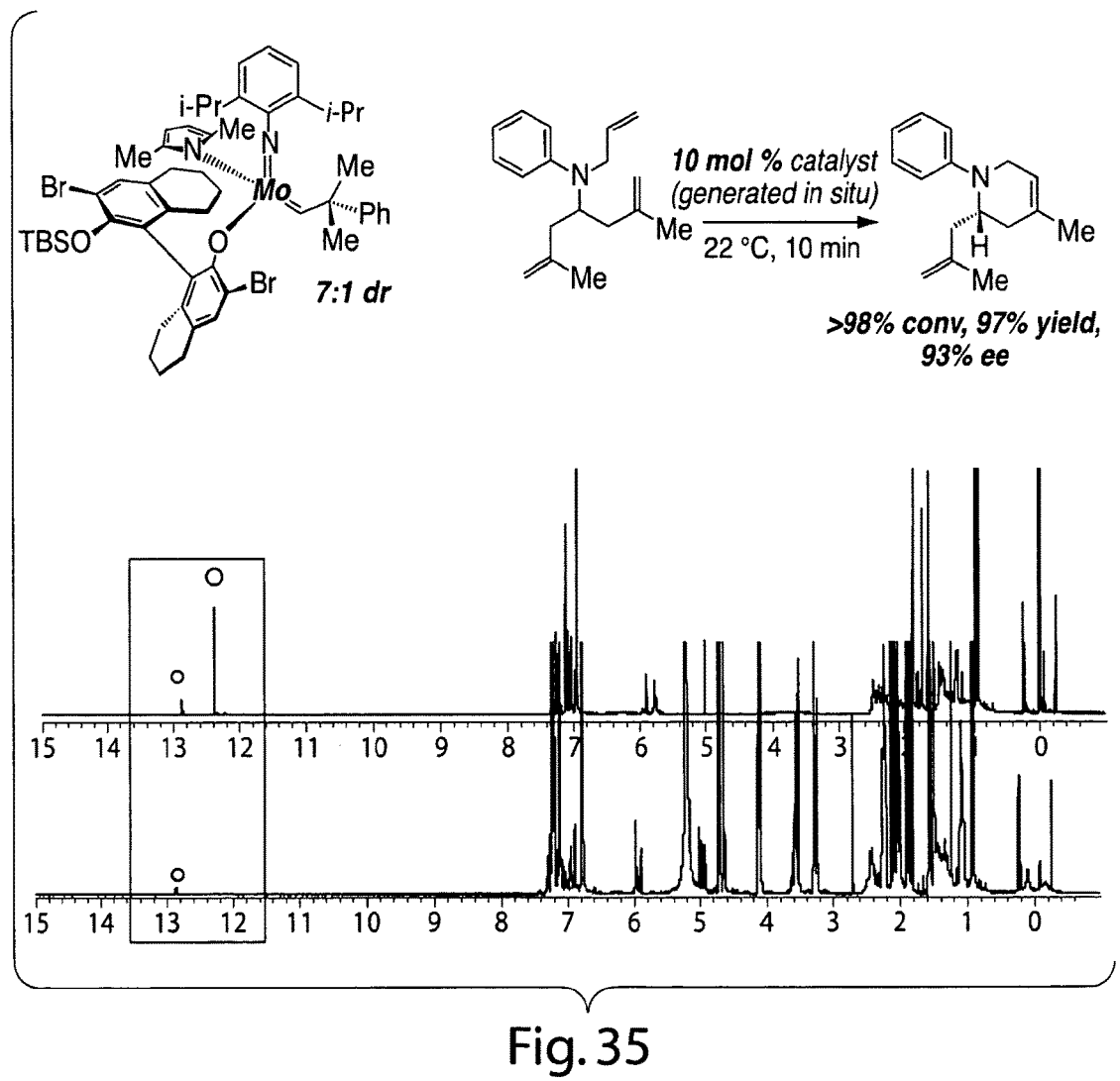
FIG. 35 shows NMR spectra of each diastereomer of a Mo-complex, according to one embodiment of the invention, and consumption of one Mo diastereomer in an olefin metathesis reaction.

In some embodiments, the metal complex may be produced, in the reaction vessel, in a diastereomeric ratio greater than 1:1. In some cases, the metal complex is produced in a diastereomeric ratio greater than about 5:1, greater than about 7:1, greater than about 10:1, greater than about 20:1, or, in some cases, greater, in the reaction vessel. That is, the metal complex may be stereoselectively formed in the reaction vessel, without need for an auxiliary ligand, and/or other purification steps, (e.g., crystallization) to obtain a particular diastereomer. FIG. 10B and FIGS. 12A-B show non-limiting examples of the replacement of an achiral ligand with a chiral oxygen-containing ligand. In cases, the ratio of diastereomers formed may be determined by NMR spectroscopy, as shown in FIG. 10C and FIG. 35.

The metal complexes (e.g., catalysts) may be isolated, or may be formed in situ and utilized in a subsequent reaction (e.g. one-pot reaction). In some cases, the metal complex may be isolated as a Lewis base adduct. The terms "Lewis base" and "Lewis base adduct" are known in the art and refer to a chemical moiety capable of donating a pair of electrons to another chemical moiety. For example, the metal complex may be combined with tetrahydrofuran (THF), wherein at least one THF molecules coordinate the metal center to form a Lewis base adduct. In some cases, the Lewis base adduct may be $PMe_3$. In some embodiments, the coordination of Lewis base molecules to the metal complex may produce a plane of symmetry with respect to the metal center. However, the stereogenic metal center may be reformed by facile removal of the Lewis base molecules. For example, the metal complex may be formed and stored as a Lewis base adduct, and may be "activated" in a subsequent reaction step to restore the original stereogenic metal center.

In some cases, the method may further comprise reacting the metal complex comprising the stereogenic metal center to replace one or more ligands with a different ligand. For example, the metal complex comprising the stereogenic metal center may include a chiral ligand, which may be subsequently replaced with an achiral ligand to produce a metal complex having a stereogenic metal center, wherein each ligand bound to the metal is an achiral ligand. For example, upon desymmetrizing an achiral metal complex with a chiral oxygen-containing ligand (e.g., chiral alcohol) to form a metal complex having a stereogenic metal center, the oxygen-containing ligand may be replaced by an achiral oxygen-containing ligand, or other achiral ligand.

The synthesis of the metal complex (e.g., catalyst) may be performed by reacting a precatalyst in the presence of a solvent, such as an organic solvent (e.g., benzene, toluene, dichloromethane, etc.), or may be performed in the absence of solvent (e.g., neat). In some embodiments, in the synthesis of the composition, the ratio of precatalyst (e.g., an organometallic composition having a plane of symmetry or a racemic mixture of an organometallic composition comprising a stereogenic metal center) to monodentate ligand provided to the reaction vessel may be about 3:1, about 2:1, about 1:1, about 1:2, or the like. In some cases, about one equivalent on monodentate ligand may be reacted with the precatalyst. The reaction may advantageously be conducted at room temperature, below room temperature, or at higher temperatures, to suit a particular application, as described herein.

Using the teachings described herein, one of ordinary skill in the art would be able to select or determine the appropriate combinations of catalyst precursor (e.g., organometallic complex), ligands, and reactions conditions (e.g., solvent, reaction temperature, etc.) suitable for use in a particular application.

Some embodiments of the invention provide methods for catalyzing a reaction. In some embodiments, the reaction may be a metathesis reaction. In some cases, the method may involve catalyzing a metathesis reaction in a reaction vessel with a catalyst comprising a stereogenic metal atom and two or more ligands. In some cases, each ligand associated with the metal complex binds the stereogenic metal atom via one site of the ligand. In some cases, the method involves catalyzing a metathesis reaction in a reaction vessel with a catalyst comprising a stereogenic metal atom and a monodentate alcohol lacking a plane of symmetry, in the reaction vessel. Illustrative embodiments of the use of metal complexes described herein in various catalytic reactions, including metathesis reactions, may be found in the Examples.

In some cases, the metathesis reaction may comprise reacting a species or substrate having a plane of symmetry to produce a product lacking a plane of symmetry. For example, an achiral substrate comprising at least one carbon-carbon double bond or carbon-carbon triple bond may be reacted via a metathesis reaction using catalysts as described herein to produce a chiral product. In some cases, the metathesis reaction may produce a product in an enantiomeric excess greater than about 50%, greater than about 60%, greater than about 70%, greater than about 80%, greater than about 90%, or, in some cases, greater than about 98%. The terms "enantiomeric excess" or "e.e." are given their ordinary meaning in the art and refer to the absolute difference between the mole fractions of each enantiomer present in a product. The catalysts may also exhibit high conversion rates. For example, the metathesis reaction may be performed with a yield of at least about 50%, at least about 60%, at least about 70%, at least about 80%, at least about 90%, or, in some cases, at least about 98%.

In some embodiments, the present invention provides methods involving metathesis reactions (e.g., using one or more catalysts described herein) and the formation of various products. The methods described herein may advantageously allow for the enantioselective formation of products, i.e., may produce products having a high enantiomeric excess. In some embodiments, the methods may provide the ability to selectively synthesize, via a metathesis reaction, products having a Z or E configuration about a double bond. In some cases, the method involves reacting a first species and a second species to form a product comprising a double bond, wherein the double bond comprises an atom of the first species and an atom of the second species. In some embodiments, the double bond may comprise a carbon atom from the first species and a carbon atom from the second species. The double bond produced may have a Z (e.g., cis) or E (e.g., trans) configuration. Those of ordinary skill in the art would understand the meaning of the terms "cis" or "Z" and "trans" or "E," as used within the context of the invention.

In some embodiments, the double bond may be produced in a Z:E (i.e., cis:trans) ratio greater than about 1:100, greater than about 1:50, greater than about 1:20, greater than about 1:10, greater than about 1:5, greater than about 1:2. In other embodiments, the double bond may be produced in a Z:E ratio greater than about 1:1, greater than about 2:1, greater than about 3:1, greater than about 4:1, greater than about 5:1, greater than about 10:1, greater than about 20:1, greater than about 30:1, greater than about 40:1, greater than about 50:1, greater than about 75:1, greater than about 100:1, or greater. In some cases, the Z or cis selectivity may be expressed as a percentage of product formed. In some cases, the product may be greater than about 50% Z, greater than about 60% Z, greater than about 70% Z, greater than about 80% Z, greater than about 90% Z, greater than about 95% Z, greater than about 98% Z, greater than about 99% Z, or, in some cases, greater.

Figure 13:
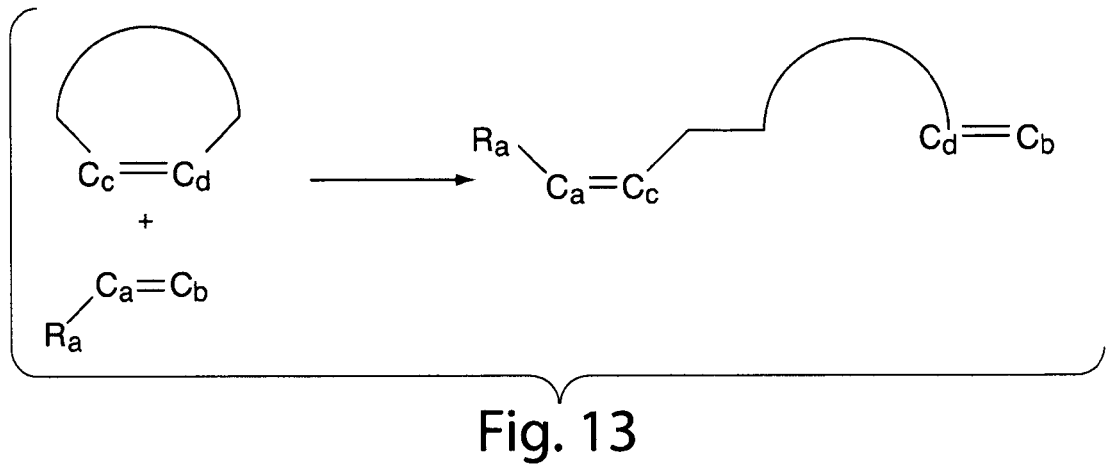
FIG. 13 shows a schematic representation of a metathesis reaction between a cyclic olefin and an olefin and the formation of a Z product.

In some cases, the metathesis reaction may comprise reacting a first species comprising a cyclic olefin and a second species comprising an olefin in the presence of a catalyst of the invention. The first species and the second species may be reacted via a ring-opening cross metathesis reaction to produce a double bond comprising a first atom of the first species and a second atom of the second species. For example, as shown in FIG. 13, a first species comprises a cyclic olefin (e.g., $C_c\!\!=\!\!C_d$) and a second species comprises an olefin (e.g., $C_a\!\!=\!\!C_b$) may be reacted via a ring-opening cross metathesis reaction to produce a product having a double bond, which may be formed in a Z:E ratio greater than at least about 3:1, or greater.

Figure 14:
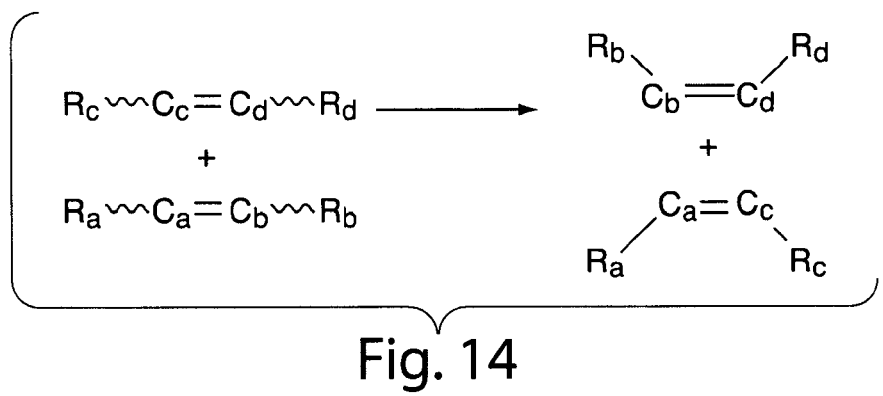
FIG. 14 shows a schematic representation of a metathesis reaction between a first olefin and a second olefin to produce a product bearing a Z double bond.

In some cases, the metathesis reaction may involve a cross-metathesis reaction between a first species and a second species, each comprising an olefin, in the presence of a catalyst of the invention. The reaction may produce a product comprising a double bond in a Z:E ratio greater than at least about 1:1. For example, as shown in FIG. 14, a species comprising a cyclic olefin (e.g., $C_c\!\!=\!\!C_d$) and second species comprising an olefin ($C_a\!\!=\!\!C_b$) may be reacted to form a double bond in a Z:E ratio greater than at least about 1:1.

Figure 15:
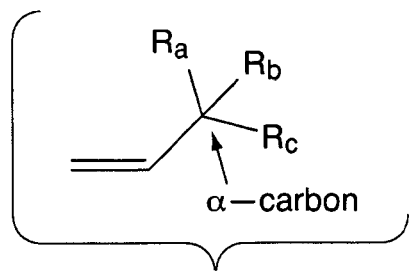
FIG. 15 shows an olefin and the location of an alpha-carbon with respect to the olefin.

In some cases, the metathesis reaction may involve an enantioselective enyne metathesis reaction between a first species comprising an olefin and a second species comprising an alkyne. For example, the metathesis reaction may be a ring-closing enyne metathesis. In some cases, the reaction may be conducted in the presence of a catalyst described herein under an atmosphere of ethylene. The ring-closing enyne metathesis reaction may produce a product, wherein at least one carbon atom of the product may be a stereogenic atom (e.g., produced in an enantiomeric excess). The stereogenic carbon atom may be in an alpha, beta, gamma, etc., position relative to the double bond. As used herein, the term "alpha carbon" is given its ordinary meaning and refers to a carbon atom that is adjacent and directly attached to a functional group (e.g., an olefin). FIG. 15 shows an example of a stereogenic alpha-carbon with respect to an olefin. Those of ordinary skill in the art would know the meaning of the terms "beta carbon" and "gamma carbon," as used within the context of the invention. In some cases, the stereogenic carbon atom is produced in an enantiomeric excess greater than about 50%, or more.

Figure 16:
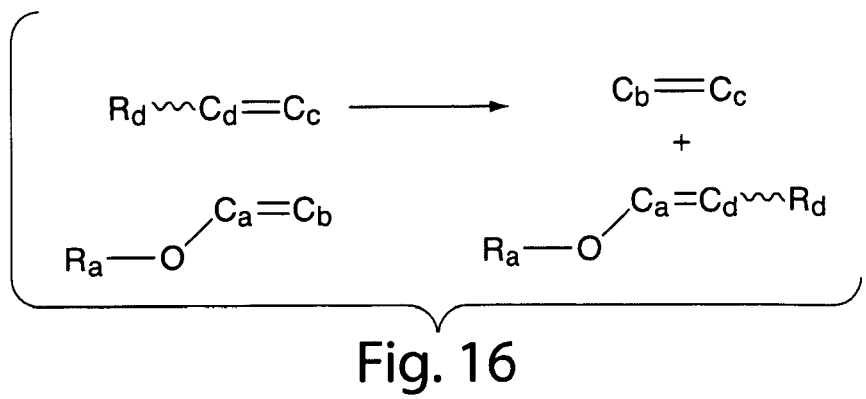
FIG. 16 shows a schematic of a metathesis reaction between an olefin and vinyl ether.

In some cases, the metathesis reaction may comprise reacting a first species comprises an olefin and a second species comprises a vinyl ether. The reaction may produce a product comprising a double bond, which may be formed in a Z:E ratio greater than about 4:1, or greater. As used herein, the term "vinyl ether" is given its ordinary meaning and refers to a molecule comprising the group —CHCHOR[18], wherein and R[18] is halogen, alkyl, heteroalkyl, aryl, or heteroaryl, optionally substituted, for example, with a silyl protecting group. Non-limiting examples of vinyl ethers include vinyl ethyl ether, cyclohexyl vinyl ether, 4-hydroxybutyl vinyl ether, n-butyl vinyl ether, isobutyl vinyl ether, n-propyl vinyl ether, and isopropyl vinyl ether. FIG. 16 shows an example of a cross metathesis reaction between a vinyl ether and an olefin. In some cases, the product is produced with high enantioselectivity (e.g., greater than about 50%), and/or in a high Z:E ratio (e.g., greater than about 4:1).

As described herein, catalysts comprising a stereogenic metal center may exhibit improved catalytic activity and/or stereoselectivity, relative to catalysts comprising non-stereogenic metal centers. Without wishing to be bound by theory, this may be attributed to the energetically accessibly metallacyclobutane intermediate formed during, for example, a metathesis reaction.

Some embodiments of the invention include the use of additional components or reagents to facilitate formation of the metal complex and/or performance of the catalyst. For example, in catalytic reactions using metal complexes described herein, a Lewis base may be added.

Those of ordinary skill in the art, in combination with the teachings described herein, would be able to select appropriate combinations of catalysts, substrates, and reactions conditions (e.g., solvent, reaction temperature, etc.) suitable for use in a particular application. For example, a simple screening test may involve the reaction of an achiral substrate in the presence of various metal catalysts, wherein the resulting yield and/or enantioselectivity may determine the effectiveness and/or activity of a particular catalyst in the reaction.

Methods of the invention may be advantageous in that, in some cases, a catalyst may be prepared under relatively mild conditions and in high yields. For example, the replacement of the nitrogen-containing ligand(s) of a precatalyst with oxygen-containing ligand(s) to form the catalyst may occur at a temperature of less than about 100° C. and with a yield of at least about 50%. In some cases, the replacement may occur with a yield of at least about 50%, at least about 60%, at least about 70%, at least about 80%, at least about 90%, or, in some cases, at least about 95%. In some embodiments, the replacement may occur at a temperature of less than about 80° C., less than about 60° C., less than about 40° C., or, in some cases, less than about 25° C. In some embodiments, the replacement may occur at temperature below room temperature, for examples, less than about 20° C., less than about 10° C., less than about 0° C., less than about −10° C., less than about −20° C., less than about −30° C., less than about −40° C., less than about −50° C., or less. For example, the replacement of the nitrogen-containing ligand(s) with oxygen-containing ligand(s) may occur at room temperature. In some cases, the catalyst may be prepared by a relatively rapid reaction, with conversion of the catalyst precursor to the catalyst often occurring within 60 minutes or less, 30 minutes or less, or, in some cases, 15 minutes or less.

Upon formation of the catalyst in a reaction vessel, a one-pot procedure may be performed, wherein the catalyst may be generated in situ from a precatalyst and may be subsequently employed in a chemical reaction, in the same reaction vessel. Those of ordinary skill in the art would be able to select the appropriate catalyst in combination with the chemical reaction to be performed. The ability to, in a single reaction vessel, generate a catalyst in situ and utilize the catalyst in a reaction, may facilitate the ability to screen a large number of catalysts for a particular reaction in a relatively short period of time. Also, additional purification steps may be eliminated, which may be useful in cases where the catalyst may be difficult to isolate. In some embodiments, it may be advantageous to form and then isolate the catalyst, prior to using the catalyst in a chemical reaction.

In some cases, the reaction may be a carbon-carbon bond forming reaction. In some cases, the reaction may be a metathesis reaction (e.g., ring-opening cross-metathesis, ring-closing cross-metathesis, enyne metathesis, etc.). In some cases, the metathesis reaction may comprise polymerization of a monomeric species. For example, the metal complex may be useful in controlling the tacticity in polymer synthesis.

The catalyst may be provided in the reaction mixture in a sub-stoichiometric amount (e.g., catalytic amount). In certain embodiments, that amount is in the range of about 0.01 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 1 mol %, less than about 0.5 mol %, or less, relative to the limiting reagent. In the case where the molecular formula of the catalyst complex includes more than one metal, the amount of the catalyst complex used in the reaction may be adjusted accordingly.

The metal complexes (e.g., catalysts, catalyst precursors) which may be produced by methods of the present invention may undergo further reaction(s) to afford desired derivatives thereof. Such permissible derivatization reactions can be carried out in accordance with conventional procedures known in the art.

As suitable, the catalysts employed in the present invention may involve the use of metals which can mediate a particular desired chemical reaction. In general, any transition metal (e.g., having d electrons) may be used to form the catalyst, e.g., a metal selected from one of Groups 3-12 of the periodic table or from the lanthanide series. However, in some embodiments, the metal may be selected from Groups 3-8, or, in some cases, from Groups 4-7. In some embodiments, the metal may be selected from Group 6. According to the conventions used herein, the term "Group 6" refers to the transition metal group comprising chromium, molybdenum, and tungsten. In some cases, the metal is molybdenum or tungsten. Without wishing to be bound by theory, it may be expected that catalysts comprising different metal atoms from the same group and comprising similar ligands will perform similarly because they are known to undergo similar reactions, such as metathesis reactions. However, altering the ligand framework may affect the catalyst performance by, for example, modifying reactivity and preventing undesirable side reactions. In a particular embodiment, the catalyst comprises molybdenum. Additionally, the present invention may also include the formation of heterogeneous catalysts containing forms of these elements (e.g., by immobilizing a Mo complex on an insoluble substrate, for example, silica).

As used herein, the term "catalyst precursor" refers to a compound which may be converted to a final product (e.g., a catalyst) by one chemical reaction, such as deprotection, replacement of a ligand, and/or dissociation of a ligand from the catalyst precursor. For example, catalyst precursors of the invention may include metal complexes lacking a stereogenic metal center (e.g., an achiral metal complex), which may be reacted with a ligand to produce a metal complex comprising a stereogenic metal center.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In one embodiment, $R^4$ and $R^5$ may be pyrrolyl groups. In some embodiments, the nitrogen-containing ligand may be chiral and the precatalyst may be provided as a racemic mixture or a purified stereoisomer.

As used herein, the term "oxygen-containing ligand" may be used to refer to ligands comprising at least one oxygen atom. In some cases, the oxygen atom binds to the metal atom. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

In some cases, the oxygen-containing ligand may have a plane of symmetry, i.e., may be achiral. In some cases, the oxygen-containing ligand may lack a plane of symmetry, i.e., may be chiral, and may be provided as a racemic mixture or a purified stereoisomer. In some embodiments, the chiral, oxygen-containing ligand may be provided in at least about 80% optical purity, i.e., the oxygen-containing ligand sample contains about 90% of one enantiomer and about 10% of the other. In some embodiments, the chiral, oxygen-containing ligand may be at least about 90% optically pure, at least about 95% optically pure, or, in some cases, at least about 99% optically pure.

In some cases, the catalyst may comprise a monodentate, oxygen-containing ligand (e.g., an alkoxide) lacking a plane of symmetry such that, in conjunction with a stereogenic metal center, the combination of the monodentate, oxygen-containing ligand and the stereogenic metal center in part may confer shape specificity to a reaction site where the catalyst reacts with a reactant such as, for example, an olefin or an alkyne.

In some embodiment, the metal catalyst comprising a stereogenic metal center comprises a reaction site that is of sufficient shape specificity, defined in part by the monodentate, oxygen-containing ligand, other monodentate ligand, and/or M=N—$R^1$ site, to cause a molecular substrate having a plane of symmetry to react with a M=C center at the reaction site in a specific manner to produce a catalytic olefin metathesis product that is free of a plane of symmetry, i.e., is chiral. The product may be formed in at least about 50% enantiomeric excess. In some cases, the product may be formed in at least about 60%, at least about 70%, at least about 80%, at least about 90%, at least about 95%, at least about 98%, or, in some cases, 99% enantiomeric excess. In some cases, the enantiomeric excess may be calculated based on the stereogenic center formed during the reaction.

For example, in some cases, a reactant may comprise at least one stereogenic center and the product may comprise at least two stereogenic centers, i.e., including any stereogenic center(s) present prior to the reaction and any stereogenic center(s) formed during the reaction. While the products comprising more than one stereogenic center may comprise diastereomers, the enantiomeric excess of the product may be calculated based on the enantiomeric excess of a particular stereogenic center formed during the reaction. In some cases, the stereogenic metal center comprises a reaction site that is of sufficient shape specificity to produce, upon reaction, at least one double bond having a high Z:E ratio. In some embodiments, the Z:E ratio may be at least about 1:10, at least about 1:5, or at least about 1:2. In some embodiments, the Z:E ratio may be at least about 1:1, at least about 2:1, at least about 5:1, at least about 10:1, at least about 20:1, at least about 40:1, at least about 50:1, or greater.

A method to screen for monodentate, oxygen-containing ligands having sufficient shape specificity to produce a stereogenic product (e.g., high e.e., or high Z:E ratio) can involve providing a first solution comprising the catalyst and a second solution comprising the reactants. The solution(s) may comprise solvents which are compatible with the desired analysis (e.g., deuterated solvents for NMR techniques, polar/non-polar solvents for HPLC, GLC techniques, etc.). The first solution and the second solution may be combined under the appropriate conditions (e.g., temperature, time, agitation, etc.), and, after an appropriate reaction time has elapsed, the resulting solution may be analyzed using various methods known in the art. In some cases, the solution may be filtered prior to analysis. For analysis of Z:E ratio, yield, and/or enantiomeric excess, the product may be analyzed by NMR (e.g., $^1$H NMR, $^{13}$C NMR, etc.), HPLC, GLC, or the like. In some cases, more than one analysis may be performed. For example, a product may be analyzed by NMR, wherein the presence of different enantiomers may be indicated by NMR peaks characteristic of a particular enantiomer upon addition of a chiral shift reagent. In some embodiments, the product may be analyzed using chromatography (e.g., HPLC or GLC), where different enantiomers or diastereomers may exhibit distinct retention times. Those of ordinary skill in the art will be able to determine the appropriate method, or combination of methods, to utilize based upon the product to be analyzed.

In some embodiments, the shape specificity, imparted by a monodentate, oxygen-containing ligand and/or stereogenic metal center may be sufficient to allow a mixture of two enantiomeric reactants (e.g., olefins) to react with an M=C center of the reaction site at different rates. That is, a catalyst may be designed to have shape specificity sufficient to differentiate between enantiomers of a reactant by sterically interacting with one enantiomer almost exclusively or exclusively to achieve enantiomeric selectivity, that is, a preference for one enantiomer over the other. Enantiomeric selectivity by kinetic resolution involves reducing the steric interactions in the transition state of the reaction of the substrate at the catalyst such that the transition state involving one enantiomer is of lower energy than the transition state of the other enantiomer. In some cases, the term shape specificity refers to the shape of an M=C reaction site in the transition state, as formed by the surrounding ligands, such that upon reaction of the substrate with the metal compound, one enantiomer "fits into" the binding site with less steric interaction than the other enantiomer. The transition state energy is lower for the enantiomer with a better "fit" or shape specificity over the other.

Catalysts and catalyst precursors of the invention may comprise substituted imido groups (e.g., N—$R^1$). Without wishing to be bound by theory, the imido group may stabilize the organometallic compositions described herein by providing steric protection and/or reducing the potential for bimolecular decomposition. In some cases, $R^1$ may be selected to be sterically large or bulky, including phenyl groups, substituted phenyl groups (e.g., 2,6-disubstituted phenyls, 2,4,6-trisubstituted phenyls), polycyclic groups (e.g., adamantyl), or other sterically large groups. In some embodiments, $R^1$ may be 2,6-dialkylphenyl, such as 2,6-diisopropylphenyl. Catalysts and catalyst precursors of the invention may further comprise substituted alkylidene groups. The alkylidene groups may be mono-substituted or di-substituted with, for example, alkyl, heteroalkyl, aryl, or heteroaryl groups, optionally substituted. In some cases, the alkylidene may be mono-substituted with, for example, t-butyl, dimethylphenyl, or the like.

The combination of imido, alkoxide, and/or alkylidene ligands may be selected to suit a particular application. For example, in some cases, sterically large or sterically bulky ligands and/or ligand substituents may impart a higher degree of stability to a catalyst, while, in some cases, lowering the reactivity of the catalyst. In some cases, smaller ligands and/or substituents may generate more reactive catalysts that may have decreased stability. Those of ordinary skill in the art would be able to balance such factors and select the appropriate combination of ligands for catalysts of the invention.

In some cases, the methods described herein may be performed in the absence of solvent (e.g., neat). In some cases, the methods may comprise one or more solvents. Examples of solvents that may be suitable for use in the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like. In some embodiments, the solvent may be benzene, toluene, pentane, methylene chloride, or THF. In a particular embodiment, the solvent is benzene.

As used herein, the term "reacting" refers to the formation of a bond between two or more components to produce a compound. In some cases, the compound is isolated. In some cases, the compound is not isolated and is formed in situ. For example, a first component and a second component may react to form one reaction product comprising the first component and the second component joined by a covalent bond (e.g., a bond formed between a ligand and a metal, or a bond formed between two substrates in a metathesis reaction). That is, the term "reacting" does not refer to the interaction of solvents, catalysts, bases, ligands, or other materials which may serve to promote the occurrence of the reaction with the component(s).

As used herein, the term "organic group" refers to any group comprising at least one carbon-carbon bond and/or carbon-hydrogen bond. For example, organic groups include alkyl groups, aryl groups, acyl groups, and the like. In some cases, the organic group may comprise one or more heteroatoms, such as heteroalkyl or heteroaryl groups. The organic group may also include organometallic groups. Examples of groups that are not organic groups include —NO or —$N_2$. The organic groups may be optionally substituted, as described below.

The term "organometallic" is given its ordinary meaning in the art and refers to compositions comprising at least one metal atom bound to one or more than one organic ligand. In some cases, an organometallic compound may comprise a metal atom bound to at least one carbon atom.

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, $2^{nd}$ ed.; Wiley: New York, 1991).

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_1$-$C_{10}$ for straight chain lower alkyls).

The term "heteroalkyl" is given its ordinary meaning in the art and refers to alkyl groups as described herein in which one or more atoms is a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" is given its ordinary meaning in the art and refers to single-ring aromatic groups such as, for example, 5-, 6- and 7-membered single-ring aromatic groups. The term "heteroaryl" is given its ordinary meaning in the art and refers to aryl groups as described herein in which one or more atoms is a heteroatom (e.g., oxygen, nitrogen, sulfur, and the like). Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least on functional group that has sufficient ionic character to coordinate the metal center, such as a biphenolate group, for example.

The term "olefin," as used herein, refers to any species having at least one ethylenic double bond such as normal and branched chain aliphatic olefins, cycloaliphatic olefins, aryl substituted olefins and the like.

The term "cyclic olefin," as used herein, refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, a bicyclo compound, an oxabicyclo compound, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "halogen" or "halide" designates —F, —Cl, —Br, or —I.

The term "alkoxy" refers to the group, —O-alkyl.

The term "aryloxy" refers to the group, —O-aryl.

The term "acyloxy" refers to the group, —O-acyl.

The term "arylalkyl", as used herein, refers to an alkyl group substituted with an aryl group.

The terms "amine" and "amino" are art-recognized and refer to both unsubstituted and substituted amines, e.g., a moiety that can be represented by the general formula: N(R')(R'')(R''') wherein R', R'', and R''' each independently represent a group permitted by the rules of valence.

The term "dialkyl amine" is art-recognized and can be represented by the general formula: N(R')(R'')⁻, wherein R' and R'' are alkyl groups.

An "alkoxide" ligand herein refers to a ligand prepared from an alcohol, in that removing the hydroxyl proton from an alcohol results in a negatively charged alkoxide.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For example, a substituted alkyl group may be $CF_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

EXAMPLES

Example 1

The following example describes non-limiting examples of the stereoselective synthesis of stereogenic metal complexes.

Examination revealed reaction of mono-TBS-protected BINOL 23, substituted at the 3 and 3' positions with Br, with one equivalent of Mo bis(pyrrolide) 22a-b led to the clean formation of monoalkoxide complex 27a-b (Table 1). Mo bis(pyrrolide) may be synthesized according to procedures known to those of ordinary skill in the art, for example, according to the scheme shown in FIG. 21. Monoalkoxide 27a, containing a stereogenic Mo center, was formed in a 19:1 d.r. (entry 1, Table 1). Use of Mo bis(pyrrolide) 22b led to the formation of Mo monoalkoxide 27b with 7:1 diastereoselectivity (entry 2, Table 1).

TABLE 1

Stereoselective synthesis of stereogenic Mo-based complexes.

| Entry | Alcohol | Mo Bis(pyrrolide) | Product | Temp (° C.) | conv (%)[a,b] | d.r.[a,c] |
|---|---|---|---|---|---|---|
| 1 | | 22a | 27a | 22 | >98 | 19:1 |
| 2 | | 22b | 27b | 22 | >98 | 7:1 |

TABLE 1-continued

Stereoselective synthesis of stereogenic Mo-based complexes.

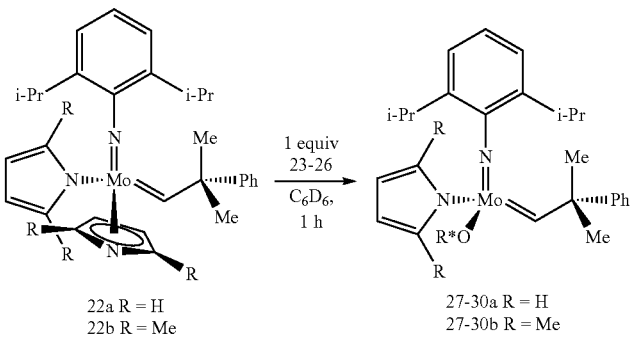

22a R = H
22b R = Me 27-30a R = H
27-30b R = Me

| Entry | Alcohol | Mo Bis(pyrrolide) | Product | Temp (° C.) | conv (%)[a,b] | d.r.[a,c] |
|---|---|---|---|---|---|---|
| 3 | 24 | 22a | 28a | 22 | >98 | >20:1 |
| 4 |  | 22b | 28b | 22 | 90 | 7:1 |
| 5 |  | 22b | 28b | 60 | >98 | 6:1 |
| 6 | 25 | 22a | 29a | 22 | >98 | >20:1 |
| 7 |  | 22b | 29b | 22 | 25 | 3:1 |
| 8 |  | 22b | 29b | 60 | 75 | 3:1 |
| 9 | 26 | 22a | 30a | 22 | >98 | >20:1 |
| 10 |  | 22b | 30b | 22 | >98 | 5:1 |

In Table 1:
[a]Measured by 400 MHz $^1$H NMR;
[b]Conversion was based on consumption of Mo bis(pyrrolide) 22a-b;
[c]The diastereomeric ratio (d.r.) reported is that of the two major syn-alkylidene isomers although, in some cases, anti-alkylidenes were also formed, usually comprising <5% of the reaction mixture.

Figure 22:
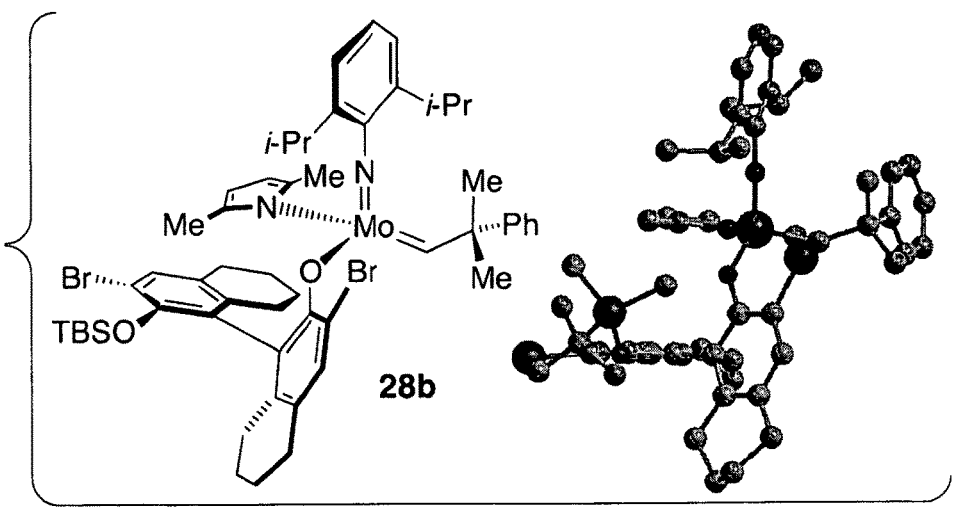
FIG. 22 shows a crystal structure of a Mo-complex, according to one embodiment of the invention.

Attempts to prepare the mono-aryloxides with the parent ligand lacking the bromides led to a mixture containing bis-aryloxides as well as the unreacted bis-pyrrolides. Synthesis of such complexes may be accomplished with one equivalent of the related octahydrobinaphthol, but the process may be less stereoselective (e.g., 1-2.5:1 d.r.) and, unlike the bromides, excess alcohol may cause the bis-aryloxide formation. In reactions to form 22a-22b, bis-aryloxides were not detected even under relatively forcing conditions (60° C., 2 h). The bromine atoms may be required, in some embodiments, for efficient and stereoselective formation of 27-28 (e.g., to minimize formation of bis-aryloxides). Complexes derived from H$_8$-BINOL were also examined (entries 3-10, Table 1). The dihedral angle of the biaryl linkage is different from BINOL to H$_8$-BINOL compounds and may affect the stereoselectivity of the substitution. Alcohol 24 allowed for the clean formation of monoalkoxides 28a-b (entries 3-4, Table 1). With alcohol 24, complex 28a (entry 3, Table 1) was formed in a >20:1 d.r. (compare to entry 1). Complex 28b was generated in a 7:1 d.r. at 22° C., but only proceeded to 90% conversion in 1 h (entry 4, Table 1). Heating to 60° C. led to complete conversion within 1 h with only a moderate loss in stereoselectivity (entry 5, Table 1). Although complex 28b was generated as a mixture of diastereomers in situ, the major diastereomer may be isolated upon simple recrystallization from pentane. A crystal structure of this diastereomer is shown in FIG. 22.

In some embodiments, modification of the alcohol protecting group may influence the diastereoselectivity of the substitution. For example, whereas 29a was obtained in >20:1 diastereoselectivity in the presence of alcohol 25 (entry 6, Table 1), 29b was generated in a diminished 3:1 selectivity (entries 7-8, Table 1). Formation of the monoalkoxide complex was slower, proceeding to only 25% conversion in 1 h at 22° C. (entry 7, Table 1) and 75% conversion in 1 h at 60° C. (entry 8, Table 1). Although the reaction was slow, there was no difference in the diastereomeric purity of the product formed at 22° C. and 60° C.

Variation at the 3 and 3' positions of the BINOL ligand, in some embodiments, may also affect the diastereoselectivity of the substitution. For example, dichloro alcohol 26 furnished monoalkoxide 30a in a >20:1 d.r. (entry 9, Table 1); complete conversion was achieved in 1 h at 22° C. Monoalkoxide complex 30b was formed cleanly in 1 h at 22° C. (5:1 d.r., entry 10, Table 1).

Example 2

The following example describes the stereoselective synthesis of additional metal complexes comprising a stereogenic metal atom.

A number of other alcohol ligands were also screened, and the results are shown in Table 2. TBS-protected BINOL 31 (Table 2), bearing methyl substituents at the 3 and 3' positions, led to the formation of monoalkoxide complex 34a in a 5:1 d.r. (entry 1, Table 2). Monoalkoxide complex 34b was formed in a 3:1 d.r. (entry 2, Table 2). With pentafluorophenyl substituents at the 3 and 3' positions, alcohol 32 generated monoalkoxide complex 35a in a 4.5:1 d.r. (entry 3, Table 2); however, the reaction of alcohol 32 with Mo bis(pyrrolide) 22b proceeded to <2% cony, even at 60° C. (entry 4, Table 2). It is interesting to note that with larger alkyl substituents at the 3 and 3' positions, the diastereoselectivity in the formation of the monoalkoxide complex was lower than with halides at these positions in these embodiments. Finally, alcohol 33, a monoprotected biphenol, was tested in the substitution. At 22° C., 36a was formed in a >20:1 d.r., but the reaction only proceeded to 19% conversion in 1 h (entry 5, Table 2). At 60° C., the reaction was complete within 1 h and 36a was generated exclusively in a 17:1 d.r. (entry 6, Table 2). When reacted with Mo bis(pyrrolide) 22b, alcohol 33 failed to deliver any desired product, even at 60° C. (entry 7, Table 2).

TABLE 2

Stereoselective synthesis of stereogenic Mo-based complexes.

| Entry | Alcohol | Mo Bis(pyrrolide) | Product | Temp (° C.) | conv (%)[a,b] | d.r.[a,c] |
|---|---|---|---|---|---|---|
| 1 | 31 | 22a | 34a | 22 | >98 | 5:1 |
| 2 | | 22b | 34b | 22 | >98 | 3:1 |

TABLE 2-continued

Stereoselective synthesis of stereogenic Mo-based complexes.

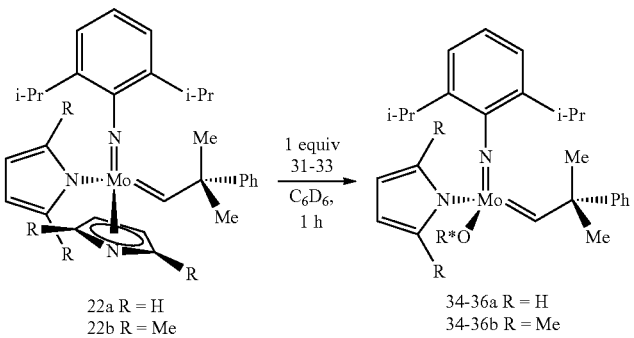

22a R = H
22b R = Me 34-36a R = H
34-36b R = Me

| Entry | Alcohol | Mo Bis(pyrrolide) | Product | Temp (° C.) | conv (%)[a,b] | d.r.[a,c] |
|---|---|---|---|---|---|---|
| 3 | 32 (C₆F₅, OTBS, OH, C₆F₅) | 22a | 35a | 22 | >98 | 4.5:1 |
| 4 |  | 22b | 35b | 60 | <2 | — |
| 5 | 33 (Me, t-Bu, Me, OTBS, Me, OH, Me, t-Bu) | 22a | 36a | 22 | 19 | >20:1 |
| 6 |  | 22a | 36a | 60 | >98 | 17:1 |
| 7 |  | 22b | 36b | 60 | <2 | — |

In Table 2:
[a]Measured by 400 MHz ¹H NMR;
[b]Conversion was based on consumption of Mo bis(pyrrolide) 22a-b;
[c]The ratio reported is that of the two major syn-alkylidene isomers although, in some cases, anti-alkylidenes were also formed, usually comprising <5% of the reaction mixture.

Example 3

Figure 23:
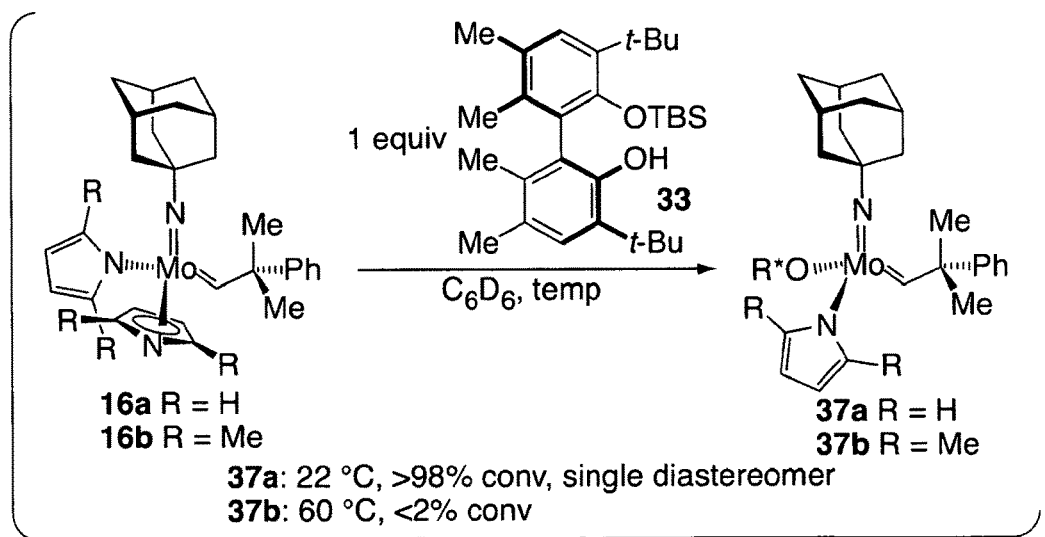
FIG. 23 shows the synthesis of Mo-complexes, according to some embodiments of the invention.

Sterically demanding alcohol 33 was tested in the substitution of Mo bis(pyrrolide) 16a-b (FIG. 23), which carries a smaller 1-adamantylimido ligand. Unlike with smaller alcohols, such as 23, 33 reacts with Mo bis(pyrrolide) 16a to furnish monoalkoxide complex 37a exclusively (bis(aryloxide) is not formed). Moreover, complex 37a was generated as a single diastereomer (FIG. 23). 37b was not formed from Mo bis(pyrrolide) 16b, even at 60° C.

Example 4

The following example describes the use of complexes synthesized in Examples 1-3 in metathesis reactions to determine their catalytic activity as well as their ability to provide stereospecific products (e.g., high e.e., high Z:E ratio). To test this, the asymmetric ring-closing metathesis (ARCM) of prochiral triene 38 to furnish tetrahydropyridine 39 was examined (Table 3).

Without wishing to be bound by theory, the following points may be noted: (1) in most cases examined in this Example, complexes bearing a dimethylpyrrolide ligand, in comparison to those bearing an unsubstituted pyrrolide ligand, are more reactive (compare entries 3 and 4, 5 and 6, Table 3) and are, in general, more enantioselective (e.g. complex 28a delivers 39 in 13% e.e. (entry 3), whereas 28b delivers the product in 93% e.e. (entry 4)); (2) chiral ligands with large substituents at the 3 and 3' positions, in this Example, form less reactive and often less selective catalysts for this ARCM (entry 9).

TABLE 3
Examining the reactivity of chiral-at-Mo monoalkoxide complexes.
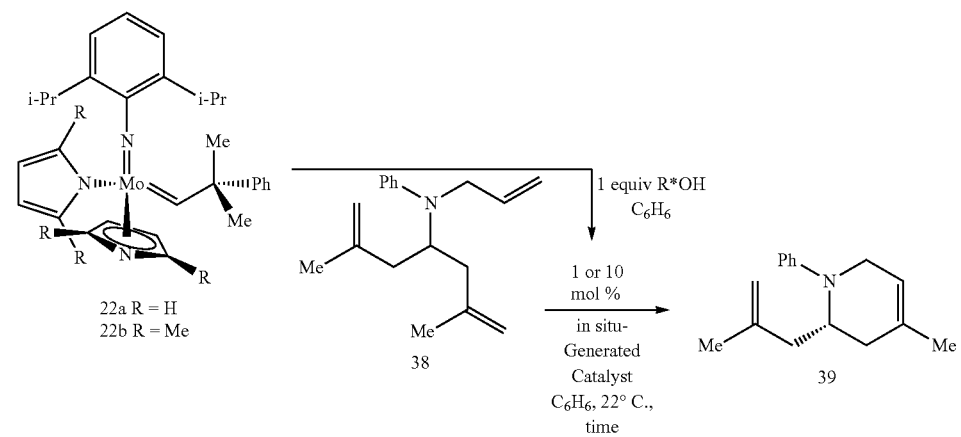
| Entry | Alcohol | Mo Bis-(pyrrolide) | Complex | Cat Loading (mol %) | Time (h) | Conv (%)$^{a,b}$ | Yield (%)$^c$ | ee (%)$^d$ |
|---|---|---|---|---|---|---|---|---|
| 1 | 23 | 22a | 27a | 10 | 12$^e$ | >98 | 84 | 18 |
| 2 | | 22b | 27b | 10 | 12$^e$ | >98 | 81 | 51 |
| 3 | 24 | 22a | 28a | 1 | 0.5 | 54 | 47 | 13 |
| 4 | | 22b | 28b | 1 | 0.5 | >98 | 90 | 93 |
| 5 | 25 | 22a | 29a | 1 | 0.5 | 42 | 36 | 16 |
| 6 | | 22b | 29b | 1 | 0.5 | >98 | 83 | 86 |
| 7 | 26 | 22b | 30b | 1 | 0.5 | >98 | 98 | 93 |

TABLE 3-continued

Examining the reactivity of chiral-at-Mo monoalkoxide complexes.

| Entry | Alcohol | Mo Bis-(pyrrolide) | Complex | Cat Loading (mol %) | Time (h) | Conv (%)$^{a,b}$ | Yield (%)$^{c}$ | ee (%)$^{d}$ |
|---|---|---|---|---|---|---|---|---|
| 8 | 32 | 22a | 35a | 10 | 1 | >98 | nd | 48 |
| 9 | 33 | 22a | 36a | 10 | 1 | 53 | nd | 5 |

In Table 3:
$^{a}$Determined by 400 MHz $^{1}$H NMR analysis of the crude reaction mixture;
$^{b}$Based on consumption of substrate;
$^{c}$Isolated yield after purification;
$^{d}$Determined by GLC analysis;
$^{e}$A 12 h reaction time was probably not necessary for >98% conversion.

Example 5

The following example describes the use of these complexes in metathesis reactions.

Figure 21:
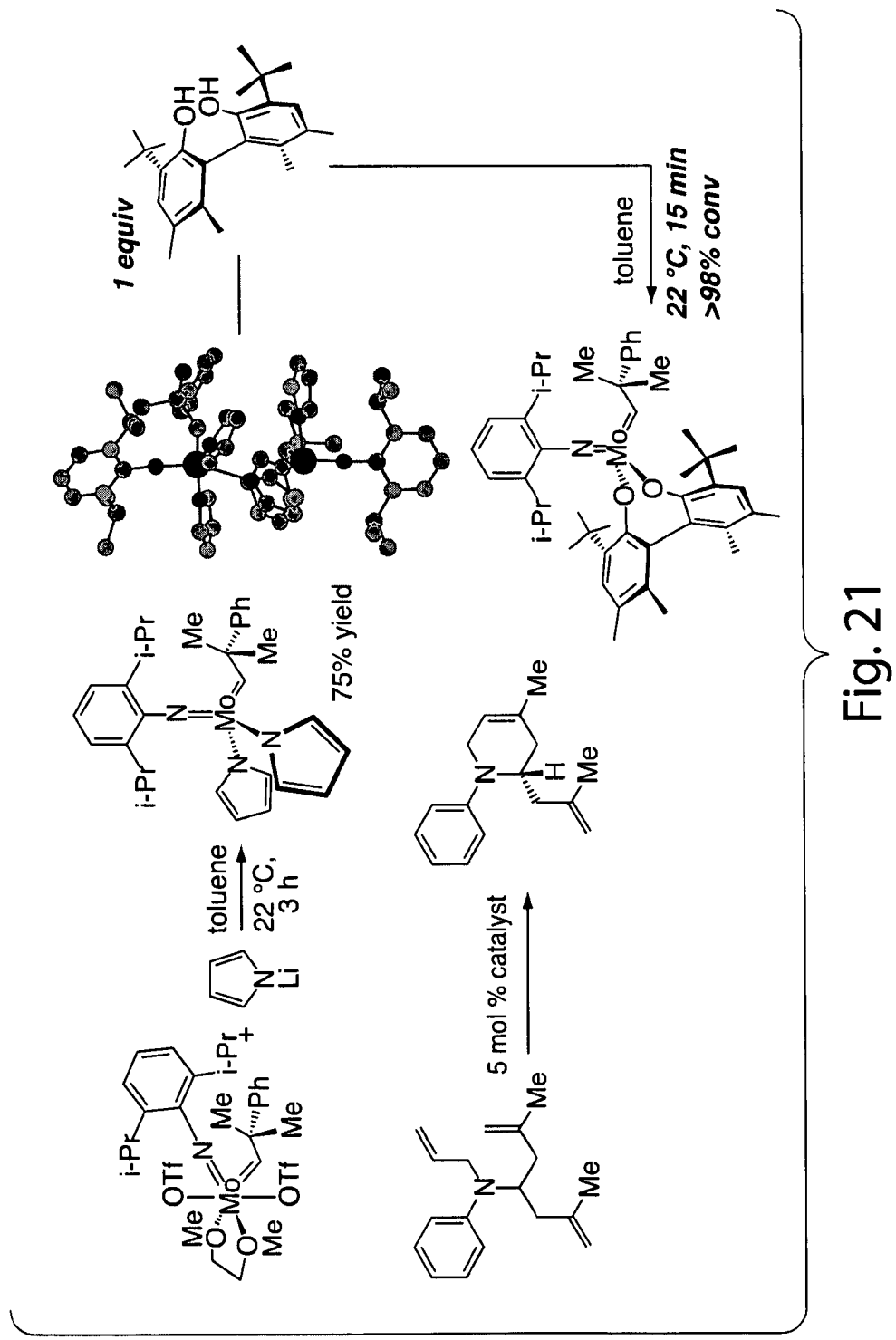
FIG. 21 shows the synthesis of Mo-complexes, according to some embodiments of the invention.

Metal complexes comprising mono-aryloxides were used as catalysts for enantioselective ring-closing metathesis (RCM). The transformation in Table 4 (38 into 39) served as the model process; reactions were performed with complexes prepared and used in situ. With 1 mol % of 27a (d.r.=19:1; entry 1, Table 4), ARCM proceeds to 50% conversion, affording R-39 in 18% enantiomeric excess (e.e.). With 27b (d.r.=7:1; entry 2, Table 4), complete conversion is achieved and S-39 is obtained in 50% e.e. The above trend is again observed in reactions involving 28a-28b (entries 3-4, Table 4) but with a wider selectivity gap: with 1 mol % 28a, ARCM proceeds to 54% conversion to afford R-39 in 13% e.e., whereas in the presence of 28b, there is >98% conversion and S-39 is isolated in 93% e.e. With 28b, enantioselective RCM can be performed in a fume hood at 22° C. with 1 mol % loading (30 minutes, 96% conv, 86% yield, 92% e.e.). Such findings illustrate the potential of the catalysts described herein in practical procedures for stereoselective synthesis. Despite providing slightly lower selectivity in this Example, 28b is more effective than the corresponding optimal Mo diolate (5 mol % 62a: 95% conv, 20 minutes, 98% e.e.). FIG. 21 shows a non-limiting example of the synthesis and/or generation of compound 62a. The reactions in this example were carried out in purified benzene or toluene under an atmosphere of nitrogen gas

TABLE 4

Examination of chiral Mo aryloxide complexes as catalysts for enantioselective ring-closing metathesis.

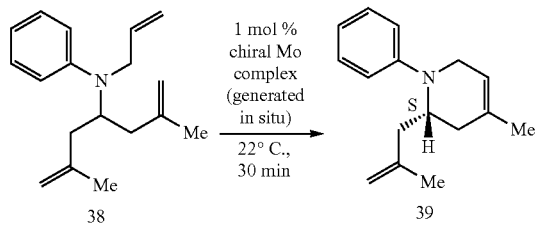

| Entry no | Chiral Complex | Conv. (%)§; Yield (%)§§ | e.r.† | e.e. (%)‡; Config.⁺ |
|---|---|---|---|---|
| 1 | 27a | 50; n.d. | 41:59 | 18; R |
| 2 | 27b | >98; 91 | 75:25 | 50; S |
| 3 | 28a | 54; n.d. | 43.5:56.5 | 13; R |
| 4 | 28b | >98; 91 | 96.5:3.5 | 93; S |

In Table 4:
(§) Conversion measured by analysis of 400 MHz ¹H NMR spectra of unpurified mixtures;
(§§) Yield of isolated product after purification;
(†) The enantiomer ratio (e.r.) was determined by gas liquid chromatography (GLC) analysis;
(‡) The enantiomeric excess (e.e.) was calculated from the e.r.; the variance of e.e. values are estimated to be <±2%;
(+) Configuration of the major enantiomer;
n.d. = not determined.

The reduced reactivity and selectivity in reactions of complexes that were more stereochemically pure (i.e., 27a and 28a), relative to other complexes used in this Example, indicated that the minor diastereomers might exhibit higher activity. To shed light on this issue, a stereochemically pure sample of 28b (d.r.=>25:1) was used to initiate RCM of 38 (1 mol %, 22° C., 30 min), and S-39 was isolated in 93% e.e. and 94% yield, results which were identical to those obtained with the 7:1 mixture (entry 4, Table 4). Moreover, by monitoring the reaction progress spectroscopically (400 MHz ¹H NMR) in the presence of in situ generated 28b, it was established that >98% of the major isomer was consumed, presumably through initiation with the olefin substrate, while the minor diastereomer remains largely intact (>95%).

Example 6

The exceptional reactivity of catalyst 28b is demonstrated in Table 5. In the presence of 2 mol % catalyst 28b (C₆H₆, 0.1 M), triene 38 may be converted to 39 (20 min, 95% conv) in 92% e.e.; in 10 min only 70% conv was observed. With 1 mol % (entry 3, Table 5) the reaction proceeded to >98% in 30 min, and with the same enantioselectivity (91% e.e.). Conducting the reaction essentially neat, using only the solvent required to form the in situ generated catalyst (reaction concentration=4.0 M), 0.5 mol % catalyst was sufficient (15 min, >98% conv, 93% e.e.). To put these results into perspective, the optimal diolate-based catalyst 19a, generated 39 in the absence of solvent (2.5 mol %, neat, 10 min, >98% conv) in 78% yield and >98% e.e. Diastereomerically pure isolated catalyst 28b produced the same result as in situ-generated catalyst (entry 5, Table 5).

TABLE 5

Optimization of ARCM reaction of 38 with catalyst 28b.

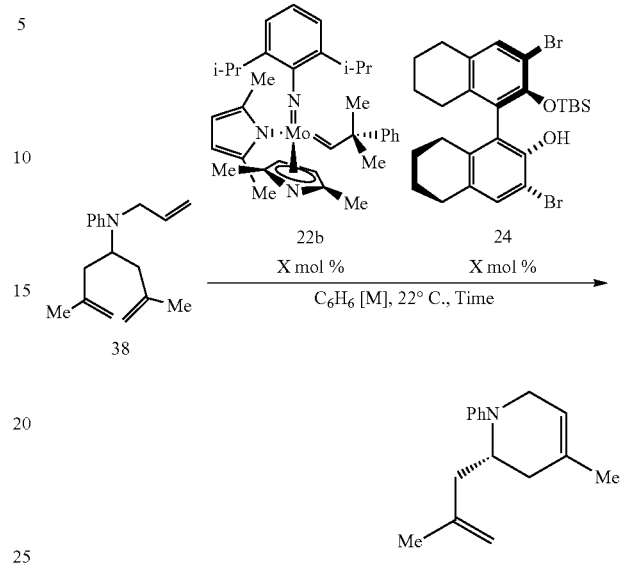

| entry | catalyst loading | Concentration | Time | Conv.ᵃ | % eeᵇ |
|---|---|---|---|---|---|
| 1 | 2 mol % | 0.1 M | 10 min | 70 | 91 |
| 2 | 2 mol % | 0.1 M | 20 min | 95 | 92 |
| 3 | 1 mol % | 0.1 M | 30 min | >98 | 91 |
| 4 | 0.5 mol % | 4.0 M | 15 min | >98ᶜ | 93 |
| 5ᵈ | 1 mol % | 0.1 M | 30 min | >98 | 93 |

ᵃDetermine by ¹H NMR (400 MHz) analysis of the crude reaction mixture.
ᵇDetermined by chiral GC or HPLC.
ᶜ90% isolated yield.
ᵈIsolated diastereomerically pure 28b was used.

Example 7

Catalytic enantioselective synthesis of unsaturated medium-ring amines can also be achieved. As depicted in Table 6 (entry 2), chiral in situ-generated catalyst promoted the formation of seven-membered ring amine 41 (2 mol %, 1 h, >98% conv) in 76% yield and 85% e.e. Notably, using dichloro alcohol 26, catalyst loadings may be lowered to 1 mol % (>98% conv, 1 h), however, enantioselectivity decreased to 70% e.e. (entry 3, Table 6).

Figure 24:
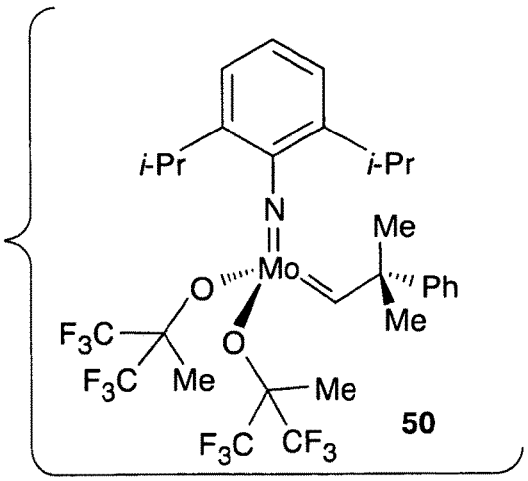
FIG. 24 shows a metathesis catalyst which does not comprise a stereogenic metal center.

Mo-catalyzed ARCM of unprotected secondary amines has proven to be a difficult transformation, positioning a neighboring quaternary center adjacent to the free amine or protecting the free amine as a catechol borane has enabled successful ARCM to proceed in moderate to good enantioselectivity. As shown in Table 6 (entry 4), 5 mol % of the dibromo alcohol 24 and Mo-Bis(pyrrolide) 22b, efficiently promoted ARCM of secondary amine 42 (1 h, >98% conv, 49% yield, 67% e.e.). Chiral diolate catalysts failed to promote this transformation and 5 mol % achiral 50 (FIG. 24) only proceeded to 75% conversion in 12 h. In addition to secondary amine 42, cyclic tertiary amines 44 and 46 proved to be difficult ring closures with current Mo diolates (44: 15 mol % 19b, 24 h, 75% conv, 30% e.e.; 46: 5 mol % 19b, 20 h, >98% conv, 40% e.e.). As illustrated in entry 5, six-membered bicyclic amine 45 was afforded in high yield (93%) and enantioselectivity (90% e.e.), with 1 mol % catalyst in 1 h. In addition, seven-membered bicyclic amines may be generated (entries 6-7, Table 6). Changing the alcohol to dichloro analogue 26, the reaction proceeded to 94% conversion and 76% e.e. This is a second data point, which shows the dichloro ligand 26 was more reactive than dibromo 24, in some embodiments. Amide 48 (entry 8, Table 6), in contrast to previously reported results (10 mol % 20, 48 h, >98% e.e.), also cyclized efficiently (5 mol %, 30 min, 91% conv, 84% yield, 92% e.e.).

TABLE 6

ARCM of Amines and Amides with In-Situ Generated Catalysts.

| entry | Substrate | Mo-Bispyrrolide/ Alcohol[a] | catalyst Loading | Time | Product | Conv.[b] | Yield(%)[c] | % ee[d] |
|---|---|---|---|---|---|---|---|---|
| 1 | 38 | 22b/24<br>19a | 1 mol %<br>5 mol % | 30 min<br>20 min | 39 | >98%<br>>98 | 90<br>78 | 93<br>>98 |
| 2<br>3 | 40 | 22b/24<br>22b/26<br>19a | 2 mol %<br>1 mol %<br>2 mol % | 1 h<br>1 h<br>7 h | 41 | >98%<br>>98%<br>>95% | 76<br>75<br>90 | 85<br>70<br>95 |
| 4 | 42 | 22b/24<br><2% conv w/ chiral diolates 50 (achiral) | 5 mol % | 1 h<br>12 h | 43 | >98%<br>76%[25] | 49<br>nd | 67 |
| 5 | 44 | 22b/24<br>19b | 1 mol %<br>15 mol % | 1 h<br>24 h | 45 | 98%<br>75% | 93<br>nd | 90<br>30 |
| 6<br>7 | 46 | 22b/24<br>22b/26<br>19b | 5 mol %<br>5 mol %<br>5 mol % | 1 h<br>1 h<br>20 h | 47 | 85%<br>94%<br>>98% | 85<br>73<br>nd | 69<br>76<br>40 |

TABLE 6-continued

ARCM of Amines and Amides with In-Situ Generated Catalysts.

| entry | Substrate | Mo-Bispyrrolide/ Alcohol[a] | catalyst Loading | Time | Product | Conv.[b] | Yield(%)[c] | % ee[d] |
|---|---|---|---|---|---|---|---|---|
| 8 | 48 | 22b/24<br>20 | 5 mol %<br>10 mol % | 30 min<br>48 h | 49 | 91% | 84<br>91 | 92<br>>98 |

[a]Conditions: The catalyst is generated in situ as a 0.02M solution in $C_6H_6$ for 1 h, and then added to a solution of substrate in $C_6H_6$ (overall concentration 0.1M).
[b]Determined by $^1$H NMR (400 MHz) analysis of the crude reaction mixture.
[c]Isolated yield after purification.
[d]Determined by chiral HPLC or GLC analysis

Example 8

The results in Table 6 demonstrate that oxygen-containing substrates worked well with catalyst 28b, in some embodiments. Ether substrate 51 (entry 1), underwent efficient ARCM (1 mol %, 30 min, >98% cony, 60% e.e.). Triene 53, containing a quaternary ether, efficiently cyclized in up to 65% e.e. (entries 2-3).

Figure 8:
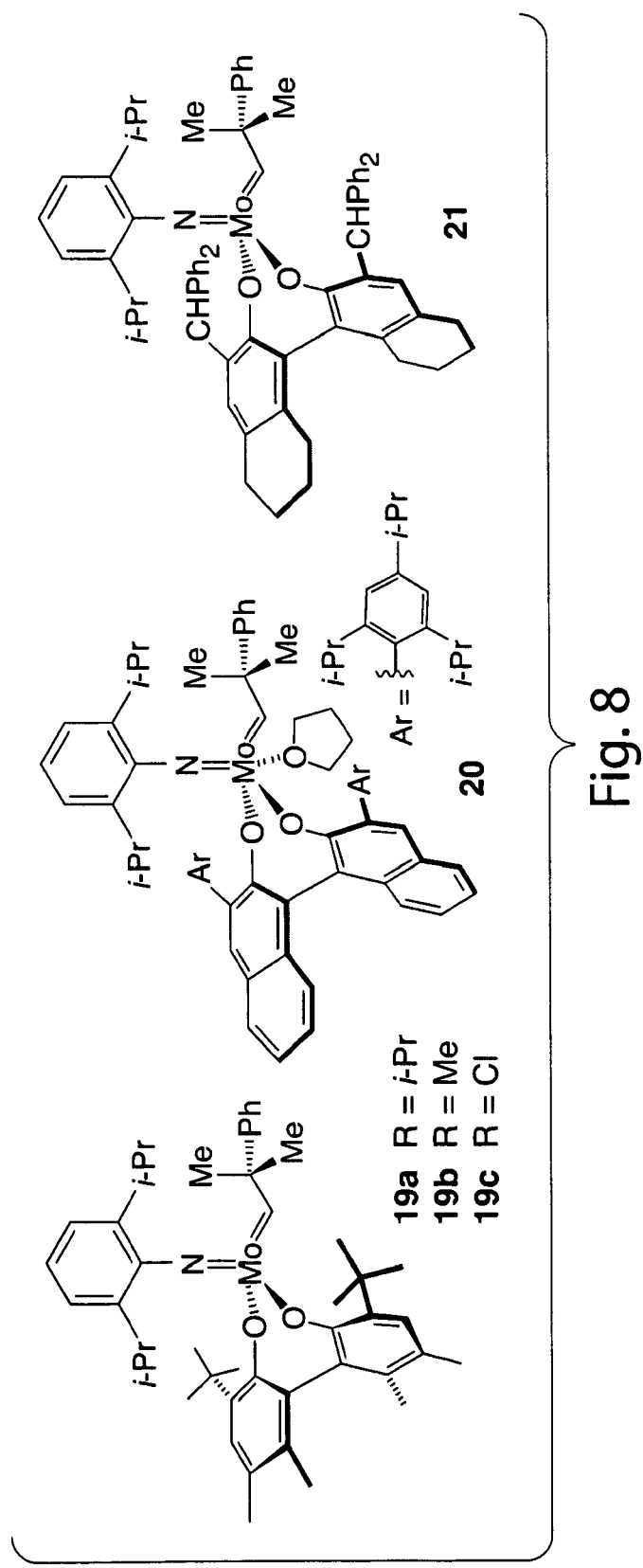
FIG. 8 shows examples of chiral Mo-complexes derived from BINOL or a chiral biphenol.
Figure 9A:
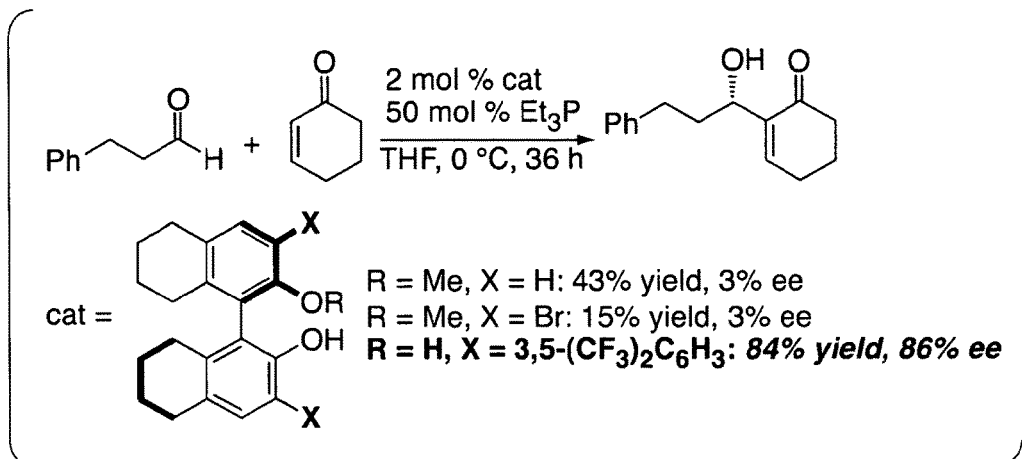
FIG. 9A shows a non-limiting example of a metathesis reaction.
Figure 9B:
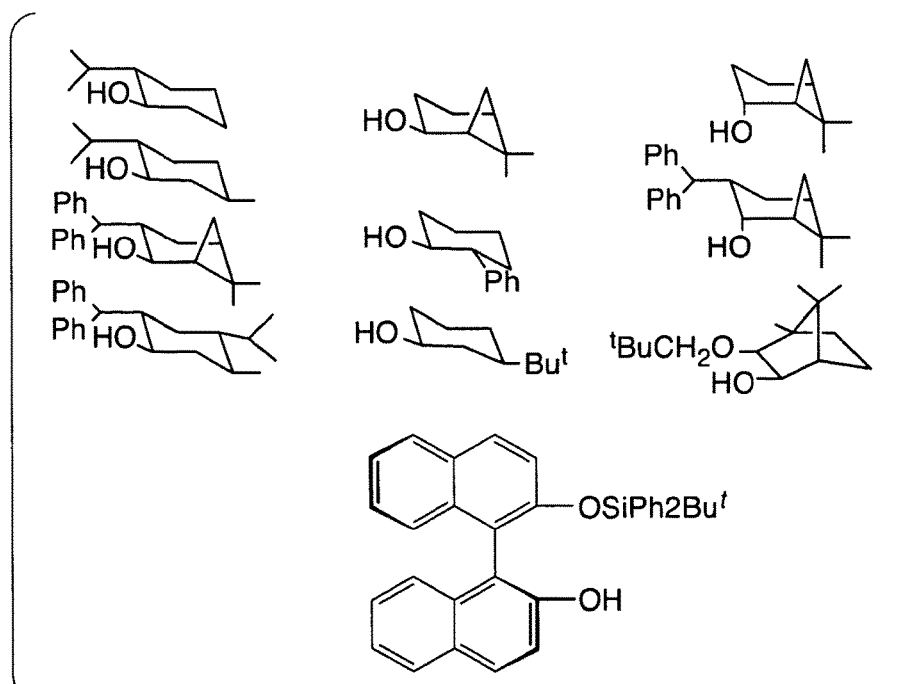
FIG. 9B shows examples of monodentate alcohols useful in the synthesis of organometallic compounds.

As depicted in entry 4 (Table 6), ARCM of allylsilane 55 (1 mol %, 1 h) generates cyclic silane 56 in good yield and enantioselectivity (>98% cony, 79% yield, 86% e.e.). Electronically different, enol ether 57 (entry 5, Table 7) cyclized with 10 mol % catalyst in 1 h to deliver dihydropyran 58 in 95% yield and in 37% e.e. The enantioselectivity was modest but the most active Mo diolate catalyst for this transformation (20, FIG. 8), required 15 mol % and 18 h (91% cony, 91% yield, 83% e.e.).

TABLE 7

ARCM of ether substrates with in-situ generated catalyst.

| entry | Substrate | Mo-Bis-pyrrolide/ Alcohol[a] | catalyst Loading | Time | Product | Conv.[b] | Yield (%)[c] | % ee[d] |
|---|---|---|---|---|---|---|---|---|
| 1 | 51 | 22b/24<br>19a | 1 mol %<br>5 mol % | 30 min<br>6 h<br>(60° C.) | 52 (volatile) | >98% | nd<br>80 | 60<br>84[26] |
| 2<br>3 | 53 | 22b/24<br>22b/26 | 1 mol %<br>1 mol % | 30 min<br>30 min | 54 | >98%<br>>98% | 85<br>98 | 65<br>49 |
| 4 | 55 | 22b/24<br>19c | 1 mol %<br>5 mol % | 1 h<br>12 h | 56 | >98%<br>>98% | 79<br>98 | 86<br>94[27] |

TABLE 7-continued

ARCM of ether substrates with in-situ generated catalyst.

| entry | Substrate | Mo-Bis-pyrrolide/ Alcohol[a] | catalyst Loading | Time | Product | Conv.[b] | Yield (%)[c] | % ee[d] |
|---|---|---|---|---|---|---|---|---|
| 5 | (structure 57: Br-aryl with diene and vinyl ether) | 22b/24 20 | 10 mol % 15 mol % | 1 h 18 h | (structure 58: dihydropyran product) | >98% 91% | 95 91 | 37 83[28] |

In Table 6: (a) the catalysts were generated in situ as a 0.2 M solution in $C_6D_6$ for 1 h, then added to a solution of substrate in $C_6D_6$ (overall concentration 0.1 M); (b) Determine by $^1$H NMR (400 MHz) analysis of the crude reaction mixture; (c) Isolated yield after purification; (d) Determined by HPLC or GLC analysis.

Example 9

The following describes a variety of enantioselective RCM reactions which illustrate the special utility of the catalysts of the present invention, according to some embodiments.

Figure 2:
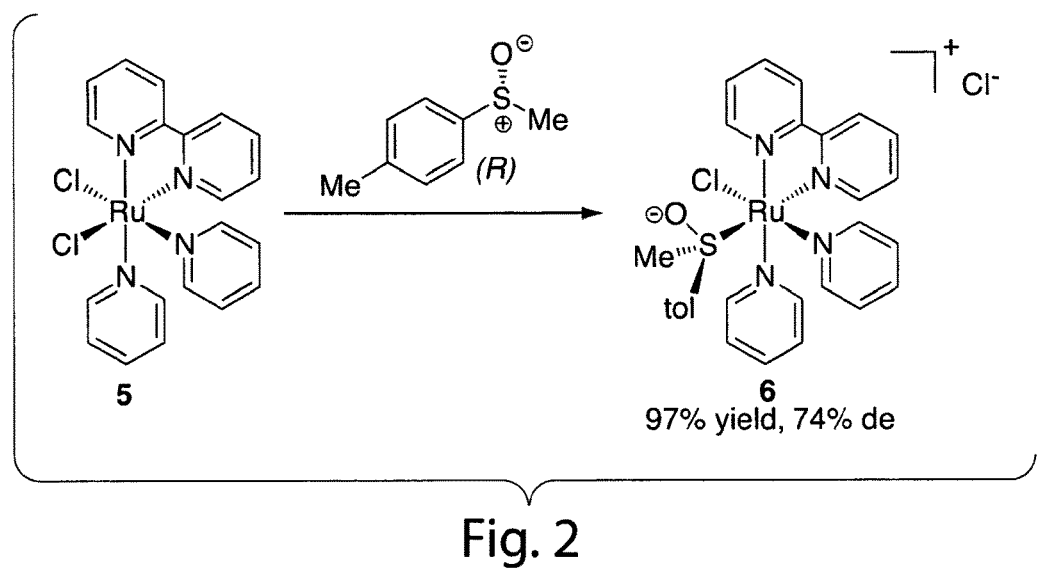
FIG. 2 shows the transformation of a racemic metal complex to a stereogenic-at-metal complex.
Figure 3:
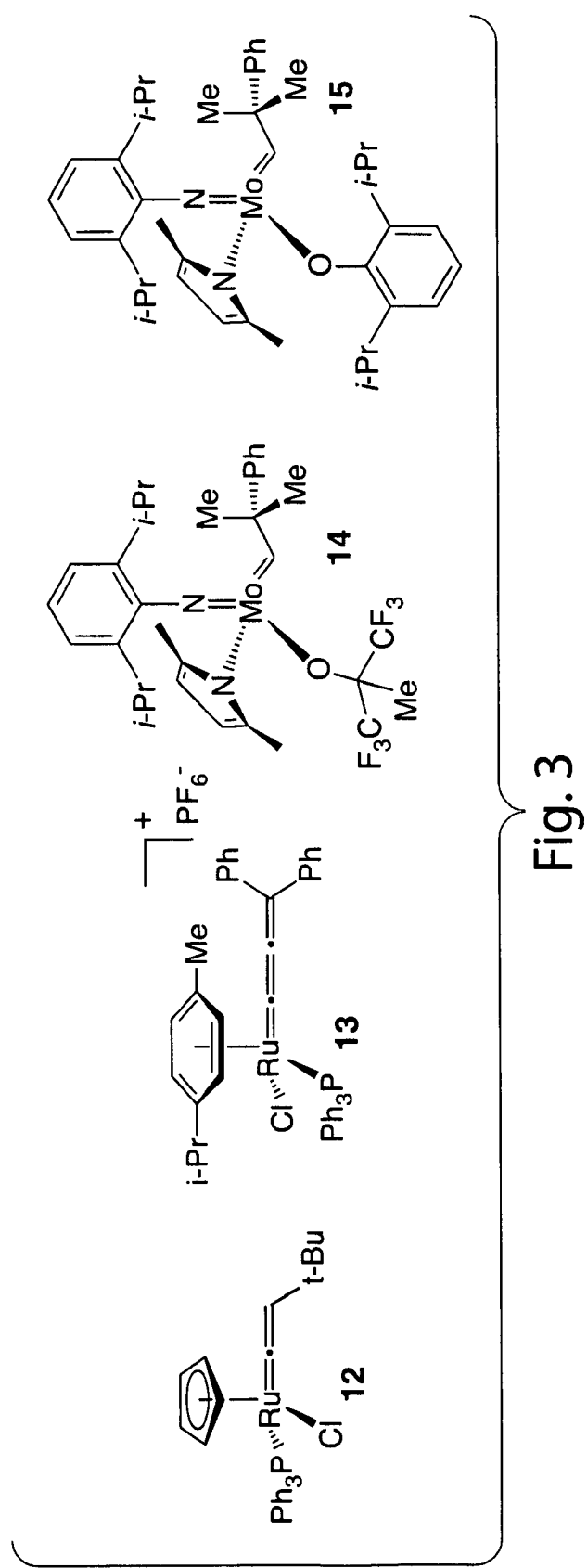
FIG. 3 shows examples of stereogenic metal complexes bearing all monodentate ligands.
Figure 4:
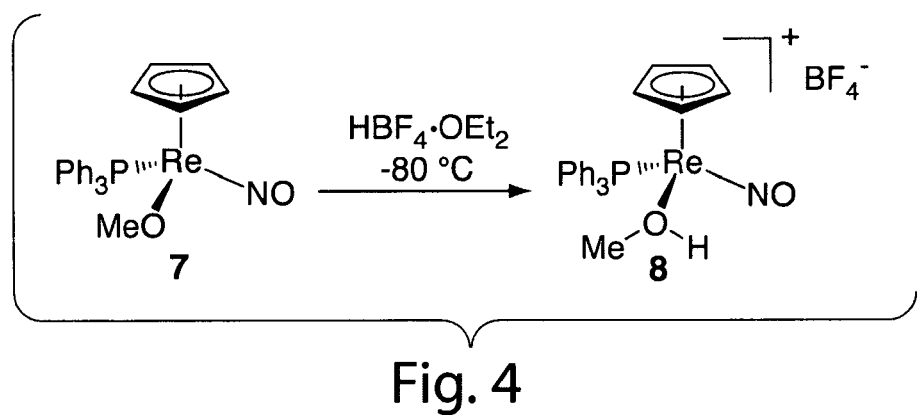
FIG. 4 shows a Re "piano stool" complex.
Figure 5:
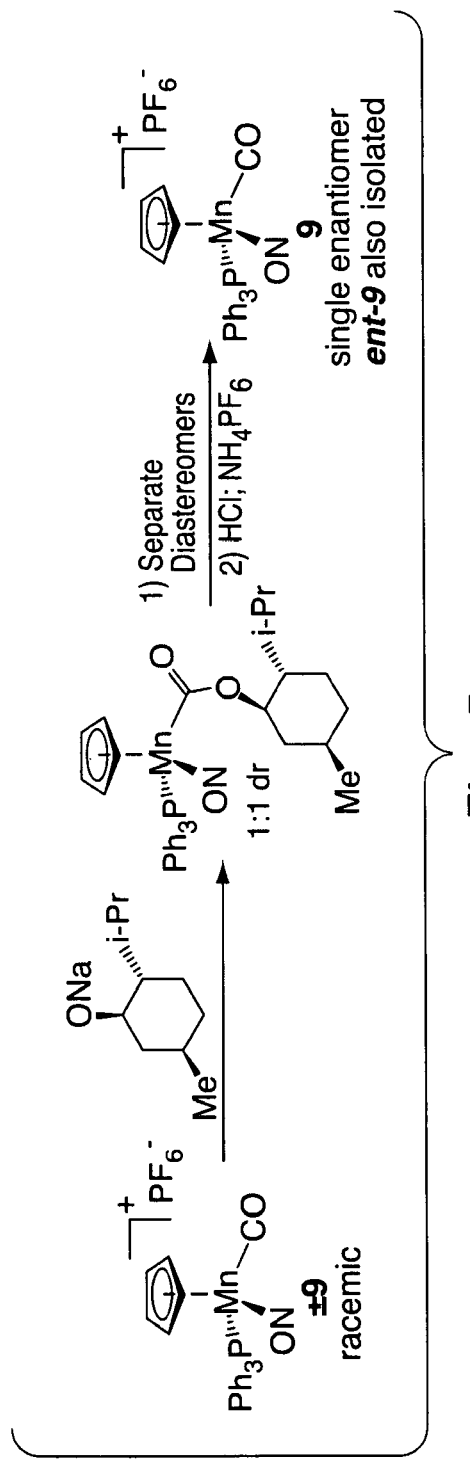
FIG. 5 shows an enantioselective synthesis of a complex having a stereogenic metal center and bearing only monodentate ligands.
Figure 6:
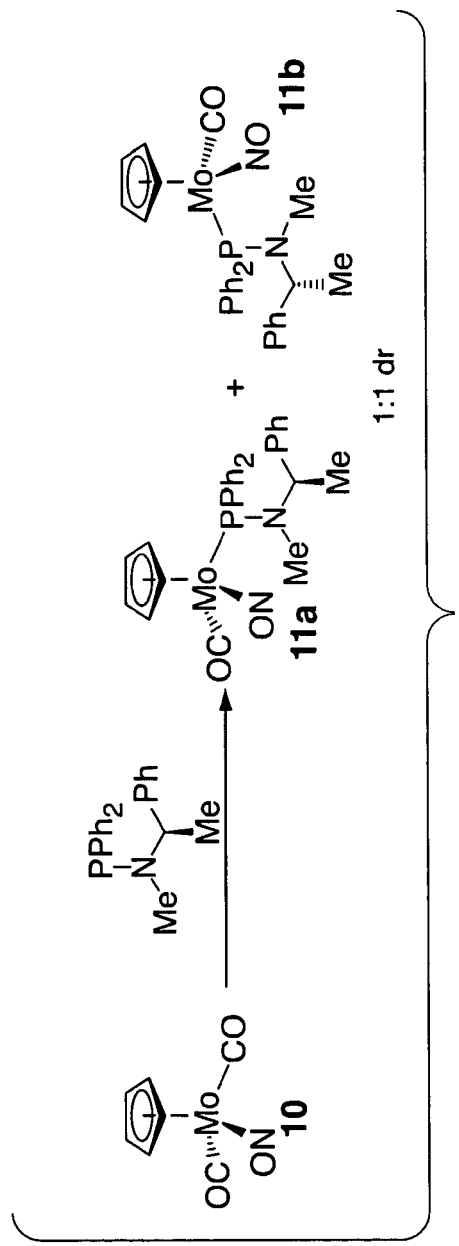
FIG. 6 shows the desymmetrization of a prochiral complex by displacement of a carbonyl ligand with a chiral monodentate phosphine.
Figure 7:
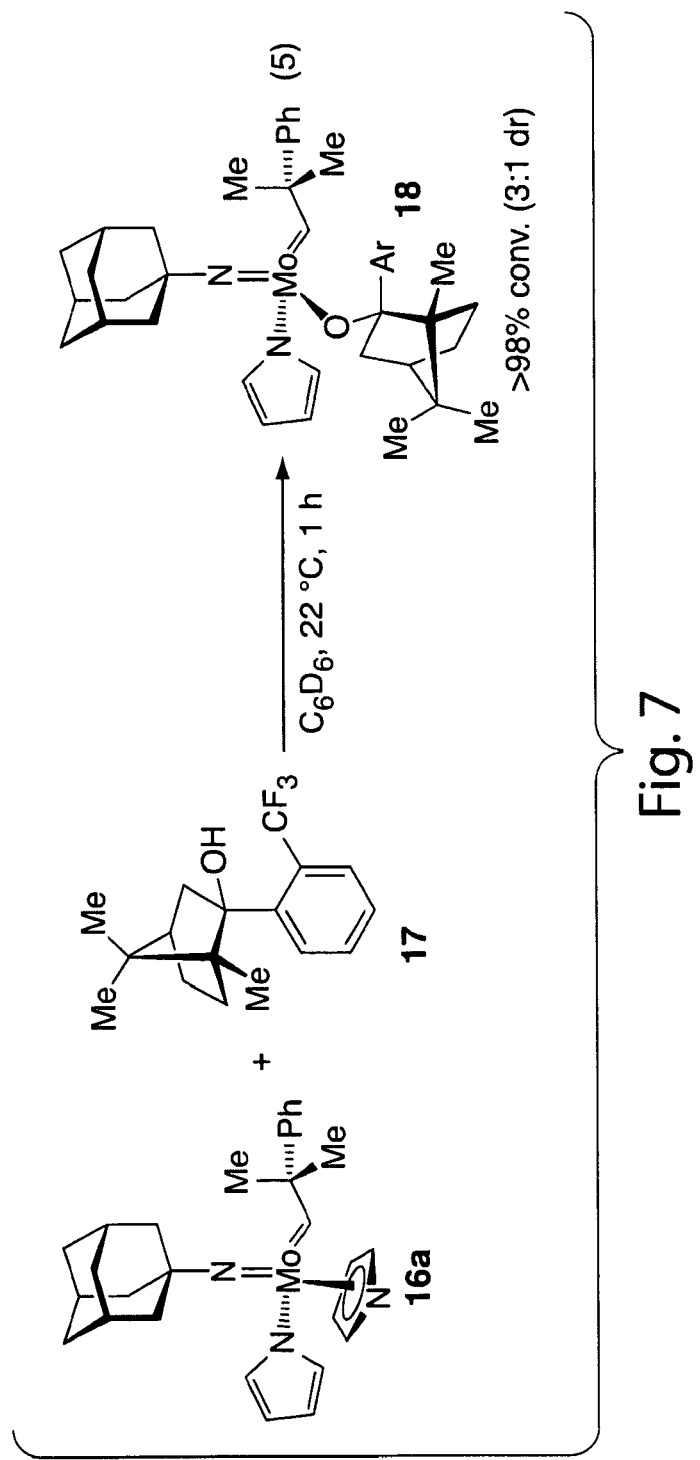
FIG. 7 shows the reaction of Mo metal complex with one equivalent of borneol.

None of the previously reported chiral diolates promoted RCM of secondary allylamine 66 (entry 1, Table 8); in sharp contrast, with 2.5 mol % 28b, there was 94% conversion to piperidine 66 within one hour, furnishing the desired product in 89% yield and 67% e.e. Diolate 20 (see FIG. 25) and 28c (see FIG. 26 for structure; d.r.=5:1) promoted formation of 49 (entry 2, Table 8) with high enantioselectivity (98% and 91% e.e., respectively), but enantioselective RCM with the mono-aryloxide was significantly more efficient: 3 mol % dichloro-substituted 28c furnished 95% conversion to 49 within one hour, whereas 48 hours were required with 10 mol % diolate 20. Reaction of amine 44 (entry 3, Table 8), which required 15 mol % 62b, proceeded to only 75% conversion after 24 hours, yielded 45 with low selectivity (e.r.=65:35). In contrast, 1 mol % 28b was sufficient for >98% conversion within one hour, delivering 45 in >98% yield and 92% e.e. Similarly, enantioselective synthesis of azepine 47 (entry 4, Table 8) was more efficient (one vs. 20 hours) and substantially more selective (81% e.e. vs. 40% e.e.) when 28c was used (vs. diolate 62b). RCM of arylamine 40 (entry 5) proceeded with high enantioselectivity when diolate 62a or mono-aryloxide 28c were used; with 1 mol % 28c, however, there was >98% conversion in one hour (versus seven hours with 2 mol % 62a). With enantioselective RCM of silyl ether 55 (entry 6), diolate 62c initiated a slightly more selective ring closure (e.r.=97:3 vs. 94:6 with 28c); with 1 mol % 28c, conversion of 55 to 56 was complete in 1 hour (vs. 5 mol % and 12 hours with 5c). Three points regarding the transformations in Table 8 merit mention. First, in certain cases, dichloro complex 28c afforded similar, but higher, selectivity compared to dibromo 28b. Second, the Mo center undergoes two inversions in the course of each catalytic cycle (see FIG. 2). Without wishing to be bound by theory, the high enantioselectivities observed may indicate that adventitious isomerization occurs at a minimum or not at all, since such isomerizations would furnish the alternative product enantiomers. Third, chiral Ru-based olefin metathesis catalysts developed thus far only promote RCM of trisubstituted olefins with high selectivity (≥80% e.e. or ≥90:10 e.r.). In Table 8, the reactions in entries 1-3 and 5-6 were carried out in purified benzene or toluene under an atmosphere of nitrogen gas and the reaction in entry 4 was performed in pentane.

TABLE 8

Comparison of catalytic enantioselectivity RCM promoted by chiral Mo diolate and aryloxide-pyrrolide complexes

| Entry no | Substrate | Product | Mo-diolate; mol %* | Time (h); Temp (° C.) | Conv. (%)§; Yield (%)† | e.r.; e.e. (%)‡ | Mo-aryl-oxide; mol %* | Time (h); Temp (° C.) | Conv. (%)§; Yield (%)† | e.r.; e.e. (%)‡ |
|---|---|---|---|---|---|---|---|---|---|---|
| 1 | (structure 66) | 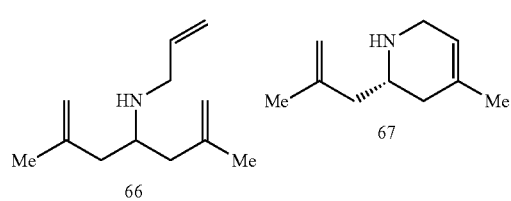 67 | all available | >36; >40 | <5; — | — | 28c; 2.5 | 1; 22 | 94; 89 | 83.5:16.5; 67 |

TABLE 8-continued

Comparison of catalytic enantioselectivity RCM promoted by chiral Mo diolate and aryloxide-pyrrolide complexes

| Entry no | Substrate | Product | Mo-diolate; mol %* | Time (h); Temp (° C.) | Conv. (%)§; Yield (%)† | e.r.; e.e. (%)‡ | Mo-aryloxide; mol %* | Time (h); Temp (° C.) | Conv. (%)§; Yield (%)† | e.r.; e.e. (%)‡ |
|---|---|---|---|---|---|---|---|---|---|---|
| 2 | 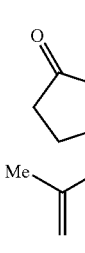 48 | 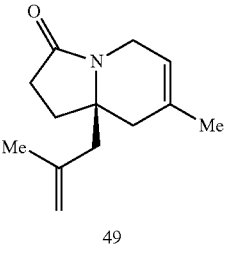 49 | 20; 10 | 48; 22 | >95; 91 | 99:1; 98 | 28c; 3 | 1; 22 | 95; 88 | 95.5:4.5; 91 |
| 3 | 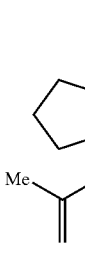 44 | 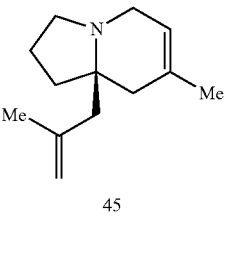 45 | 62b; 15 | 24; 22 | 75; n.d. | 65:35; 30 | 28b; 1 | 1; 22 | >98; >98 | 96:4; 92 |
| 4 |  46 | 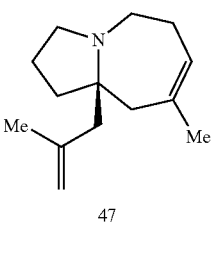 47 | 62b; 5 | 20; 22 | >98; n.d. | 70:30; 40 | 28c; 3 | 1; 22 | 95; 86 | 90.5:9.5; 81 |
| 5 | 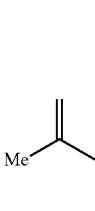 40 | 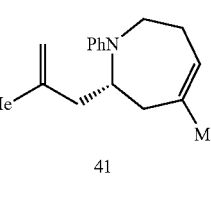 41 | 62a; 2 | 7; 22 | >98; 90 | 97.5:2.5; 95 | 28c; 1 | 1; 22 | >98; 86 | 96.5:3.5; 93 |
| 6 | 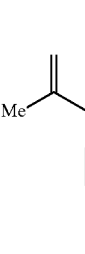 55 | 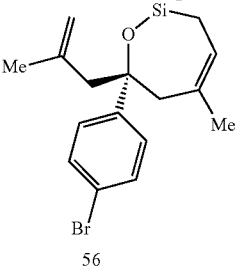 56 | 62c; 5 | 12; 22 | >98; 98 | 97:3; 94 | 28c; 1 | 1; 22 | >98; 84 | 94:6; 88 |

In Table 8:
§Conversion measured by analysis of 400 MHz $^1$H NMR spectra of unpurified mixtures;
†Yield of isolated product after purification;
‡The enantiomer ratio (e.r.) was determined by high pressure liquid or gas liquid chromatography (HPLC or GLC) analysis; The enantiomeric excess (e.e.) was calculated from the e.r.; the variance of e.e. is estimated to be <±2%.

Example 10

Figure 27:
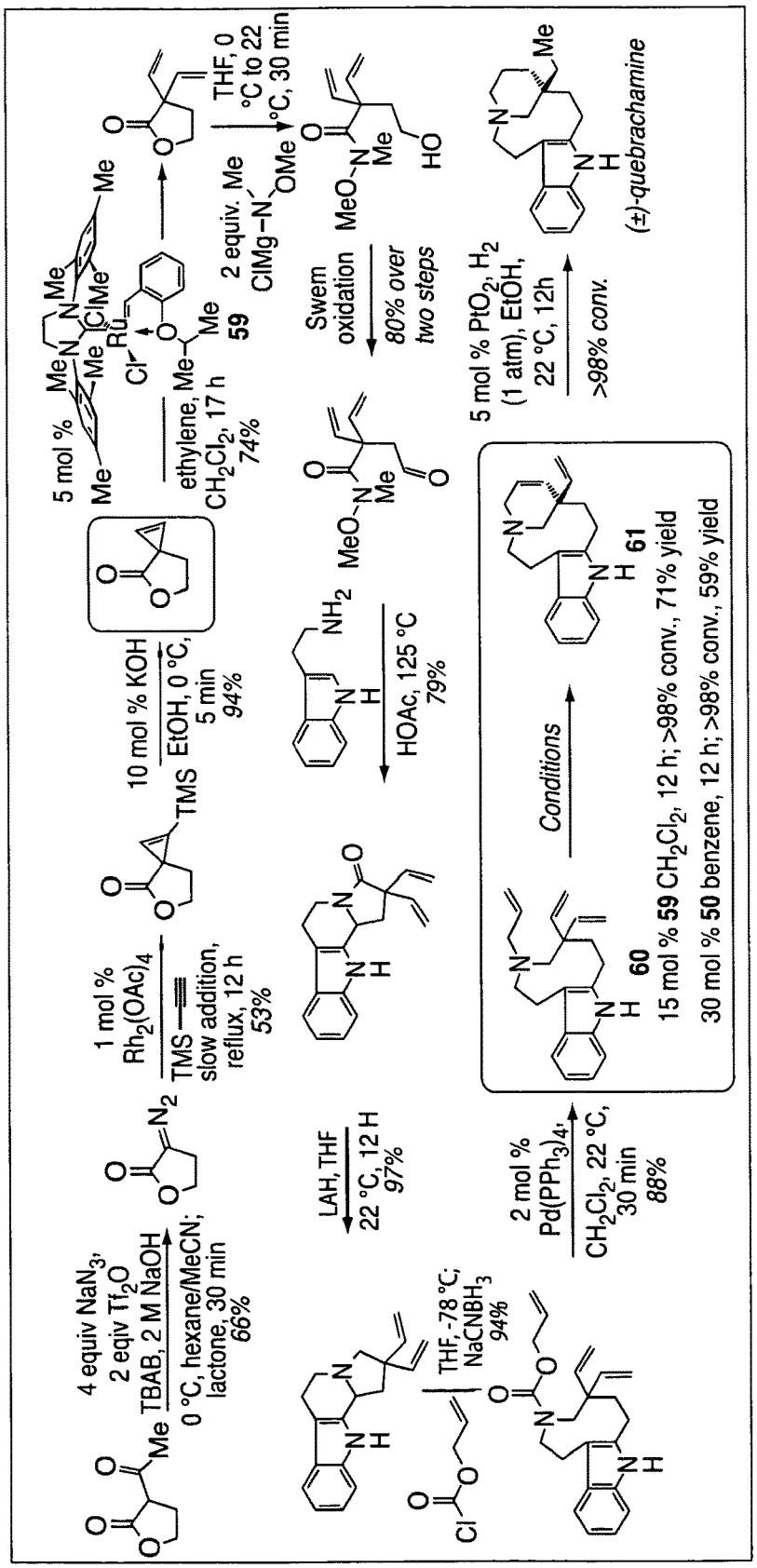
FIG. 27 illustrates the total synthesis of (±)-quebrachamine.
Figure 28:
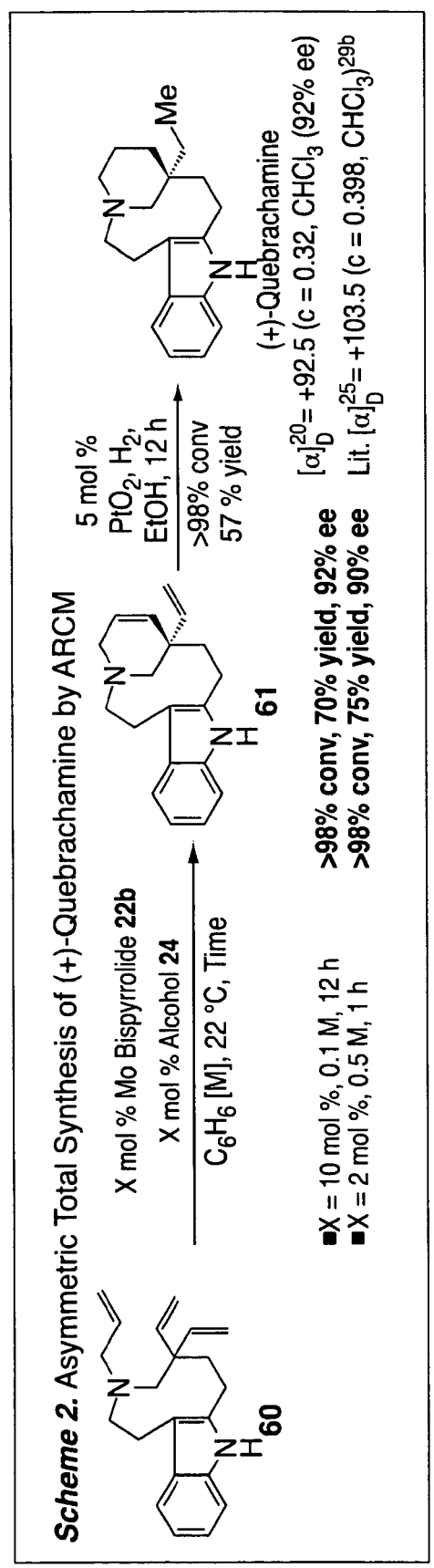
FIG. 28 shows the enantioselective synthesis of (+)-quebrachamine using enantioselective ring-closing metathesis.

The following example describes the enantioselective total synthesis of biologically active natural product (+)-quebrachamine. FIG. 27 shows the total synthesis of quebrachamine. FIG. 28 shows the framework for the synthesis.

The most stringent test for any catalytic reaction is in the arena of complex molecule total synthesis. Catalytic olefin metathesis has proven to be an extremely powerful tool for chemical synthesis, however, application of catalytic asymmetric olefin metathesis in total synthesis is rare; its enormous potential is demonstrated in only a few examples. An elegant synthesis of (±)-quebrachamine, a potent adrenergic blocker, was developed in our laboratories (FIG. 28). The key penultimate step, a ring-closing metathesis of achiral triene 60, which forms the solitary all-carbon stereogenic center in the molecule, was anticipated to be installed using our currently available $C_2$-symmetric Mo diolate catalysts. RCM of 60 with more reactive achiral Mo (50) and Ru (59) catalysts proved difficult; high catalyst loadings were required for complete conversion. None of the existing chiral catalysts (Mo or Ru) delivered any of the desired RCM product 61. Triene 60 has remained a benchmark substrate for new olefin metathesis catalysts, chiral and achiral.

Figure 25:
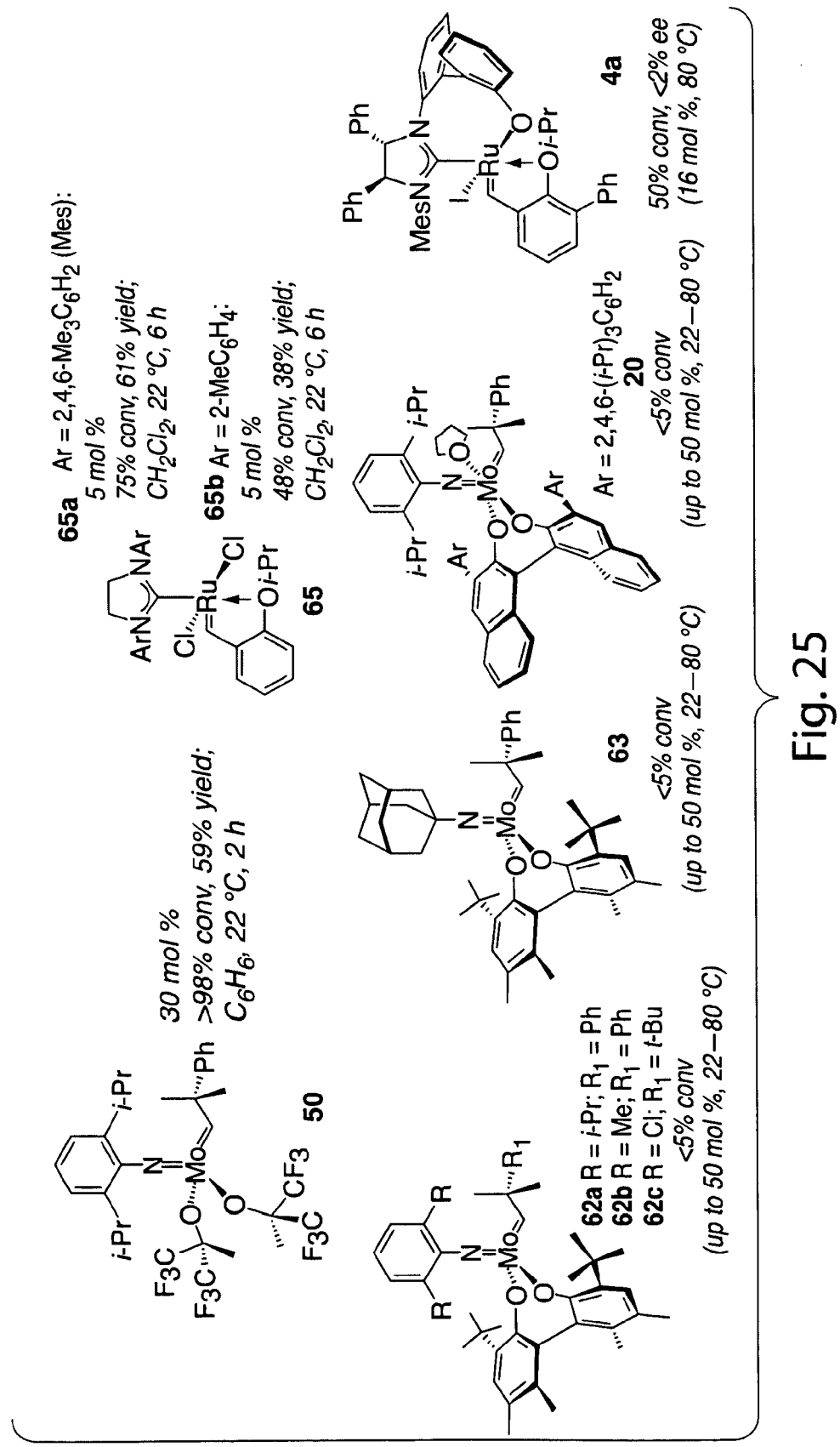
FIG. 25 shows examples of metathesis catalysts.

The results of the transformation of 60 to 61 using various catalysts are illustrated in FIG. 25, regarding Mo alkylidene 50 and Ru carbene 65a, although somewhat inefficient, represent the optimal among available achiral catalysts. The faster initiating 65b proceeds only to 48% conversion, likely as a result of lower stability of the carbene intermediates. Vis-à-vis an enantioselective quebrachamine synthesis, the existing chiral catalysts, represented by 62a-c, 63, and 20, are entirely ineffective in promoting the formation of 61 (≤5% conversion with up to 50 mol % loading after up to 48 hours at 22-80° C.). With 16 mol % 4a at 80° C., there is approximately 50% conversion, but only rac-61 is generated; related monodentate N-heterocyclic chiral Ru carbenes are equally ineffective.

As shown in FIG. 28, chiral catalyst 28b efficiently promotes ARCM of 60, generating the all-carbon quaternary stereogenic center in high selectivity (92% e.e.). Most notably, the reaction proceeds to >98% conversion in 1 h with 2 mol % catalyst (75% yield, 90% e.e.). Hydrogenation of 61 proceeds smoothly with 5 mol % $PtO_2$ to afford (+)-quebrachamine.

Figure 26:
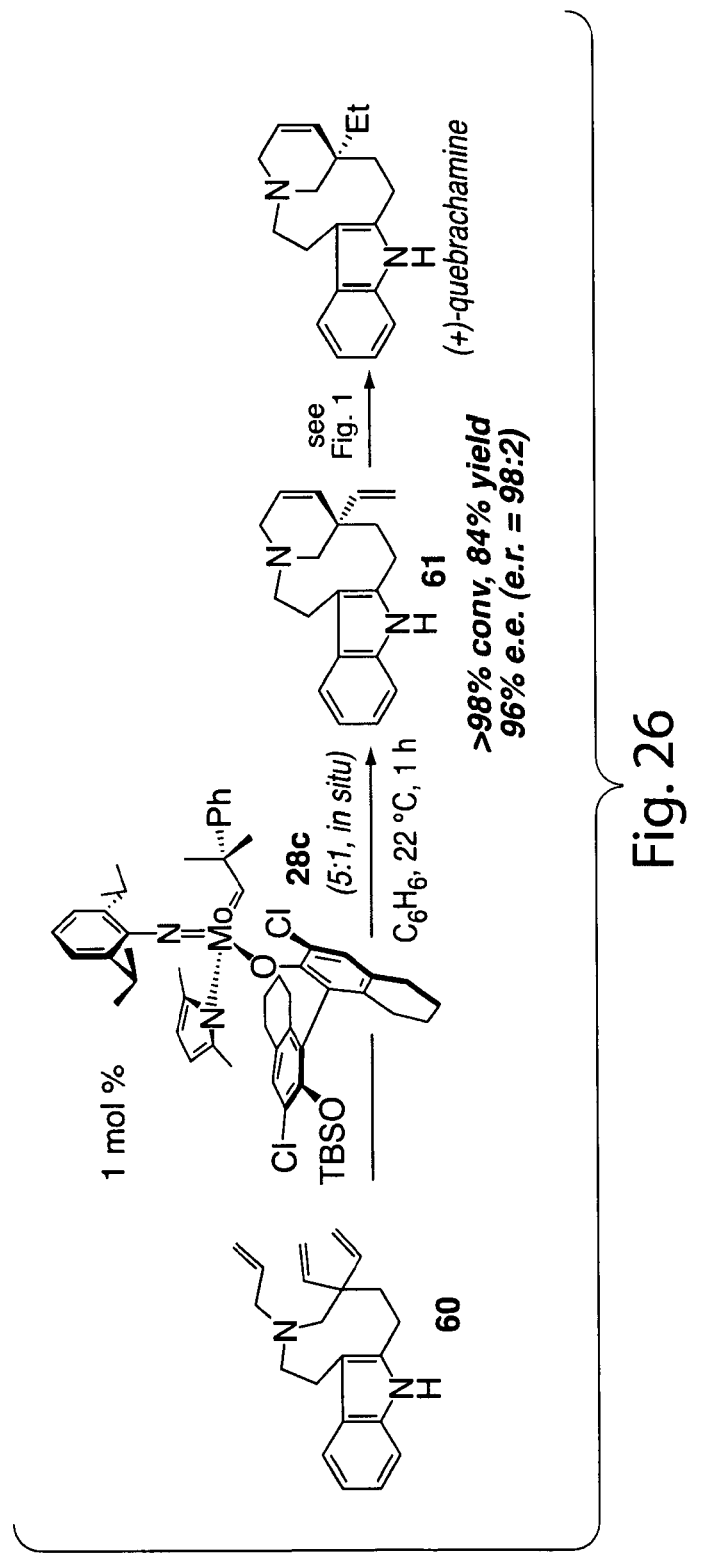
FIG. 26 shows the synthesis of (+)-quebrachamine using a Mo-complex of the invention.

In the presence of 1 mol % in situ-generated 28c, triene 60 is transformed entirely in one hour to 61 in 84% yield and 96% e.e. (FIG. 26). The target alkaloid is subsequently obtained in high enantiomeric purity and yield (97%). The Mo-catalyzed process in FIG. 26 constitutes the first application of a highly effective catalytic ARCM (e.r. ≥95:5) to the enantioselective total synthesis of a relatively complex natural product.

Example 11

Figure 19:
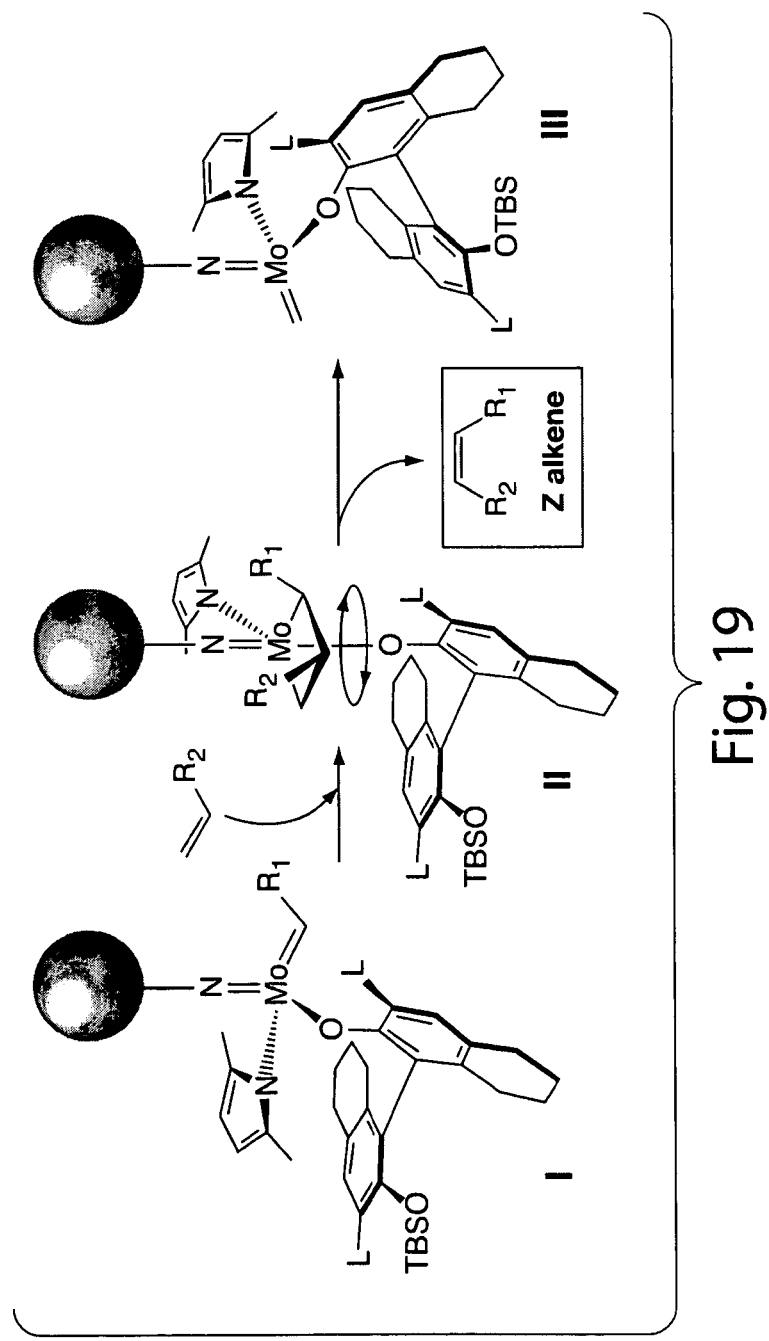
FIG. 19 shows the effects of altering the size of the ligands of a Mo-complex on alkene insertion and formation of Z product, according to some embodiments.
Figure 29:
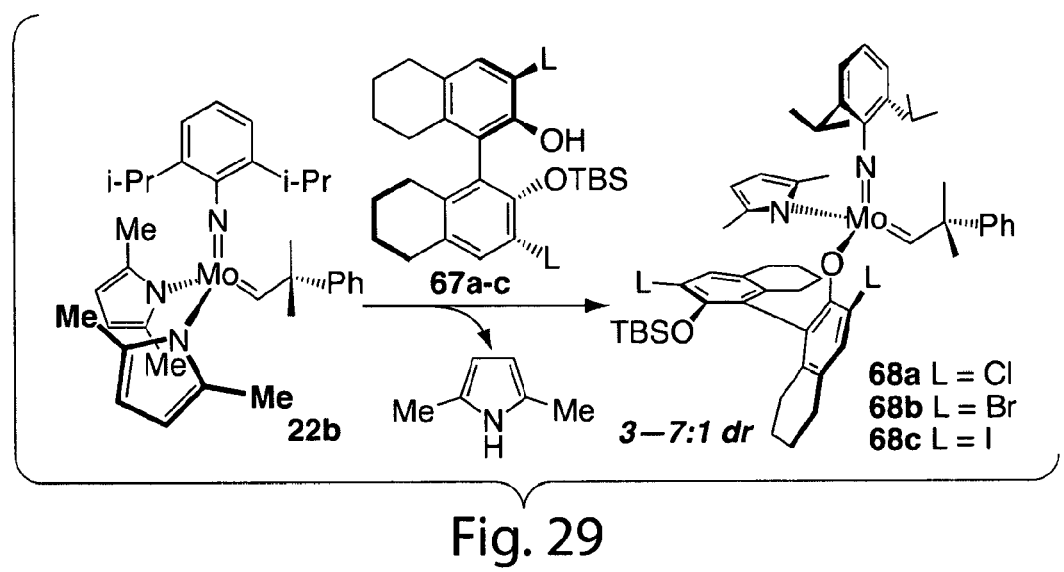
FIG. 29 shows the synthesis of various Mo-complexes of the present invention.

Previously examples describe the synthesis of a class of effective chiral olefin metathesis catalysts, which bear a stereogenic metal center. In this example, complexes 68a-c (see FIG. 29) are synthesized and employed in various metathesis reactions. The Mo alkylidenes are prepared by treatment of a bispyrrolide (e.g., 22b) with a mono-protected binaphthol derivative (67a-c). Without wishing to be bound by theory, the flexibility of the Mo monoaryloxides might be utilized to furnish Z alkenes. A sterically demanding and freely rotating aryloxide ligand (rotation around the Mo—O bond) in combination with a sufficiently smaller imido substituent (vs. aryloxide) should favor reaction through the syn alkylidene isomer (I, FIG. 19) and an all-Z metallacyclobutane (II, FIG. 19), producing Z-alkene products. In contrast, with the previously examined Mo diolates, the rigidly bound chiral bidentate ligand presents a substantially less significant steric barrier; as a result, anti alkylidenes and trans-substituted metallacyclobutanes become energetically viable intermediates.

Figure 30:
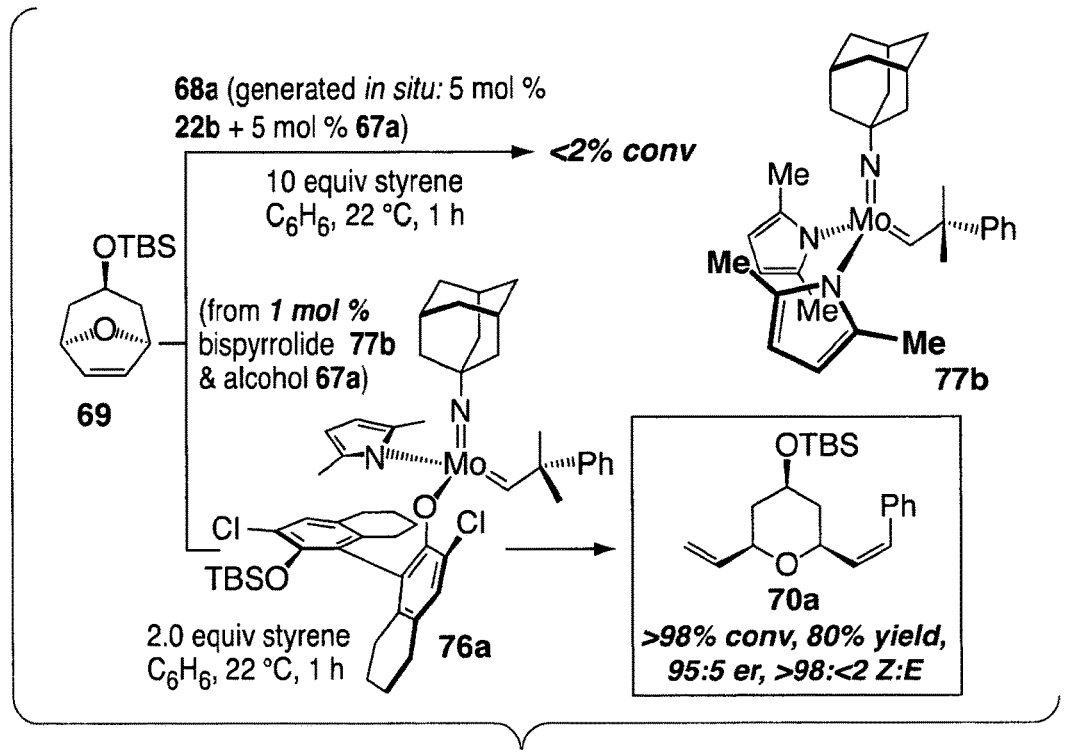
FIG. 30 shows a metathesis reaction catalyzed by a Mo complex comprising an imido group ligand, and the effect of the imido group size on the activity and selectivity of the metathesis reaction.

As the first step towards investigating the validity of the above hypotheses, oxabicycle 69 and styrene was subjected to chiral complex 68b, prepared through treatment of 5 mol % 22b with the corresponding aryl alcohol (67a); the chiral catalyst is typically used in situ. As shown in FIG. 30, conversion to the desired ROCM product was not observed (<2% and minimal benzylidene formation by $^1$H NMR analysis). Without wishing to be bound by theory, a larger arylimido unit in 68b, together with the sizeable aryloxide unit, might constitute a Mo complex that is too sterically demanding for formation of the requisite syn or anti alkylidene (cf. I) and subsequent cross-metathesis. To address this complication, 76a (FIG. 30; 3.0:1 d.r.) was prepared comprising an alkylidene that bears the smaller adamantyl imido unit; such an alteration, may enhance activity as well as promote Z-selectivity. When oxabicycle 69 was treated with a solution containing styrene, 1 mol % of adamantyl imido bispyrrolide (77b) and alcohol 67a, ROCM proceeded to >98% conversion within one hour, affording 70a in 80% yield and 95:5 e.r.; the desired product was obtained exclusively as a Z olefin (>98:<2 Z:E).

As the data summarized in entry 2 of Table 9 indicate, when Br-substituted chiral aryl alcohol 67b was used to prepare the catalyst (76), ROCM was catalyzed with an equally exceptional level of Z-selectivity but with improved enantioselectivity (98.5:1.5 e.r. vs. 95:5 e.r. with 67a as aryl alcohol in entry 1). Reaction with I-substituted 76c was more enantioselective (>98:<2 e.r., entry 3), affording Z-70a predominantly (95:5 Z:E). Reaction efficiency was reduced with 77c-d: ROCM proceeded to ~75% conversion, affording 70a in 60 and 57% yield, respectively. As illustrated in Table 9 (third column), in the case of 77d, chiral Mo synthesis was accompanied by generation of relatively inactive bisaryloxides. That is, in all processes described, the amount of catalytically active monoaryloxide, prepared and utilized in situ, was less than indicated by the amount of bispyrrolide and alcohol used. For example, the effective catalyst loading for the transformation in entry 2 of Table 9 is ~0.6 mol %. The lower Z-selectivity in the reaction with 5d (entry 4, Table 9) may be due to trans-selective ROCM that may be promoted, albeit inefficiently, by the unreacted bispyrrolide (with 5 mol % 77b: 21% conv to 70a in 1 h, 3:1 trans:Z).

TABLE 9

Z- and enantioselective ROCM of 69 with styrene (to afford 70a) catalyzed by various chiral Mo-based monoaryloxides.

| entry | chiral complex; complex dr[b] | mono-:bisaryloxide:bispyrrolide (%) | conv (%);[b] yield (%)[c] | er[d] | Z:E[e] |
|---|---|---|---|---|---|
| 1 | 76a(L = Cl); 3.0:1 | 56:22:22 | >98; 80 | 95:5 | >98:<2 |
| 2 | 76b(L = Br); 2.2:1 | 62:8:30 | 98; 85 | 98.5:1.5 | >98:<2 |
| 3 | 76c(L = I); 1.7:1 | 67:04:29 | 76; 60 | >98:<2 | 95:5 |
| 4 | 76d(L = F); nd | 07:47:46 | 75; 57 | 95:5 | 80:20 |

For Table 9:
aPerformed with 1.0 mol % bispyrrolide and 1.0 mol % enantiomerically pure (>99% e.e.) aryl alcohol, 2.0 equiv styrene in $C_6D_6$ (or toluene), 22° C., 1.0 h, $N_2$ atm;
[b]Determined by analysis of 400 MHz $^1$H NMR spectra of unpurified mixtures;
[c]Yield of purified products;
[d]Determined by HPLC analysis;
[e]Determined by analysis of 400 MHz $^1$H NMR spectra of unpurified mixtures in comparison with authentic trans-olefin isomer;
n.d. = not determined.

Although stereoselectivity of olefin formation varies as a function of the electronic or steric attributes of the cross partner, Z-alkenes remained strongly preferred in all cases (Table 10). Reaction with p-methoxy styrene and 76b as the catalyst afforded pyran 70b with 94.5:5.5 Z:E selectivity (entry 1, Table 10). When p-trifluoromethyl styrene was used, 70c was isolated with complete Z-selectivity (>98:<2 Z:E, entry 3). Without wishing to be bound by theory, the higher activity of the electron-rich alkene may allow partial reaction through the sterically less favored anti alkylidene. In spite of the increase in the steric bulk of the aryl substituent in the reactions shown in entries 3-4 of Table 10, preference for the Z-alkene was only slightly diminished, which may be due to elevated steric congestion in the derived all-syn metallacyclobutane (cf. II, FIG. 19).

TABLE 10

Z- and enantioselective ROCM of 69 with various aryl olefins.

| entry | Ar; Ar-olefin equiv | mol % 77b; mol % 67b | time (h) | conv (%);[b] yield (%)[c] | er[d] | Z:E[e] |
|---|---|---|---|---|---|---|
| 1 | b p-OMeC$_6$H$_4$; 2 | 1.0; 1.0 | 0.5 | 96; 80 | 97:3 | 94.5:5.5 |
| 2 | c p-CF$_3$C$_6$H$_4$; 2 | 1.0; 1.0 | 1.0 | 96; 67 | 98:2 | >98:<2 |
| 3 | d o-BrC$_6$H$_4$; 10 | 2.0; 2.0 | 1.0 | 94; 50 | 99:1 | 89:11 |
| 4 | e o-MeC$_6$H$_4$; 10 | 2.0; 2.0 | 1.0 | 97; 54 | 99:1 | 87.5:12.5 |

For Table 10:
aPerformed with 1.0 mol % bispyrrolide and 1.0 mol % enantiomerically pure (>99% e.e.) aryl alcohol, 2.0 equiv styrene in $C_6D_6$ (or toluene), 22° C., 1.0 h, $N_2$ atm;
[b]Determined by analysis of 400 MHz $^1$H NMR spectra of unpurified mixtures;
[c]Yield of purified products;
[d]Determined by HPLC analysis;
[e]Determined by analysis of 400 MHz $^1$H NMR spectra of unpurified mixtures in comparison with authentic trans-olefin isomer;
n.d. = not determined.

Figure 31:
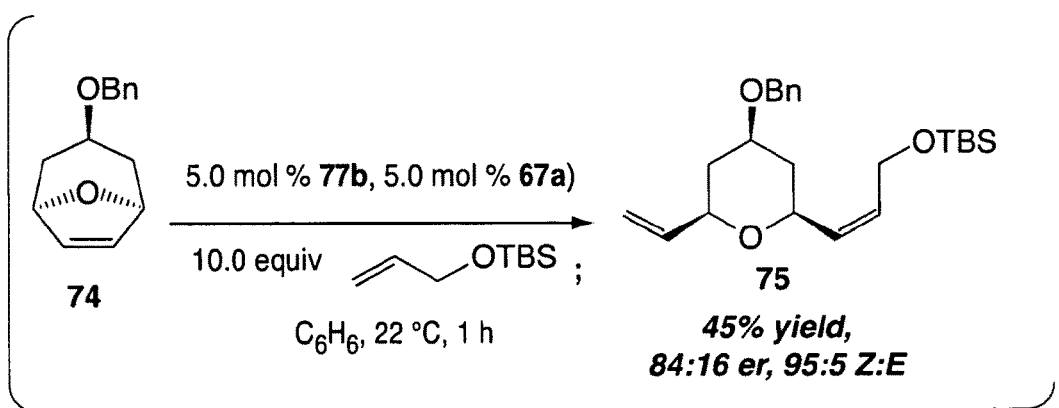
FIG. 31 shows a metathesis reaction using Mo-complexes of the present invention.

The findings in Table 11 illustrate that ROCM reactions proceeded with a range of substrates to afford trisubstituted pyrans efficiently (75-83% yield) and with high enantio- (92:8-98:2 e.r.) and Z-selectivity (89:11-96:4 Z:E). The need for larger amounts of aryl olefin (10.0 equiv) and the higher catalyst loadings may be due to lower reactivity (reduced strain) of cyclic alkene diastereomers 71a-c (vs. 69) and that of the corresponding benzyl ethers 72-73. Another non-limiting example is shown in FIG. 31.

TABLE 11

Z- and Enantioselective ROCM of oxabicycles with aryl olefins.

| entry | product | mol % 77a & 67b; olefin equiv | temp (° C.); time (h) | conv (%);[b] yield (%)[c] | er[d] | Z:E[e] |
|---|---|---|---|---|---|---|
| 1 | 71 a-c (TBSO...; a G=H, b G=OMe, c G=CF$_3$) | 2.0; 10.0 | 22; 1.0 | 91; 83 | 97:3 | 96:4 |
| 2 | | 3.0; 10.0 | 22; 0.5 | 90; 80 | 96:4 | 89:11 |
| 3 | | 2.0; 10.0 | 22; 1.0 | 97; 81 | 98:2 | 94:6 |
| 4 | 72 (BnO) | 5.0; 10.0 | 60; 1.0 | 98; 75 | 92:8 | 95:5 |
| 5 | 73 (BnO) | 2.0; 10.0 | 22; 1.0 | 84; 80 | 92:8 | 91:9 |

For Table 11:
aPerformed with 1.0 mol % bispyrrolide and 1.0 mol % enantiomerically pure (>99% e.e.) aryl alcohol, 2.0 equiv styrene in C$_6$D$_6$ (or toluene), 22° C., 1.0 h, N$_2$ atm;
[b]Determined by analysis of 400 MHz $^1$H NMR spectra of unpurified mixtures;
[c]Yield of purified products;
[d]Determined by HPLC analysis;
[e]Determined by analysis of 400 MHz $^1$H NMR spectra of unpurified mixtures in comparison with authentic trans-olefin isomer;
n.d. = not determined.

Example 12

The following provides information about the specific methodology and characterization used in the previous examples.

General:

All reactions were carried out in oven- (135° C.) or flame-dried glassware under an inert atmosphere of dry N$_2$ unless otherwise stated. Alcohols 23, 83, and 86 and substrates 38, 40, 48, 55, 60, and 66, were dried by azeotropic distillation with C$_6$H$_6$ prior to use in reactions with Mo-based reagents. Substrates 40 and 46 were dried by distillation from Na prior to use in reactions with Mo reagents. Substrates 60, 38, 40, 44, 46, 48, 55, and 66 were synthesized according to previously reported procedures (e.g., see E. S. Sattely, Ph.D. Thesis, Boston College, 2007; S. J. Dolman, et al, J. Am. Chem. Soc., 2002, 124, 6991-6997; E. S. Sattely et al., J. Am. Chem. Soc., 2005, 127, 8526-8533; A. F. Kiely et al., J. Am. Chem. Soc., 2002, 124, 2868-2869). Infrared (IR) spectra were recorded on a Nicolet 210 spectrometer or on a Bruker FTIR Alpha (ATR Mode) spectrometer, $v_{max}$ in cm$^{-1}$. Bands are characterized as broad (br), strong (s), medium (m), or weak (w). $^1$H-NMR spectra were recorded on a Varian Gemini 2000 (400 MHz) spectrometer. Chemical shifts are reported in ppm from tetramethylsilane with the solvent resonance resulting from incomplete deuteration as the internal reference (CDCl$_3$: δ 7.26, C$_6$D$_6$: δ7.16). Data are reported as follows: chemical shift, integration, multiplicity (s=singlet, d=doublet, t=triplet, br=broad, m=multiplet), coupling constants (Hz). $^{13}$C-NMR spectra were recorded on a Varian Gemini 2000 (100 MHz) spectrometer with complete proton decoupling. Chemical shifts are reported in ppm from tetramethylsilane with the solvent as the internal reference (CDCl$_3$: δ 77.16). Enantiomer ratios were determined by HPLC (Chiral Technologies Chiralpak OD column or Chiralcel OD-R column (4.6 mm×250 mm)) or by GLC analysis (Alltech Associates Chiraldex GTA or Supelco Betadex (30 m×0.25 mm)) in comparison with authentic racemic materials. High-resolution mass spectrometry was performed on a Micromass LCT ESI-MS (positive mode) at the Boston College Mass or at the University of Illinois Mass Spectrometry Laboratory. Elemental analysis was performed at Midwest Microlab, LLC (Indianapolis, Ind.). Optical rotation values were recorded on a Rudolph Research Analytical Autopol IV polarimeter. Melting points were measured on a Thomas Hoover capillary melting point apparatus and are uncorrected. X-ray crystallography was performed at the Massachusetts Institute of Technology X-ray Crystallographic Laboratory.

Solvents:

Solvents were purged with argon and purified under a positive pressure of dry argon by a modified Innovative Technologies purification system: diethyl ether (Aldrich) and dichloromethane (Doe & Ingalls) were passed through activated alumina columns; benzene (Aldrich), toluene (Doe & Ingalls), and pentane (J T. Baker) were passed successively through activated Cu and alumina columns. Tetrahydrofuran (Aldrich) was distilled from sodium benzophenone ketyl. Methanol (Doe & Ingalls) and ethanol (Doe & Ingalls) were distilled from magnesium methoxide.

Metal-Based Complexes:

Mo-based bis(alkoxide) complexes 50 and 62a-c, 63, and 20 were prepared according to published procedures (e.g., see R. R. Schrock et al., *Angew. Chem., Int. Ed.,* 2003, 42, 4592-4633 and references cited therein). Mo-bis(pyrrolide) complexes 22a-b were prepared according to published procedures (e.g., see R. R. Schrock et al., *Angew. Chem., Int. Ed.,* 2003, 42, 4592-4633 and references cited therein). Mo-monoalkoxide-monopyrrolide complex rac-9 was prepared according to published procedures (e.g., see R. R. Schrock et al., *Angew. Chem., Int. Ed.,* 2003, 42, 4592-4633 and references cited therein). Mo complexes were handled under an inert atmosphere in a dry box. Ru-based complex 65a was obtained from Materia, Inc. and purified by silica gel column chromatography and recrystallization prior to use. Ru-based complex 65b was purchased from Materia and used as received. Ru-based complex 4a was prepared according to published procedures (e.g., see Van Veldhuizen et al., *J. Am. Chem. Soc.,* 2005, 127, 6877-6882). Ru-based complexes were handled under an inert atmosphere in a dry box for comparison purposes.

Reagents:

$D_6$-Benzene was purchased from Cambridge Isotope Laboratories and distilled from Na into activated 4 Å molecular sieves prior to use. (R)-binol was purchased from Kankyo Kakagu Center, Co. and used as received. Bromine was purchased from Acros and distilled from $P_2O_5$ prior to use. tert-Butyldimethylsilyl chloride was purchased from Oakwood and used as received. tert-Butyldimethylsilyl trifluoromethanesulfonate was purchased from Aldrich or Oakwood and distilled prior to use. n-Butyl lithium (15% in hexanes) was purchased from Strem and titrated with s-butanol (1,10-phenanthroline as indicator) prior to use. $d_1$-Chloroform was purchased from Cambridge Isotope Laboratories and distilled from $CaH_2$ into activated 4 Å molecular sieves prior to use with Mo complexes. Chloromethyl methyl ether was purchased from Aldrich and used as received. Concentrated aqueous $NH_4OH$ (Assay, as $NH_3$, w/w 28.9%) was purchased from Fisher and used as received. Hexachloroethane was purchased from Alfa Aesar and recrystallized from ethanol, then dried by azeotropic distillation with $C_6H_6$, prior to use. Hydrogen chloride (4.0 M in dioxane) was purchased from Aldrich and used as received. Platinum(IV) oxide was purchased from Aldrich and used as received. Potassium carbonate was purchased from Fisher and used as received. Sodium bisulfite was purchased from Fisher and used as received. Sodium hydride (60% dispersion in mineral oil) was purchased from Strem and used as received. Triethylamine was purchased from Aldrich and distilled from $CaH_2$ prior to use.

Figure 33:
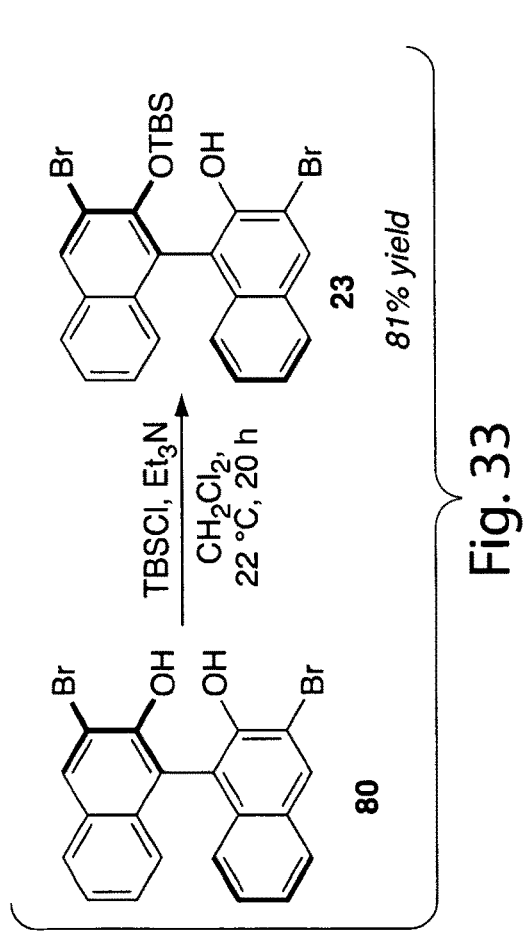
FIG. 33 shows the synthesis of an oxygen-containing ligand lacking a plane of symmetry from (R)-3,3'-dibromo-1,1'-binaphthyl-2,2'-diol.

Synthesis of Chiral Phenol Ligands:

All ligands were prepared from enantiomerically pure (R)-binol. (R)-3,3'-Dibromo-1,1'-binaphthyl-2,2'-diol (80) (FIG. 33) was prepared according to known procedures (e.g., see Zhu et al., *J. Am. Chem. Soc.* 1999, 121, 8251-8259; Maruoka et al., *Bull. Chem. Soc. Jpn,* 1988, 61, 2975-2976). (R)-5,5',6,6',7,7',8,8'-octahydro-1,1'-binaphthyl-2,2'-diol (81) was synthesized according to a previously reported procedure (e.g., see Aeilts et al., *Angew. Chem., Int. Ed.* 2001, 40, 1452-1456).

(R)-3,3'-Dibromo-2'-(tert-butyldimethylsilyloxy)-1, 1'-binaphthyl-2-ol (23)

(See FIG. 33) A 50-mL round-bottom flask containing with magnetic stir bar was charged with diol 80 (235 mg, 0.530 mmol), $CH_2Cl_2$ (15 mL) and $Et_3N$ (100 uL, 0.690 mmol). tert-Butyldimethylsilyl chloride (104 mg, 0.690 mmol) was then added as a solid in one portion and the mixture was allowed to stir for 20 h, after which it was diluted with a saturated aqueous solution of $NH_4Cl$ (20 mL). The layers were partitioned. The aqueous layer was washed with $CH_2Cl_2$ (2×20 mL). The combined organic layers were dried over $MgSO_4$, filtered, and concentrated. The resulting yellow foam was purified by silica gel chromatography (dry load method, 15:1 petroleum ether:$Et_2O$) to afford 23 (238 mg, 0.430 mmol, 81.0% yield) as a white solid. m.p.=158-159° C.; IR (neat) 3509 (m), 2951 (m), 2928 (m), 2883 (m), 2856 (m), 1493 (m), 1444 (m), 1414 (s), 1357 (m), 1250 (s), 1193 (m), 1149 (m), 1013 (m), 938 (m), 881 (m), 840 (s), 781 (s), 746 (s) cm$^{-1}$; $^1$H NMR (400 MHz, CDCl$_3$) δ 8.29 (1H, s), 8.21 (1H, s), 7.78 (2H, app t, J=8.8 Hz), 7.41-7.27 (4H, m), 7.14 (2H, app t, J=8.4 Hz), 5.58 (1H, s), 0.68 (9H, s), −0.27 (3H, s), −0.42 (3H, s); $^{13}$C NMR (100 MHz, CDCl$_3$) δ 148.9, 148.0, 134.0, 133.3, 132.8, 132.3, 130.5, 129.8, 127.3, 127.3, 127.2, 127.2, 125.8, 125.7, 125.3, 124.6, 121.1, 117.6, 117.2, 112.5, 25.9, 18.5, −3.3, −3.5; HRMS (ESI$^+$) [M+H]$^+$ calcd for $C_{26}H_{27}Br_2O_2Si$: 557.0147. found: 557.0130; [α]$_D^{20}$+50.2 (c=1.00, CHCl$_3$).

(R)-3,3'-Dibromo-2'-(tert-butyldimethylsilyloxy)-5, 5',6,6',7,7',8,8'-octahydro-1,1'-binaphthyl-2-ol (83)

Figure 34:
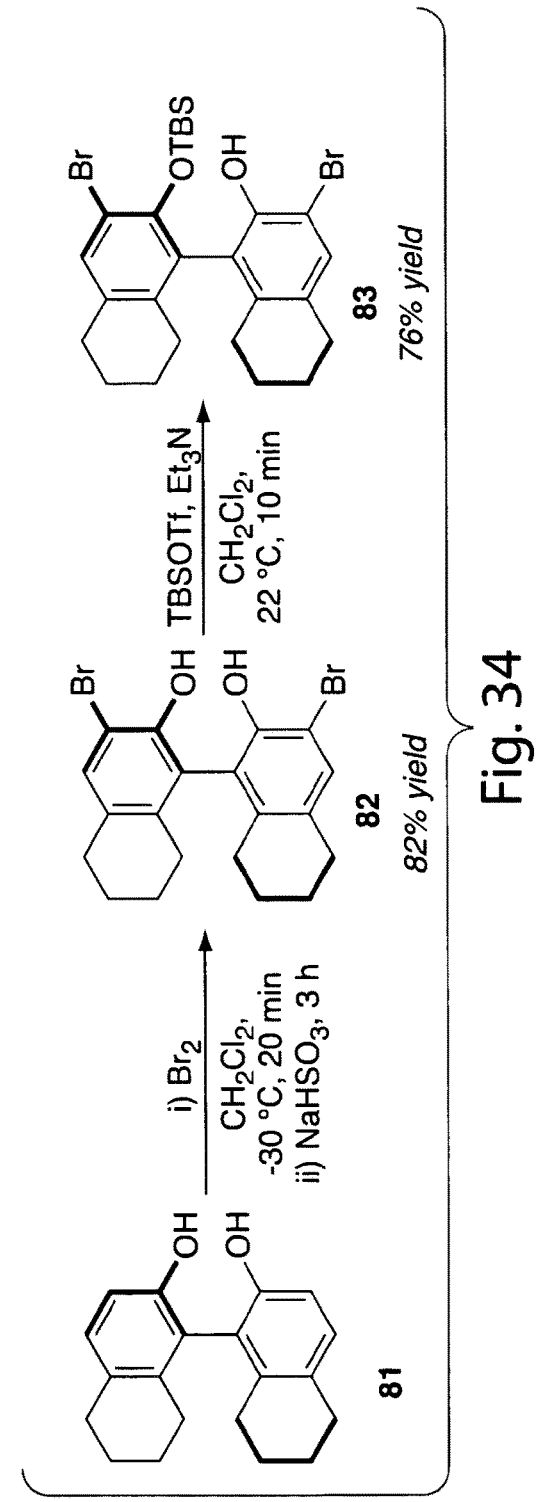
FIG. 34 shows the synthesis of an oxygen-containing ligand lacking a plane of symmetry from (R)-5,5',6,6',7,7',8,8'-octahydro-1,1'-binaphthyl-2,2'-diol.

(See FIG. 34). A 500-mL round-bottom flask equipped with magnetic stir bar was charged with diol 81 (5.00 g, 17.1 mmol) and $CH_2Cl_2$ (150 mL). The solution was allowed to cool to −30° C. (dry ice/acetone bath). Bromine (1.95 mL, 38.5 mmol) was added in one portion by syringe. After 20 min, the reaction was quenched by the slow addition of a saturated aqueous solution of $NaHSO_3$ (200 mL). The mixture was allowed to warm to 22° C. and stir for an additional 3 h, at which time the layers were partitioned and separated. The organic layer was washed with a saturated aqueous solution of $NaHCO_3$ (300 mL), dried over $MgSO_4$, filtered, and concentrated. The resulting brown solid was passed through a short plug of silica gel (eluted with $CH_2Cl_2$) to afford 82 (6.33 g, 14.1 mmol, 82% yield) as a white solid. 82 is a previously reported compound; physical and spectral properties match those disclosed.

A 250-mL round-bottom flask containing a magnetic stir bar was charged with diol 82 (3.0 g, 6.7 mmol), $CH_2Cl_2$ (130 mL), and $Et_3N$ (1.2 mL, 8.7 mmol). tert-Butyldimethylsilyl trifluoromethanesulfonate (2.0 mL, 8.7 mmol) was added by syringe in one portion and the mixture was allowed to stir for 10 min. At this time, the mixture was diluted with a saturated aqueous solution of $NaHCO_3$ (100 mL) and the layers were partitioned. The aqueous layer was washed with $CH_2Cl_2$ (2×75 mL) and the combined organic layers were dried over MgSO$_4$, filtered, and concentrated to furnish a yellow solid. The solid was purified by silica gel column chromatography (dry load method, gravity elution, 15:1 petroleum ether:Et$_2$O) and was then (still yellow) dissolved in a minimal amount of boiling petroleum ether and cooled to −15° C. (dry ice/acetone bath). The suspension was filtered while cold and dried under reduced pressure to afford 83 (2.9 g, 5.10 mmol, 76% yield) as a white solid. m.p.=158-159° C.; IR (neat) 3514 (m), 2924 (s), 2854 (m), 1441 (s), 1355 (w), 1321 (w), 1251 (s), 1210 (m), 1190 (m), 1161 (m), 1078 (w), 1022 (m), 980 (w), 966 (m), 864 (m), 839 (s), 797 (m), 781 (s), 702 (m) cm$^{-1}$; $^1$H NMR (400 MHz, CDCl$_3$) δ7.32 (1H, s), 7.21 (1H, s), 5.11 (1H, s), 2.80-2.65 (4H, m), 2.45-2.29 (2H, m), 2.17-1.93 (2H, m), 1.80-1.53 (8H, m), 0.81 (9H, s), 0.11 (3H, s), −0.34 (3H, s); $^{13}$C NMR (100 MHz, CDCl$_3$) δ 148.1, 147.4, 137.1, 136.9, 134.1, 132.6, 131.8, 131.5, 128.2, 124.9, 112.7, 107.4, 29.4, 29.3, 27.3, 27.1, 26.3, 23.2, 23.1, 23.0, 22.9, 18.8, −2.7, −4.0. HRMS (ESI$^+$) [M+H]$^+$ calcd for C$_{26}$H$_{35}$Br$_2$O$_2$Si: 565.0773. found: 565.0755; [α]$_D^{20}$+59.4 (c=1.00, CHCl$_3$).

(R)-3,3'-Dichloro-2'-(tert-butyldimethylsilyloxy)-5,5',6,6',7,7',8,8'-octahydro-1,1'-binaphthyl-2-ol (86)

Figure 32:
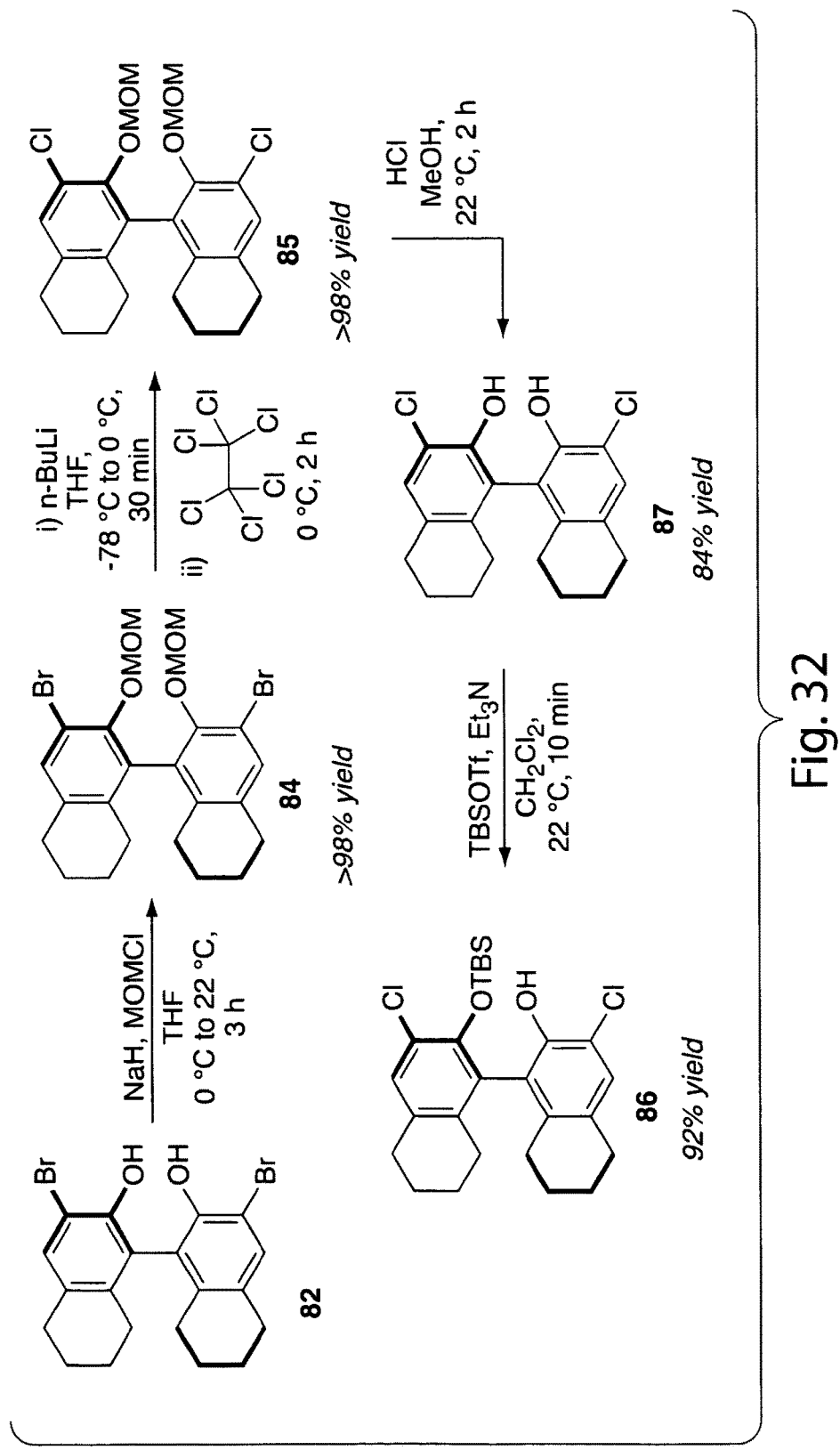
FIG. 32 shows the synthesis of an oxygen-containing ligand lacking a plane of symmetry from (R)-3,3'-dibromo-5,5',6,6',7,7',8,8'-octahydro-1,1'-binaphthyl-2,2'-diol.

(FIG. 32) A 25-mL round-bottom flask with magnetic stir bar was charged with NaH (60% dispersion in mineral oil, 354 mg, 8.80 mmol) and THF (5 mL). The resulting suspension was allowed to cool to 0° C. (ice bath) while stirring. A solution of diol 82 (1.00 g, 2.20 mmol) in THF (4.5 mL) was added to the original mixture by cannula; the vial containing the diol was rinsed with THF (0.6 mL), which was similarly transferred to the mixture. After 1 a solution was allowed to warm to 22° C. After 3 h, the reaction was quenched by the addition of H$_2$O (10 mL). The layers were partitioned and the aqueous layer was washed with EtOAc (3×10 mL). The combined organic layers were dried over MgSO$_4$, filtered, and concentrated. The resulting yellow oil was purified by silica gel column chromatography (15:1 petroleum ether:Et$_2$O) to afford 84 (1.19 g, 2.20 mmol, >98% yield) as a colorless oil. $^1$H NMR (400 MHz, CDCl$_3$) δ7.32 (2H, br s), 4.93 (2H, d, J$_{AB}$=6.0 Hz), 4.84 (2H, d, J$_{AB}$=6.0 Hz), 2.85 (6H, s), 2.79-2.72 (4H, m), 2.40 (2H, ddd, J=17.2, 6.4, 6.4 Hz), 2.11 (2H, ddd, J=17.2, 6.0, 6.0 Hz), 1.78-1.62 (8H, m).

A 50-mL round-bottom flask with magnetic stir bar was charged with bis(methoxymethyl ether) 84 (562 mg, 1.00 mmol) and Et$_2$O (16 mL). The mixture was allowed to cool to −78° C. (dry ice/acetone bath), after which n-butyllithium (2.24 mL, 1.24 M in hexanes, 3.10 mmol) was added dropwise by syringe. The resulting mixture was allowed to warm to 0° C. (ice bath) and stir for 30 min, over which time a white precipitate formed. A solution of hexachloroethane (862 mg, 3.60 mmol) in Et$_2$O (9 mL) was added to the mixture by cannula; the vial containing hexachloroethane was rinsed with Et$_2$O (1 mL), which was similarly transferred. After 2 h, the reaction was quenched by the addition of H$_2$O (10 mL) and the mixture allowed to warm to 22° C. The layers were partitioned and the aqueous layer was washed with EtOAc (3×10 mL). The combined organic layers were washed with a saturated aqueous solution of NaCl (50 mL), dried over MgSO$_4$, filtered, and concentrated. The resulting brown oil was purified by silica gel chromatography (30:1 to 15:1 petroleum ether:Et$_2$O) to furnish 85 (550 mg) as light brown, viscous oil. $^1$H NMR (400 MHz, CDCl$_3$) δ7.14 (2H, br s), 4.94 (2H, d, J$_{AB}$=6.4 Hz), 4.83 (2H, d, J$_{AB}$=6.0 Hz), 2.89 (6H, s), 2.79-2.72 (4H, m), 2.41 (2H, ddd, J=17.2, 6.4, 6.4 Hz), 2.12 (2H, ddd, J=17.2, 6.4, 6.4 Hz), 1.78-1.62 (8H, m).

A 25-mL round-bottom flask with magnetic stir bar was charged with bis(methoxymethyl ether) 85 (550 mg) and MeOH (6 mL). Hydrogen chloride (610 □L, 4.00 M in dioxane, 2.40 mmol) was added dropwise by syringe. After 2 h, the mixture was diluted with H$_2$O (15 mL) and was subsequently washed with EtOAc (4×30 mL). The combined organic layers were washed with a saturated aqueous solution of NaCl (50 mL), dried over MgSO$_4$, filtered, and concentrated to afford 87 (374 mg) as light brown, viscous oil, which was carried forward without purification. $^1$H NMR (400 MHz, CDCl$_3$) δ7.13 (2H, br s), 5.18 (2H, br s), 2.81-2.67 (4H, m), 2.36-2.25 (2H, m), 2.16-2.05 (2H, m), 1.79-1.60 (8H, m).

Protection of diol 87 as the tert-butyldimethylsilyl ether was accomplished through the procedure used in the synthesis of alcohol 83. The resulting yellow foam was purified by silica gel chromatography (15:1 petroleum ether:Et$_2$O) to provide 86 (440 mg, 0.920 mmol, 92.0% yield over 3 steps) as off-white solid. m.p.=163-164° C.; IR (neat) 3537 (m), 2929 (s), 2883 (s), 2857 (s), 1451 (m), 1406 (m), 1356 (m), 1340 (w), 1318 (m), 1290 (s), 1272 (s), 1256 (s), 1212 (m), 1177 (m), 1162 (m), 1082 (m), 1036 (m), 984 (m), 968 (m), 858 (s), 841 (s), 801 (s), 760 (s) cm$^{-1}$; $^1$HNMR (400 MHz, CDCl$_3$) δ7.14 (1H, s), 7.07 (1H, s), 5.12 (1H, s), 2.81-2.66 (4H, m), 2.45-2.31 (2H, m), 2.19-1.98 (2H, m), 1.79-1.56 (8H, m), 0.78 (9H, s), 0.12 (3H, s), −0.26 (3H, s); $^{13}$C NMR (100 MHz, CDCl$_3$) δ 146.9, 146.4, 136.1, 135.9, 131.9, 130.8, 130.7, 128.7, 128.1, 124.8, 122.6, 117.4, 29.4, 29.3, 27.2, 26.9, 25.9, 23.1, 23.0, 22.9, 22.8, 18.6, −3.3, −4.3; HRMS (ESI$^+$) [M+H]$^+$ calcd for C$_{26}$H$_{35}$C$_{12}$O$_2$Si: 477.1783. found: 477.1768; [α]$_D^{20}$+104 (c=0.906, CHCl$_3$).

Stereoselective in situ-Generation of Monoalkoxide Complexes, General Procedure:

A 4-mL vial with magnetic stir bar was charged with 22b (5.4 mg, 9.1 umol), 23 (5.1 mg, 9.1 umol), and C$_6$D$_6$ (500 uL) in an N$_2$-filled glovebox. The vial was tightly capped and the mixture was allowed to stir for 1 h, after which it was transferred to a screw-cap NMR tube by pipet. The NMR tube was tightly capped and sealed with Teflon tape. For in situ-generated complexes, only the diagnostic signals of the alpha-carbon of the syn-alkylidenes are reported. $^1$H NMR (400 MHz, C$_6$D$_6$) δ 12.92 (1H, s), 11.58 (1H, s); d.r.=1:7 (entry 2, Table 1). The diastereomeric ratio (d.r.) was measured by 400 MHz 1H NMR analysis and reflects the ratio of syn-alkylidene isomers. In certain cases, anti-alkylidene isomers can also be detected, usually representing <5% of the mixture. NMR data are summarized in Table 12.

TABLE 12

Summary of $^1$H NMR data.

| entry | Complex | Chemical Shift (ppm) | d.r. |
| --- | --- | --- | --- |
| 1 | 27a | 12.38, 11.73 | 1:19 |
| 2 | 27b | 12.92, 11.58 | 1:7 |
| 3 | 28a | 12.86, 12.84 | >20:1 |
| 4 | 28b | 12.90, 12.42 | 1:7 |
| 5 | 28c | 13.06, 12.54 | 1:5 |

Synthesis of Isolated, Diastereomerically Pure Complex 28b:

In an N$_2$-filled glovebox, a 25-mL pear-shaped flask with magnetic stir bar was charged with Mo-bis(pyrrolide) complex 22b (150 mg, 254 umol) and Et$_2$O (4.0 mL). The flask was sealed and allowed to cool to −50° C. (glovebox freezer). An 8-mL vial was charged with alcohol 83 (144 mg, 254 umol) and Et$_2$O (0.6 mL). The vial was tightly capped and allowed to cool to −50° C. (glovebox freezer). The Mo-bis(pyrrolide) solution was allowed to stir, and the chilled alcohol solution was added to it by pipet; the vial containing the alcohol was rinsed with Et$_2$O (0.6 mL, −50° C.), which was similarly transferred to the reaction mixture, and the resulting solution was allowed to warm to 22° C. As the reaction progressed, the mixture turned from bright yellow to red. After 1 h at 22° C., volatiles were removed under reduced pressure, and the resulting residue red solid was dissolved in n-pentane (5 mL), which was subsequently removed in vacuo to afford a red-orange powder (this procedure can be repeated until a powder is obtained). The powder was dissolved in n-pentane (2 mL) with vigorous stirring; once all of the solid had dissolved, the flask was sealed and allowed to cool to −50° C. (glovebox freezer) for 12 h, after which large red crystals appeared. The crystals were collected by vacuum filtration and washed with cold n-pentane (~5 mL, −50° C.) to afford diastereomerically pure 28b (contains 1 molecule of n-pentane per 1 molecule of 28b) (170 mg, 150 umol, 59.0% yield). $^1$H NMR (400 MHz, C$_6$D$_6$ δ. 12.42 (1H, s), 7.31 (1H, s), 7.29-7.27 (1H, m), 7.27-7.24 (1H, m), 7.14-7.05 (3H, m), 7.03-6.98 (4H, m), 5.81 (2H, s), 4.60-3.00 (2H, br), 2.59-1.81 (13H, m), 1.81 (3H, s), 1.71 (3H, s), 1.60-1.35 (8H, m), 1.30-1.03 (13H, m), 0.99 (9H, s), 0.06 (3H, s), 0.03 (3H, s); $^1$H NMR (400 MHz, CDCl$_3$ δ 12.23 (1H, s), 7.34-7.28 (2H, m), 7.25-7.05 (7H, m), 6.97 (1H, s), 5.54 (2H, s), 4.00-3.10 (2H, br), 2.81-2.67 (2H, m), 2.51-2.32 (2H, m), 2.31-2.13 (3H, m), 2.12-2.02 (1H, m), 2.00-1.40 (16H, m), 1.77 (3H, s), 1.67 (3H, s), 1.38-1.22 (4H, m), 1.30 (6H, d, J=6.8 Hz), 0.80 (9H, s), −0.17 (6H, s); $^{13}$C NMR (100 MHz, CDCl$_3$) δ 291.7, 157.4, 153.3, 147.9, 147.1, 136.4, 134.9, 134.2 (br), 133.8, 132.5, 132.0, 131.7, 129.3, 128.4, 128.3, 128.2, 126.3, 126.0, 123.1, 112.4, 110.3, 108.4 (br), 55.2, 34.3, 31.7, 29.9, 29.4, 28.7, 28.5, 28.4, 27.6, 26.2, 24.0 (br), 23.7, 23.1, 23.0, 22.8, 22.6, 22.5, 18.8, 16.2 (br), 14.2, −3.0, −3.1; Anal. calcd for C$_{59}$H$_{82}$Br$_2$MoN$_2$O$_2$Si: C, 62.43; H, 7.28; N, 2.47. found: C, 62.40; H, 7.22; N, 2.77.

Representative Procedure for In Situ-Generation of Catalyst 28b:

In an N$_2$-filled glovebox, a 4-mL vial containing a magnetic stir bar was charged with 22b (10.0 mg, 16.9 umol), 83 (9.40 mg, 16.9 umol), and C$_6$H$_6$ (845 uL, 0.02 M); the mixture became brilliantly orange. The vial was capped and the solution was allowed to stir for 1 h at 22° C. The catalyst solution was transferred to the reaction mixture by a syringe (dried at 65° C. under vacuum).

General Procedure for Catalytic Enantioselective Olefin Metathesis with In Situ-Generated Catalyst:

In an N$_2$-filled glovebox, an oven-dried 4-mL vial equipped with a magnetic stir bar was charged with substrate and then C$_6$H$_6$. The appropriate amount of the chiral complex, prepared as mentioned above, was added (final substrate concentration=0.1 M); the resulting solution was allowed to stir for the required period of time. The reaction was then quenched by exposure to air and concentrated in vacuo (% conversion determined by 400 MHz $^1$H NMR analysis). Purification was performed by silica gel chromatography. The enantiomeric purity of the product of the olefin metathesis reaction was determined by chiral GLC or HPLC analysis in comparison with authentic racemic material.

(S)-4-Methyl-2-(2-methylallyl)-1-phenyl-1,2,3,6-tetrahydropyridine (39)

Following the general procedure, substrate 38 (21.1 mg, 0.0830 mmol) in C$_6$H$_6$ (790 μL) was treated with 1 mol % of in situ-generated chiral complex 28b (41.0 μL, 0.02 M, 0.830 μmol; final substrate concentration equals 0.1 M). The vial was capped and the solution was allowed to stir for 30 min. At this time, the reaction was quenched by exposure to air and the mixture concentrated. The unpurified brown solid was dissolved in minimal MeOH (0.5 mL), and KF (4.80 mg, 0.083 mmol) was added (to desilylate the phenol 83, which has the same R$_f$ as 39). The mixture was allowed to stir for 30 min. Silica gel was added and the mixture concentrated and purified by silica gel column chromatography (50:1 pet ether:Et$_2$O) to afford 39 (17.2 mg, 0.0760 mmol, 91.0% yield) as a white solid. The physical and spectral data were identical to those previously reported for compound 39. m.p.=55-57° C.; $^1$H NMR (400 MHz, CDCl$_3$): δ7.91-7.87 (2H, m), 6.79-6.74 (1H, m), 5.54-5.50 (1H, m), 4.79-4.75 (1H, m), 4.69-4.66 (1H, m), 4.23 (1H, dddd, J$_{ABX}$=10.0, 5.2, 4.0, 0.8 Hz), 3.80 (1H, app dt, J$_{ABX}$=16.8, 1.6 Hz), 3.51 (1H, ddddd, J$_{ABX}$=16.8, 3.6, 2.4, 2.0, 2.0 Hz), 2.40 (1H, br d, J$_{AB}$=16.8 Hz), 2.21 (1H), dd, J$_{AB}$=13.2, 10.6 Hz), 2.07 (1H, dd, J$_{ABX}$=13.6, 4.0 Hz), 2.03 (1H, d, J$_{AB}$=17.2 Hz), 1.76 (3H, br s), 1.74 (3H, d, J=0.8 Hz); HRMS (ESI$^+$) [M+H]$^+$ calcd for C$_{16}$H$_{22}$N: 228.1752. found: 228.1755; [α]$_D^{20}$−169 (c=0.500, CHCl$_3$) for a sample of 93% e.e. (96.5:3.5 e.r.) [α]$_D^{20}$ +181 (c=0.950, CHCl$_3$) for a sample of 98% e.e. (99:1 e.r.)]. The enantiomeric purity of 39 (93% e.e.; 96.5:3.5 e.r.) was determined by chiral GLC analysis (CDGTA column, 20 psi, 130° C.) in comparison with authentic racemic material. The enantiomer formed in this reaction was assigned through inference with that detailed previously.

Larger-Scale ARCM with 0.5 Mol % In Situ-Generated Complex 28b:

In an N$_2$-filled glovebox, a 30-mL vial with magnetic stir bar was charged with substrate 38 (803 mg, 3.14 mmol) and a solution of in situ-generated complex 28b (393 μL, 0.04 M, 16.0 μmol). The resulting mixture was allowed to stir for 15 min. At this time, the reaction was quenched by exposure to air and the mixture concentrated. The resulting brown solid was dissolved in 1:1 MeOH:Et$_2$O (4 mL) and KF (100 mg, 1.70 mmol) added (to desilylate the phenol 83, which has the same R$_f$ as 39). The mixture was allowed to stir for 30 min, after which silica gel was added and the mixture concentrated and purified by silica gel column chromatography (50:1 pet ether:Et$_2$O) to afford 39 (690 mg, 3.03 mmol, 96.0% yield) as a white solid. The enantiomeric purity of 39 (91% e.e.; 95.5:4.5 e.r.) was determined by chiral GLC analysis (CDGTA column, 20 psi, 130° C.) based on comparison with authentic racemic material.

(S)-4-Methyl-2-(2-methylallyl)-1,2,3,6-tetrahydropyridine (67)

Following the general procedure, substrate 66 (20.0 mg, 0.0330 mmol) in C$_6$H$_6$ (976 μL) was treated with 2.5 mol % of in situ-generated chiral complex 28b (two batches of 1 mol % (56.0 μL, 0.02 M, 1.10 μmol), and one batch of 0.5 mol % 28b (28.0 μL, 0.02 M, 0.550 μmol; added every ~20 min) and allowed to stir for 1 h (final substrate concentration=0.1 M). The resulting brown oil was purified by silica gel chromatography (50:1 CH$_2$Cl$_2$:MeOH washed with 2% v/v concentrated aqueous NH$_4$OH) to afford 67 (15.0 mg, 0.0990 umol, 89.0% yield) as a clear oil (volatile). The physical and spectral data are identical to those previously reported for compound 67. $^1$H NMR (400 MHz, CDCl$_3$): δ5.43-5.38 (1H, m), 4.83-4.81 (1H, m), 4.78-4.76 (1H, m), 3.40-3.28 (2H, m), 2.84 (1H, dddd, J$_{AX}$=9.6, 7.6, 6.0, 4.4 Hz), 2.16-2.11 (2H, m), 1.90-1.62 (3H, m), 1.73 (3H, s), 1.67

(3H, s); HRMS (ESI+) [M+H]+ calcd for $C_{10}H_{18}N$: 152.1439. found: 152.1446; $[\alpha]_D^{20}$+71.6 (c=0.993, CHCl$_3$) for a sample of 67% e.e. (83.5:16.5 e.r.) $[\alpha]_D^{20}$+77.0 (c=1.00, CHCl$_3$) for a sample of 87% e.e. (93.5:6.5 e.r.)]. The enantiomeric purity of 67 (67% e.e.; 83.5:16.5 e.r.) was determined by acylation to the corresponding amide as previously reported and chiral GLC analysis (CDGTA column, 15 psi, 120° C.) in comparison with authentic racemic material. The enantiomer formed in this reaction was assigned through inference to product 39.

(S)-7-Methyl-8a-(2-methylallyl)-8,8a-dihydroindolizin-3(1H,2H,5H)-one (49)

Following the general procedure, substrate 48 (10.0 mg, 0.043 mmol) in $C_6H_6$ (364 μL) was treated with 3 mol % of in situ-generated complex 28c (three batches of 1 mol % (21.0 μL, 0.02 M, 0.430 μmol) every 20 min; final substrate concentration=0.1 M) and allowed to stir for 1 h. The resulting oil was purified by silica gel chromatography (2:1 EtOAc:pet ether) to afford 49 (8.00 mg, 0.0390 umol, 91.0% yield) as a colorless oil. The physical and spectral data were identical to those previously reported for compound 49. $^1$H NMR (400 MHz, CDCl$_3$): δ 5.41-5.37 (1H, m), 4.90 (1H, dddd, $J_{ABx}$=2.0, 1.5, 1.5, 1.5 Hz), 4.73-4.71 (1H, m), 4.32 (1H, br d, $J_{AB}$=18.4 Hz), 3.43 (1H, d, $J_{AB}$=18.4 Hz), 2.49-2.22 (5H, m), 2.14-2.03 (2H, m), 1.83-1.74 (1H, m), 1.75 (3H, s), 1.70 (3H, s); HRMS (ESI+) [M+H]+ calcd for $C_{13}H_{20}NO$: 206.1545. found: 206.1551; $[\alpha]_D^{20}$–109 (c=0.513, CHCl$_3$) for a sample of 91% e.e. (95.5:4.5 e.r.) $[\alpha]_D^{20}$+103 (c=1.00, CHCl$_3$) for a sample of 98% e.e. (99:1 e.r.)]. The enantiomeric purity of 49 (91% e.e.; 95.5:4.5 e.r.) was determined by chiral GLC analysis (CDGTA column, 20 psi, 140° C.) in comparison with authentic racemic material. The enantiomer formed in this reaction was assigned through inference with that detailed previously.

(S)-7-Methyl-8a-(2-methylallyl)-1,2,3,5,8,8a-hexahydroindolizine (45)

Following the general procedure, substrate 44 (20.0 mg, 0.0910 mmol) in $C_6H_6$ (865 μL) was treated with 1 mol % of in situ-generated chiral complex 28b (46.0 μL, 0.02 M, 0.910 μmol; final substrate concentration=0.1 M) and allowed to stir for 1 h. The brown oil was purified by silica gel chromatography (50:1 CH$_2$Cl$_2$:MeOH washed with 2% v/v concentrated aqueous NH$_4$OH) to afford 45 (17.3 mg, 0.0900 mmol, 99.0% yield) as a colorless oil (volatile). The physical and spectral data were identical to those previously reported for compound 45. IR (neat): 3071 (w), 2963 (s), 2916 (s), 2880 (s), 1639 (m), 1445 (s), 1375 (m), 1356 (m), 1101 (m), 1161 (m), 887 (s) cm$^{-1}$; $^1$H NMR (400 MHz, CDCl$_3$): δ 5.41-5.37 (1H, m), 4.81 (1H, dddd, $J_{ABx}$=2.8, 1.2, 1.2, 1.2 Hz), 4.64-4.62 (1H, m), 3.32-3.16 (2H, m), 2.86-2.72 (2H, m), 2.25 (1H, d, J=12.8 Hz), 1.95-1.77 (6H, m), 1.76 (3H, s), 1.66 (3H, s), 1.53 (1H, ddd, J=11.6, 7.7, 7.6 Hz); $^{13}$C NMR (100 MHz, CDCl$_3$): δ 143.9, 131.4, 117.7, 114.3, 60.3, 50.1, 45.8, 39.5, 36.5, 34.4, 24.7, 23.6, 20.2; HRMS (ESI+) [M+H]+ calcd for $C_{13}H_{22}N$: 192.1752. found: 192.1760; $[\alpha]_D^{20}$–92.3 (c=1.05, CHCl$_3$) for a sample of 92% e.e. (96:4 e.r.). The enantiomeric purity of 45 (92% e.e.; 96:4 e.r.) was determined by oxidation to the corresponding lactam 49 as previously reported, and chiral GLC analysis (CDGTA column, 20 psi, 140° C.) in comparison with authentic racemic material. The enantiomer formed in this reaction was assigned through inference to product 49.

(S)-8-methyl-9a-(2-methylallyl)-2,3,5,6,9,9a-hexahydro-1H-pyrrolo[1,2-a]azepine (47)

Following the general procedure, substrate 46 (20.0 mg, 0.0860 mmol) in $C_6H_6$ (728 μL) was treated with 3 mol % of in situ-generated chiral complex 28c (three batches of 1 mol % (43.0 μL, 0.02 M, 2.57 μmol) approximately every 20 min; final substrate concentration=0.1 M) and allowed to stir for 1 h. The resulting brown oil was purified by silica gel chromatography (50:1 CH$_2$Cl$_2$:MeOH washed with 2% v/v concentrated aqueous NH$_4$OH) to afford 47 (15.2 mg, 0.0740 mmol, 86.0% yield) as a colorless oil. The physical and spectral data were identical to those previously reported. $^1$H NMR (400 MHz, CDCl$_3$): δ 5.49-5.44 (1H, m), 4.82 (1H, dddd, $J_{ABX}$=2.8, 1.6, 1.6, 1.6 Hz), 4.71-4.68 (1H, m), 2.96 (1H, ddd, J=13.2, 9.6, 2.4 Hz), 2.90-2.76 (3H, m), 2.44 (1H, d, $J_{AB}$=15.6 Hz), 2.41-2.31 (1H, m), 2.30 (1H, d, $J_{AB}$=14.0 Hz), 2.13 (1H, d, $J_{AB}$=13.6 Hz), 2.13-2.04 (1H, m), 2.02 (1H, d, $J_{AB}$=15.6 Hz), 2.02-1.95 (1H, m), 1.81 (3H, s), 1.76-1.66 (2H, m), 1.70 (3H, s), 1.45 (1H, ddd, $J_{ABX}$=12.0, 9.2, 9.2 Hz); HRMS (ESI+) [M+H]+ calcd for $C_{14}H_{24}N$: 206.1909. found: 206.1915 $[\alpha]_D^{20}$–63.9 (c=0.973, CHCl$_3$) for a sample of 81% e.e. (90.5:9.5 e.r.). The enantiomeric purity of 47 (81% e.e.; 90.5:9.5 e.r.) was determined by oxidation to the corresponding lactam as previously reported and chiral GLC analysis (CDGTA column, 20 psi, 140° C.) in comparison with authentic racemic material. The enantiomer formed in this reaction was assigned through inference to product 49.

(S)-4-Methyl-2-(2-methylallyl)-1-phenyl-2,3,6,7-tetrahydro-1H-azepine (41)

Following the general procedure, substrate 40 (10.7 mg, 0.040 mmol) in $C_6H_6$ (380 μL) was treated with 1 mol % of in situ-generated catalyst 28c (20.0 μL, 0.02 M, 0.400 μmol) and allowed to stir for 1 h. The unpurified brown oil was dissolved in MeOH (0.5 mL) and KF (2.30 mg, 0.040 mmol) was added (to desilylate the phenol 86, which has the same $R_f$ as 41). The mixture was allowed to stir for 30 min. Silica gel was added and the mixture concentrated and purified by silica gel column chromatography (50:1 pet ether:Et$_2$O) to afford 41 (8.30 mg, 0.340 mmol, 86.0% yield) as a colorless oil. The physical and spectral data were identical to those previously reported. $^1$H NMR (400 MHz, CDCl$_3$): δ 5.41-5.37 (1H, m), 6.73 (2H, d, J=8.4 Hz), 6.63 (1H, dd, J=7.2, 7.2 Hz), 5.31-5.27 (1H, m), 4.81-4.38 (1H, m), 4.80-4.78 (1H, m), 4.03 (1H, dddd, J=9.2, 9.2, 4.4, 4.4 Hz), 3.72 (1H, ddd, $J_{ABX}$=15.6, 12.0, 3.6 Hz), 3.52 (1H, ddd, $J_{ABX}$=15.6, 4.4, 4.4 Hz), 2.64-2.44 (3H, m), 2.27-2.13 (3H, m), 1.82 (3H, s), 1.70 (3H, d, J=1.6 Hz); HRMS (ESI+) [M+H]+ calcd for $C_{17}H_{24}N$: 242.1909. found: 242.1901; $[\alpha]_D^{20}$+205 (c=1.00, CHCl$_3$) for a sample of 93% e.e. (96.5:3.5 e.r.) $[\alpha]_D^{20}$–209 (c=1.00, CHCl$_3$) for a sample of 95% e.e. (97.5:2.5 e.r.)]. The enantiomeric purity of 41 (93% e.e.; 96.5:3.5 e.r.) was determined by chiral HPLC analysis (Chiralpak OD column, 100% Hexanes, 1.0 mL/min, 254 nm) in comparison with authentic racemic material. The enantiomer formed in this reaction was assigned through inference to product 39.

(S)-7-(4-Bromophenyl)-2,2,5-trimethyl-7-(2-methylallyl)-2,3,6,7-tetrahydro-1,2-oxasilepine (56)

Following the general procedure, substrate 55 (14.8 mg, 0.0380 mmol) in $C_6H_6$ (360 μL) was treated with 1 mol % of in situ-generated chiral complex 28c (19.0 μL, 0.02 M, 0.380 μmol; final substrate concentration=0.1 M) and allowed to stir for 1 h. The resulting brown oil was purified by silica gel chromatography (100% petroleum ether) to afford 56 (11.6 mg, 0.0320 mmol, 84.0% yield) as a colorless oil. The physical and spectral data were identical to those previously reported. $^1$H NMR (400 MHz, CDCl$_3$): δ 7.41-7.37 (2H, m), 7.26-7.24 (2H, m), 5.59 (1H, ddd, J=7.2, 7.2, 1.2 Hz), 4.62 (1H, br s), 4.46 (1H, br s), 2.77 (1H, d, $J_{AB}$=14.0 Hz), 2.62 (1H, d, $J_{AB}$=17.6 Hz), 2.59 (1H, d, $J_{AB}$=18.0 Hz), 2.48 (1H, d, $J_{AB}$=14.0 Hz), 1.58 (1H, dd, $J_{ABX}$=14.8, 6.0 Hz), 1.50 (3H, s), 1.44-1.37 (1H, m), 1.35 (3H, s), 0.24 (3H, s), 0.20 (3H, s); HRMS (ESI$^+$) [M+H]$^+$ calcd for C$_{18}$H$_{26}$BrOSi: 365.0936. found: 365.0945 $[α]_D^{20}$–130 (c=0.800, CHCl$_3$) for a sample of 88% e.e. (94:6 e.r.). The enantiomeric purity of 56 (88% e.e.; 94:6 e.r.) was determined by protiodesilylation of oxasilepine 56 as previously described and chiral HPLC analysis (Chiralcel OD-(R), 99:1 hexanes:i-PrOH, 1.0 mL/min, 228 nm) in comparison with authentic racemic material. The enantiomer formed in this reaction was assigned through inference with that detailed previously.

Tetradehydro (+)-quebrachamine (61)

Following the general procedure, triene 60 (10.1 mg, 0.033 mmol) in C$_6$H$_6$ (50 μL) was treated with 1 mol % of in situ-generated chiral complex 28c (16.5 μL, 0.02 M, 0.331 μmol; final substrate concentration=0.5 M) and allowed to stir for 1 h. The resulting brown oil was purified by silica gel chromatography (8:1 petroleum ether:Et$_2$O washed with 2% v/v concentrated aqueous NH$_4$OH) to afford 61 (7.70 mg, 0.0277 mmol, 84.0% yield) as a colorless oil. IR (Neat): 3400 (s), 3023 (w), 2912 (s), 2846 (m), 2783 (m), 2727 (m), 1632 (m), 1462 (s), 1435 (m), 1333 (m), 1299 (m), 1164 (m), 999 (m), 911 (m), 740 (s) cm$^{-1}$; $^1$H NMR (400 MHz, CDCl$_3$): δ 7.78 (1H, br s), 7.51-7.47 (1H, m), 7.31-7.28 (1H, m), 7.13-7.05 (2H, m), 5.90 (1H, ddd, J=9.9, 4.8, 1.5 Hz), 5.61 (1H, dd, $J_{ABX}$=17.5, 10.5 Hz), 5.44 (1H, ddd, J=9.9, 4.0, 2.0 Hz), 4.92 (1H, dd, J=6.8, 1.3 Hz), 4.88 (1H, s), 3.73 (1H, ddd, $J_{ABX}$=14.2, 10.5, 1.5 Hz), 3.32-3.25 (1H, m), 3.13-3.07 (1H, m), 2.88-2.82 (1H, m), 2.80-2.64 (4H, m), 2.42-2.33 (2H, m), 2.01-1.86 (2H, m); $^{13}$C NMR (100 MHz, CDCl$_3$): δ 145.8, 139.3, 135.5, 132.2, 128.9, 127.5, 120.9, 119.0, 118.0, 112.0, 110.1, 110.1, 59.3, 54.1, 52.0, 43.6, 40.1, 25.5, 23.0; HRMS (ESI$^+$) [M+H]$^+$ calcd for C$_{19}$H$_{23}$N$_2$: 279.1861, found: 279.1854 $[α]_D^{20}$ +99.2 (c=0.513, CHCl$_3$) for a sample of 96% e.e. (98:2 e.r.). The enantiomeric purity of 2 (96% e.e.; 98:2 e.r.) was determined by chiral HPLC analysis (Chiralpak OD, 95:5 hexanes:i-PrOH, 1.0 mL/min, 254 nm) in comparison with authentic racemic material. The absolute stereochemistry was determined through subsequent catalytic hydrogenation to obtain (+)-quebrachamine (see below).

(+)-Quebrachamine:

A 4-mL vial containing a magnetic stir bar was charged with diene 61 (5.40 mg, 19.4 umol) and 5 mol % PtO$_2$ (0.220 mg, 194 uL, 0.1 M heterogeneous dispersion in EtOH). A septum was used to cap the vial and the stirring suspension was treated with 1 atm H$_2$, administered through a balloon. After a brief purge to ensure exchange of the atmosphere with H$_2$, the mixture was allowed to stir for 1 h. At this time, the mixture was pushed through a plug of silica gel and eluted with CH$_2$Cl$_2$ washed with 2% v/v concentrated aqueous NH$_4$OH (10 mL). Removal of the volatiles furnished a colorless oil that was purified by silica gel chromatography (CH$_2$Cl$_2$ washed with 2% v/v concentrated aqueous NH$_4$OH) to afford (+)-quebrachamine (5.30 mg, 18.8 umol, 97.0% yield) as a white solid. m.p.=143-144° C. [Lit. 147-149° C.]; IR (Neat): 3403 (s), 2957 (m), 2921 (s), 2850 (s), 2784 (m), 2730 (m), 1462 (s), 1440 (m), 1348 (w), 1131 (w), 741 (s) cm$^{-1}$; $^1$HNMR (400 MHz, CDCl$_3$): δ 7.70 (1H, br s), 7.49-7.47 (1H, m), 7.29-7.26 (1H, m), 7.09 (1H, td, J=7.2, 1.6 Hz), 7.06 (1H, td, J=7.2, 1.6 Hz), 3.25 (1H, bs d, J=11.6 Hz), 2.94 (1H, ddd, $J_{ABX}$=14.8, 11.6, 4.8 Hz), 2.84 (1H, ddd, $J_{ABX}$=14.8, 4.4, 2.8 Hz), 2.74 (1H, ddd, $J_{ABX}$=15.6, 10.4, 2.0 Hz), 2.67 (1H, ddd, $J_{ABX}$=15.2, 7.2, 2.0 Hz), 2.48-2.43 (1H, m), 2.41 (1H, dd, J=4.4, 2.8 Hz), 2.33 (1H, td, J=11.6, 4.4 Hz), 2.25 (1H, td, J=11.6, 11.6, 2.8 Hz), 1.92 (1H, ddd, J=14.0, 6.8, 2.0 Hz), 1.65-1.53 (2H, m), 1.50 (1H, d, J=11.6 Hz), 1.33-1.08 (5H, m), 0.85 (3H, t, J=7.2 Hz); $^{13}$C NMR (100 MHz, CDCl$_3$): δ 140.0, 135.0, 129.1, 120.3, 118.8, 117.5, 110.1, 108.9, 56.9, 55.2, 53.4, 37.3, 34.9, 33.6, 32.2, 22.8, 22.6, 22.1, 7.9; HRMS (ESI$^+$) [M+H]$^+$ calcd for C$_{19}$H$_{27}$N$_2$: 283.2174, found: 283.2183; $[α]_D^{20}$+103 (c=0.353, CDCl$_3$) for a sample of 96% e.e. (98:2 e.r.) $[α]_D^{20}$+117 (c=0.180, CHCl$_3$)].

Example 13

Figure 36:
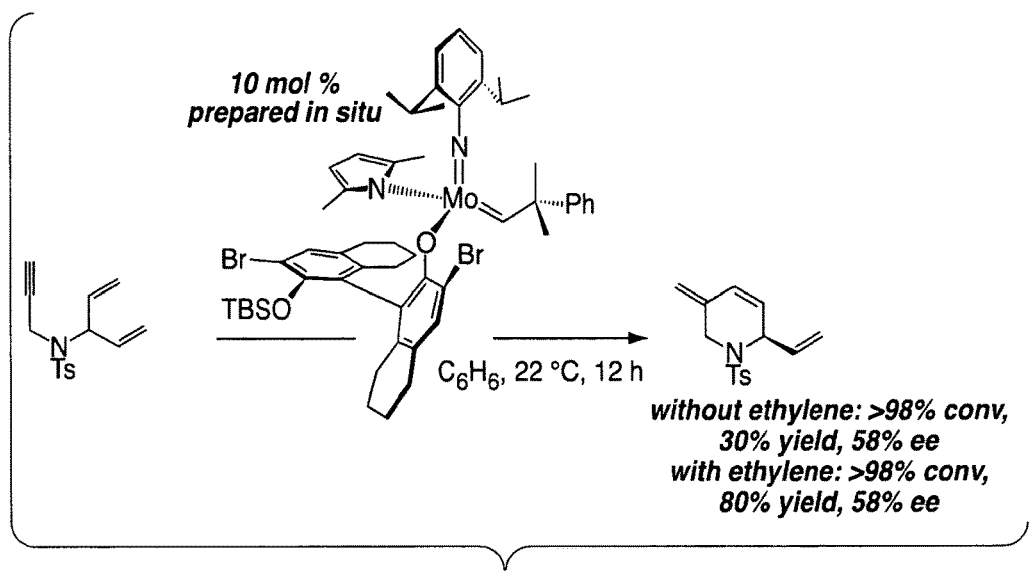
FIG. 36 shows the intramolecular cross-metathesis reaction of 4-methyl-N-(penta-1,4-dien-3-yl)-N-(prop-2-ynyl)benzenesulfonamide.
Figure 37:
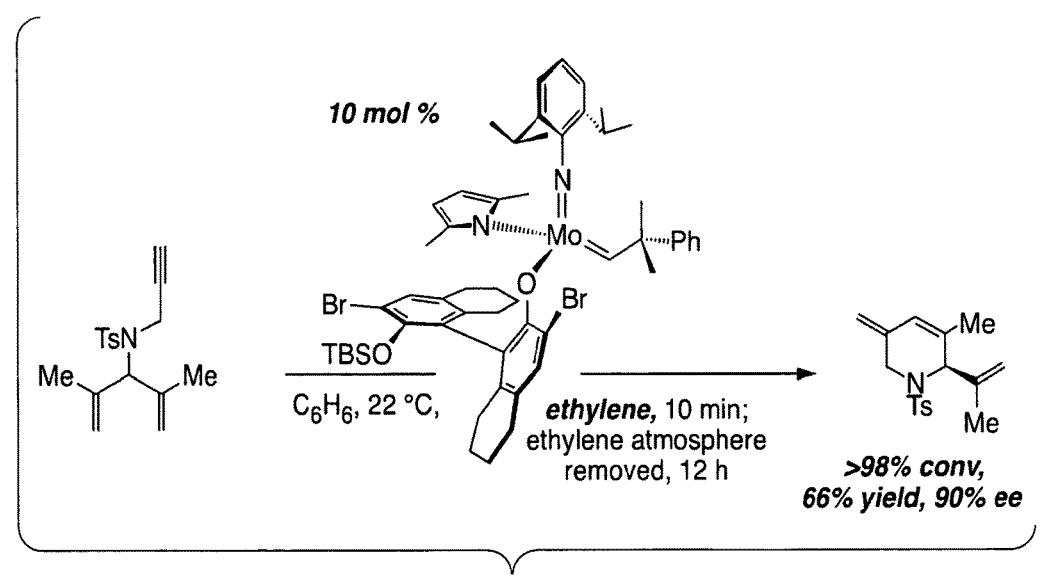
FIG. 37 shows the intramolecular cross-metathesis reaction of N-(2,4-dimethylpenta-1,4-dien-3-yl)-4-methyl-N-(prop-2-ynyl)benzenesulfonamide.
Figure 38:
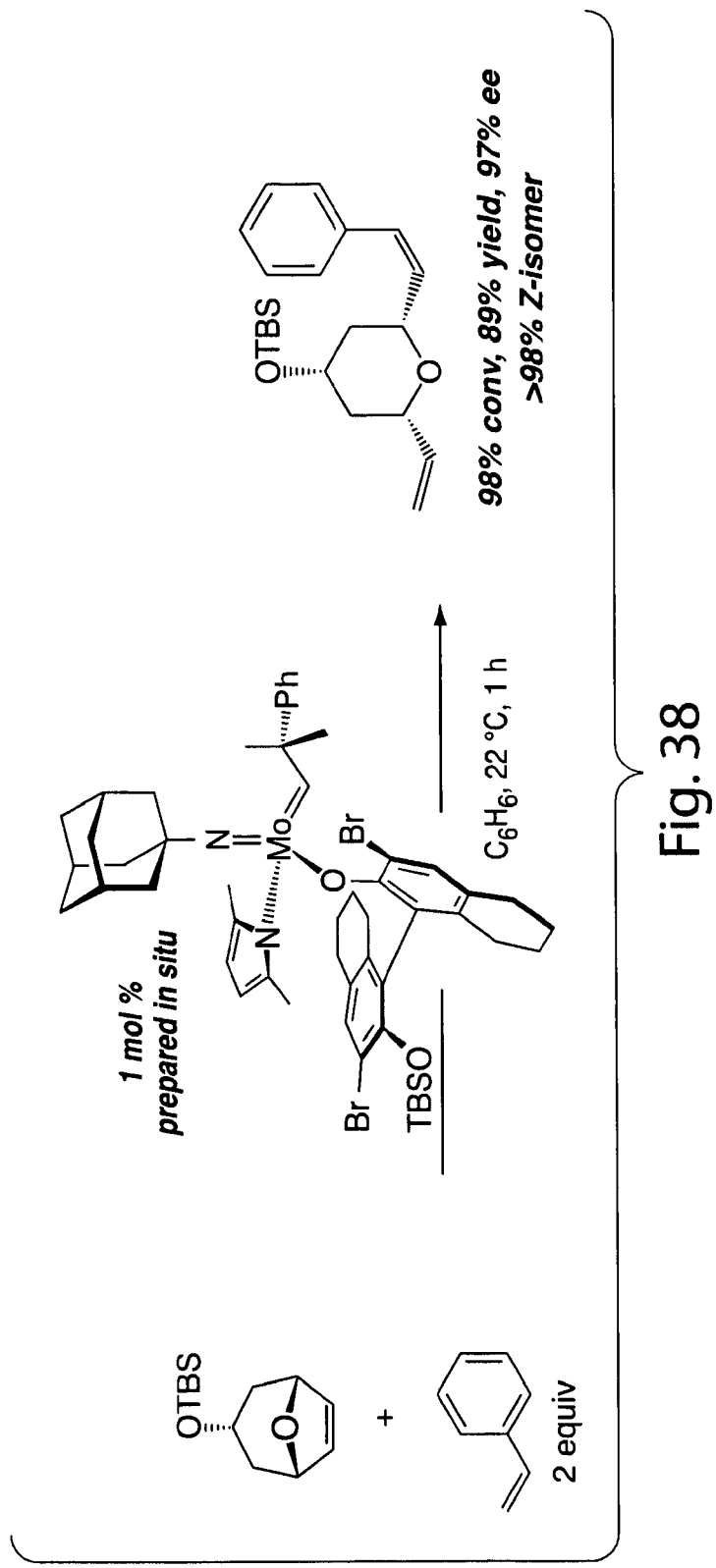
FIG. 38 shows a stereoselective ring-opening cross-metathesis reaction between (8-oxabicyclo[3.2.1]oct-6-en-3-yloxy)(tert-butyl)dimethylsilane and styrene.
Figure 39:
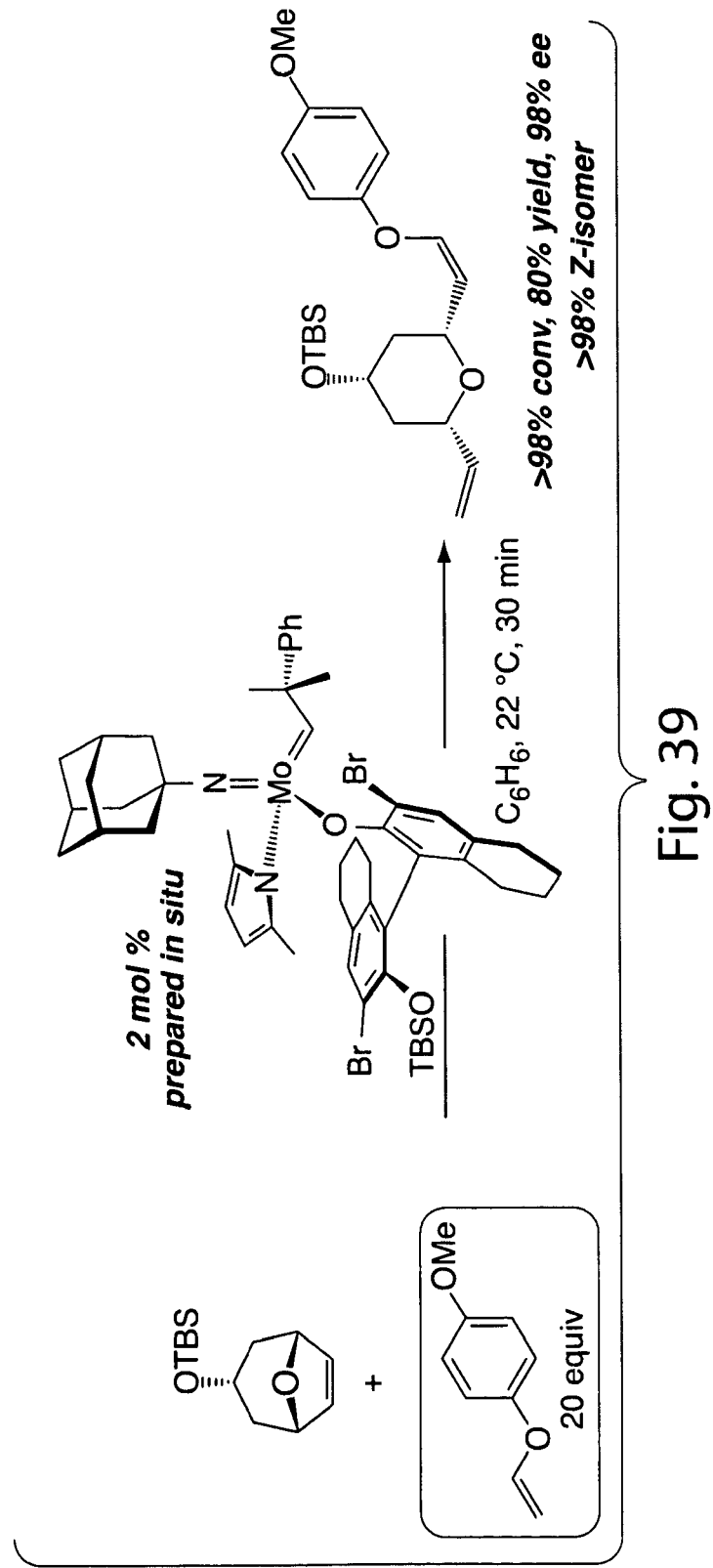
FIG. 39 shows a stereoselective ring-opening cross-metathesis reaction between (8-oxabicyclo[3.2.1]oct-6-en-3-yloxy)(tert-butyl)dimethylsilane and 1-methoxy-4-(vinyloxy)benzene.

Mo complex 28b was employed for ring-opening cross metathesis to produce products with high Z content (e.g., high Z:E ratio). As shown in FIGS. 36 and 37, 28b catalyzed the ring-closing enyne metathesis to produce the products in good yield and high Z content (e.g., >98%).

Example 14

Mo complex 28b was employed for enantioselective ring-closing enyne metathesis reaction. As shown in FIGS. 36 and 37, 28b catalyzed the ring-closing enyne metathesis to produce the product in good yield and good enantioselectivity (e.g., 60%, 90%). The enyne metathesis reaction was generally carried out in the presence of ethylene (e.g., see FIG. 36), which improved the yield of the product. The product produced was >98% Z-isomer.

Example 15

Figure 40:
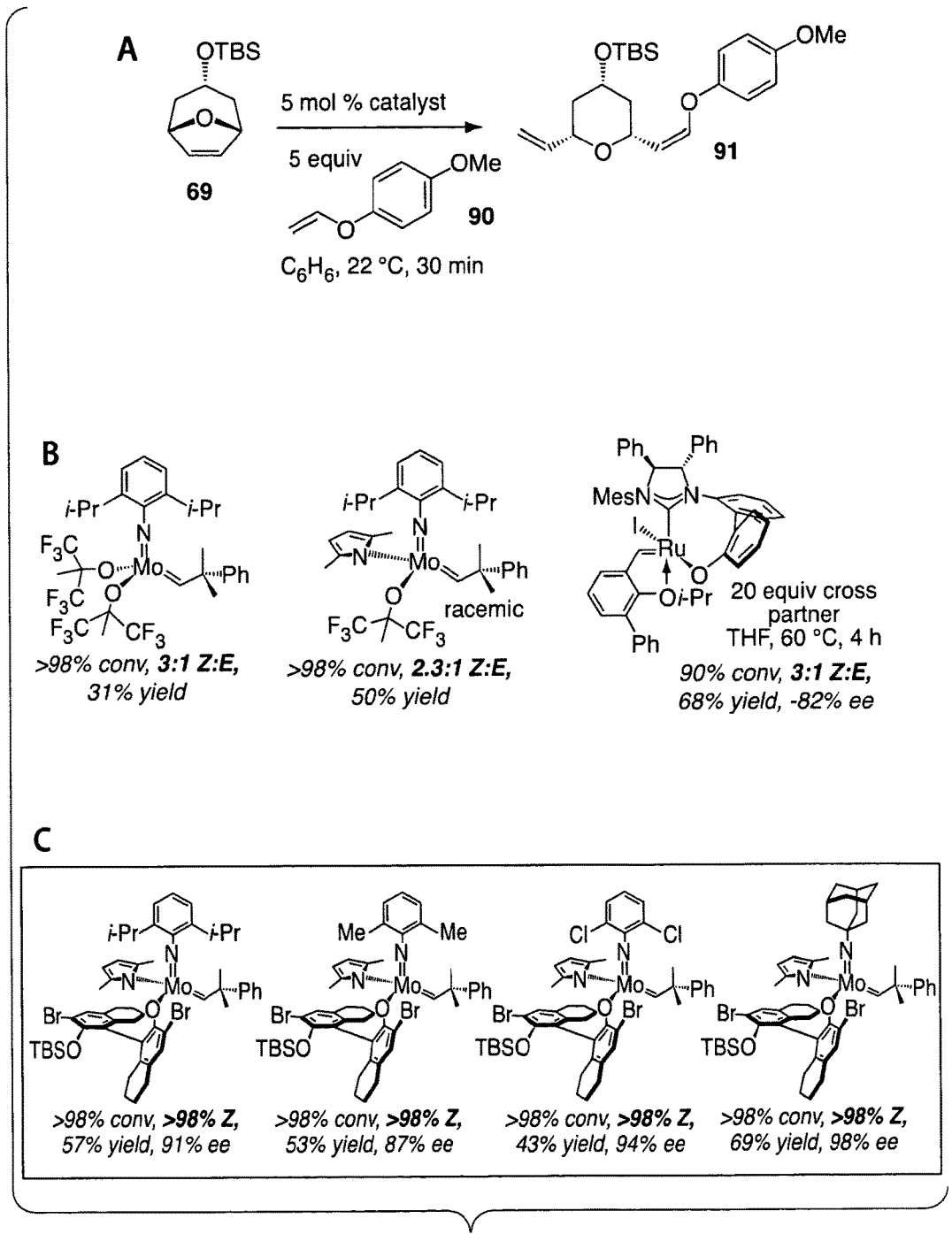
FIG. 40 shows (A) an example of a ring-opening cross-metathesis between a cyclic olefin and a vinyl ether, (B) various metal catalysts and their performance in ring-opening cross-metathesis, and (C) various metal catalysts and their performance in ring-opening cross-metathesis when formed in situ.
Figure 41:
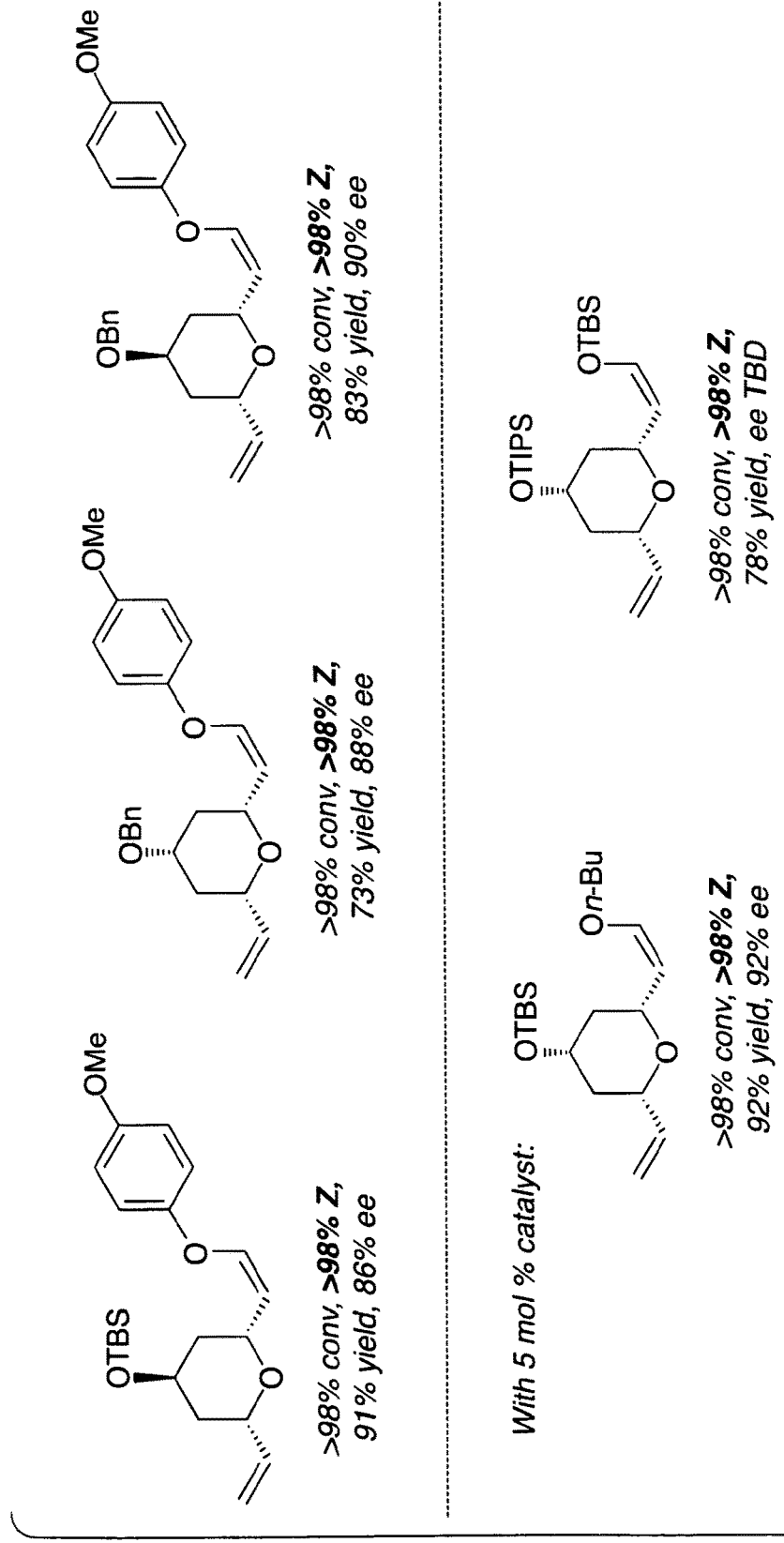
FIG. 41 shows various products formed by ring-opening cross-metathesis reactions between a cyclic olefin and vinyl ether using catalysts described herein.

The ring-opening cross metathesis between a cyclic olefin 69 and a vinyl ether 90, to form product 91, as shown in FIG. 40A, was investigated. FIG. 40B shows the results of the metathesis reaction when employing previously reported catalysts. FIG. 40C shows the results of the metathesis reaction when employing catalysts of the present invention, according to some embodiments. The catalysts of the present invention were able to form 91 with >98% Z selectivity. FIG. 41 shows additional examples of products prepared when using 28b.

Example 16

The following example describes various factors that may be considered in selecting a catalyst for use in a particular invention.

Figure 18A:
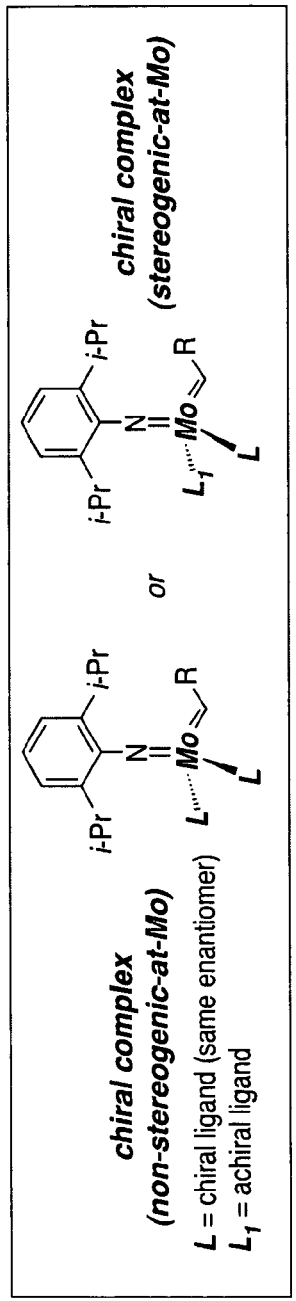
FIG. 18A shows non-limiting examples of chiral Mo complexes.
Figure 18B:
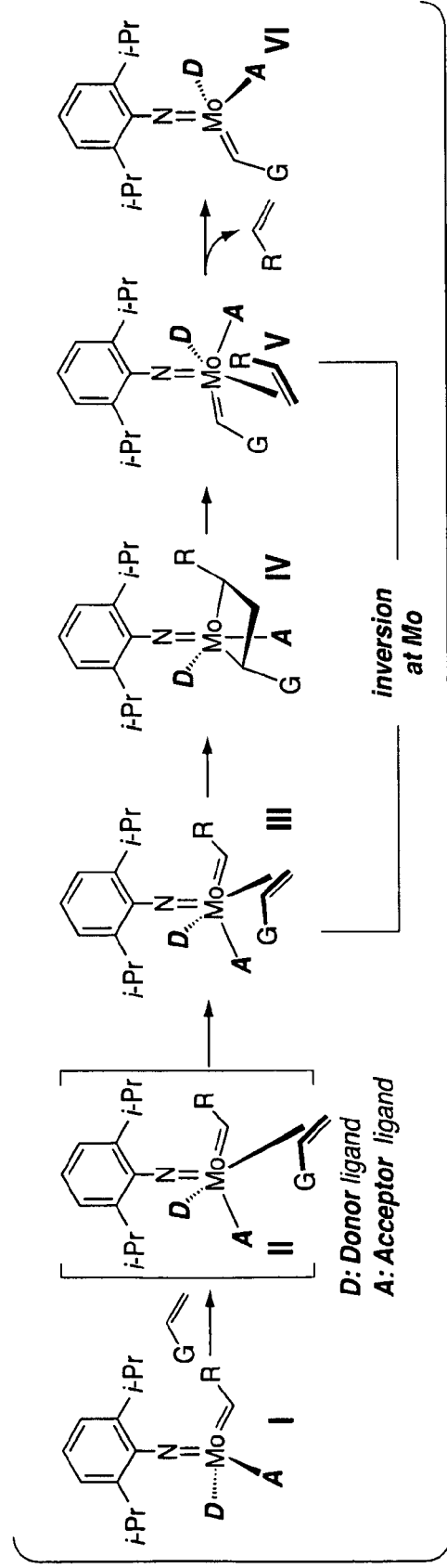
FIG. 18B shows a proposed mechanism for olefin insertion into a Mo complex during enantioselective olefin metathesis.

Without wishing to be bound by theory, in some cases, high oxidation state complexes containing two electronically distinct ligands may be effective promoters of olefin metathesis. As shown in FIG. 18B, an acceptor ligand (e.g., "A" in I) may provide sufficient metal Lewis acidity, which may facilitate binding of a Lewis basic olefin. Efficient olefin coordination may be enhanced by the presence of a sterically accessible ligation site, made available through, for example, alteration of the structure of an initial tetrahedral complex I (FIG. 18B). It has been proposed that donor group "D" can cause I to distort dissymmetrically and that ligand D may interact with the most available metal orbital, such that a trigonal prismatic complex bearing an open coordination site is rendered energetically more accessible. The donor ligand thus can occupy an apical site in II, where the alkylidene, acceptor and imido ligands constitute the basal plane of the trigonal prism, associated opposite only to a weakly bound olefin (trans effect). The resulting complex III can lead to trigonal bipyramidal IV, which may undergo a facile cyclo-reversion, wherein the metallacyclobutane carbons, constituting the olefin being released, are positioned trans to D, affording V. The aforementioned electronic effects can, in some cases, facilitate formation of complex V. Such a scenario may suggest acceleration at two stages of the catalytic cycle, including substrate-catalyst association and metallacyclobutane decomposition.

In some cases, such observations may provide guidance in selecting the imido, alkoxide, and/or alkylidene ligands. For example, for metathesis reaction which are desired to produce products with a high Z:E ratio, the flexibility of the Mo monoaryloxides might be utilized. A sterically demanding and freely rotating aryloxide ligand (e.g., rotation around the Mo—O bond) selected in combination with a sufficiently smaller imido substituent (vs. aryloxide) may favor reaction through the syn alkylidene isomer (e.g., I in FIG. 19) and an all-Z metallacyclobutane (e.g., II, FIG. 19), producing Z-alkene products. In contrast, a rigidly bound chiral bidentate ligand can, in some embodiments, present a substantially less significant steric barrier, resulting in anti alkylidenes and trans-substituted metallacyclobutanes becoming energetically viable intermediates, thus resulting in low Z:E ratio.

As another example, a larger arylimido unit (e.g., 2,6-isopropylphenyl imido), together with the sizeable aryloxide unit, might constitute a Mo complex that is too sterically demanding for formation of the requisite syn or anti alkylidene and subsequent cross-metathesis for the formation of products with a high Z:E ratio. Therefore, replacing the imido unit with a smaller imido ligand (e.g., adamantyl imido) may enhance the activity of the catalyst as well as promoting the formation of products with Z double bonds.

Figure 20A:
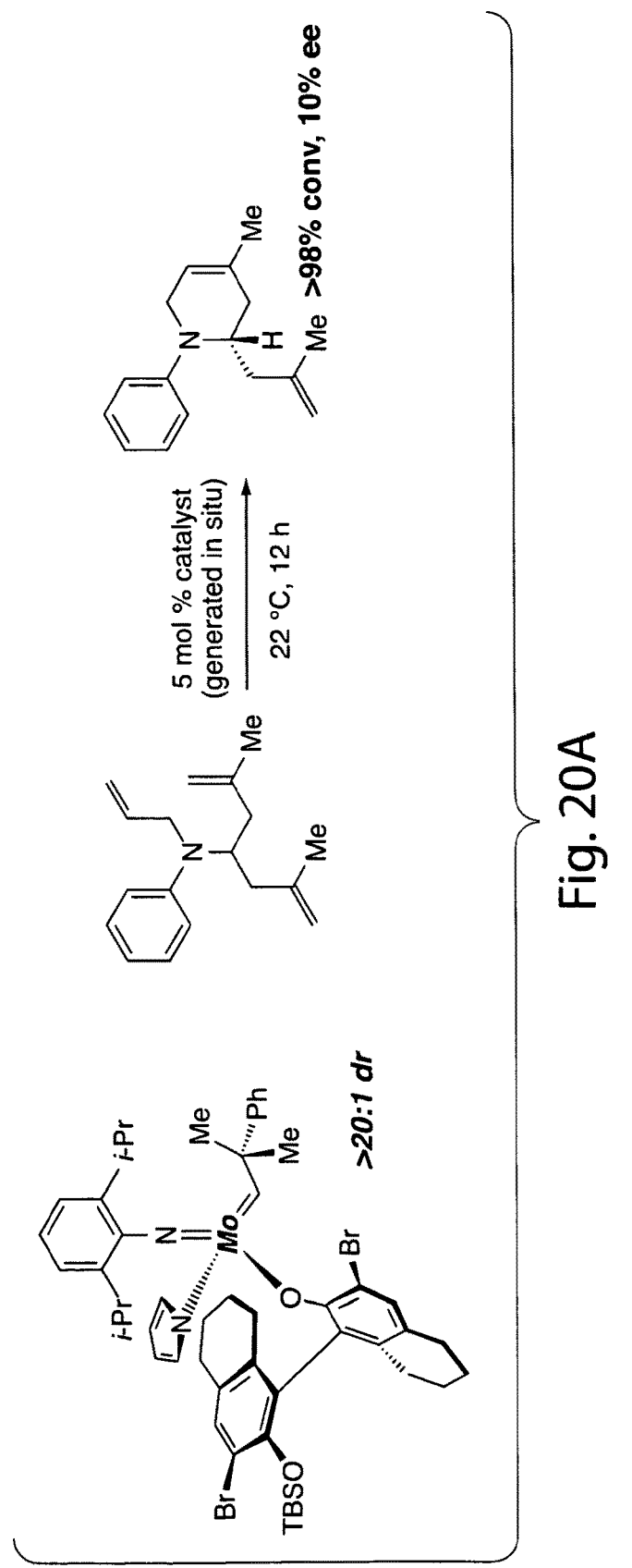
FIGS. 20A and 20B show examples of olefin metathesis reactions using Mo-complexes.
Figure 20B:
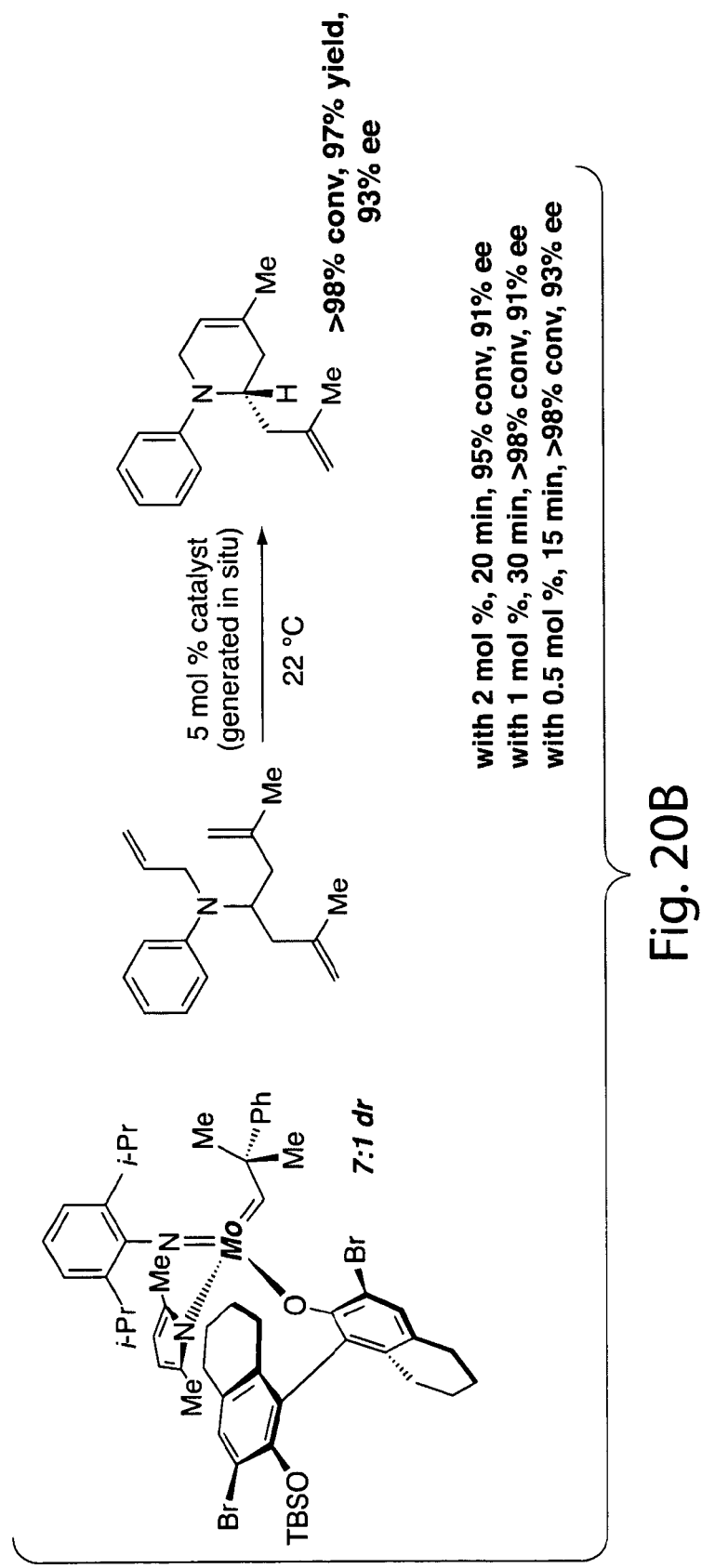

As another non-limiting example, FIGS. 20A and 20B show the results of a metathesis reaction using two Mo complexes of the present invention. A change in the size of the supporting ligand (e.g., in this case, methyl groups on the pyrrolide group) effected the enantiomeric excess of the product.

Figure 17:
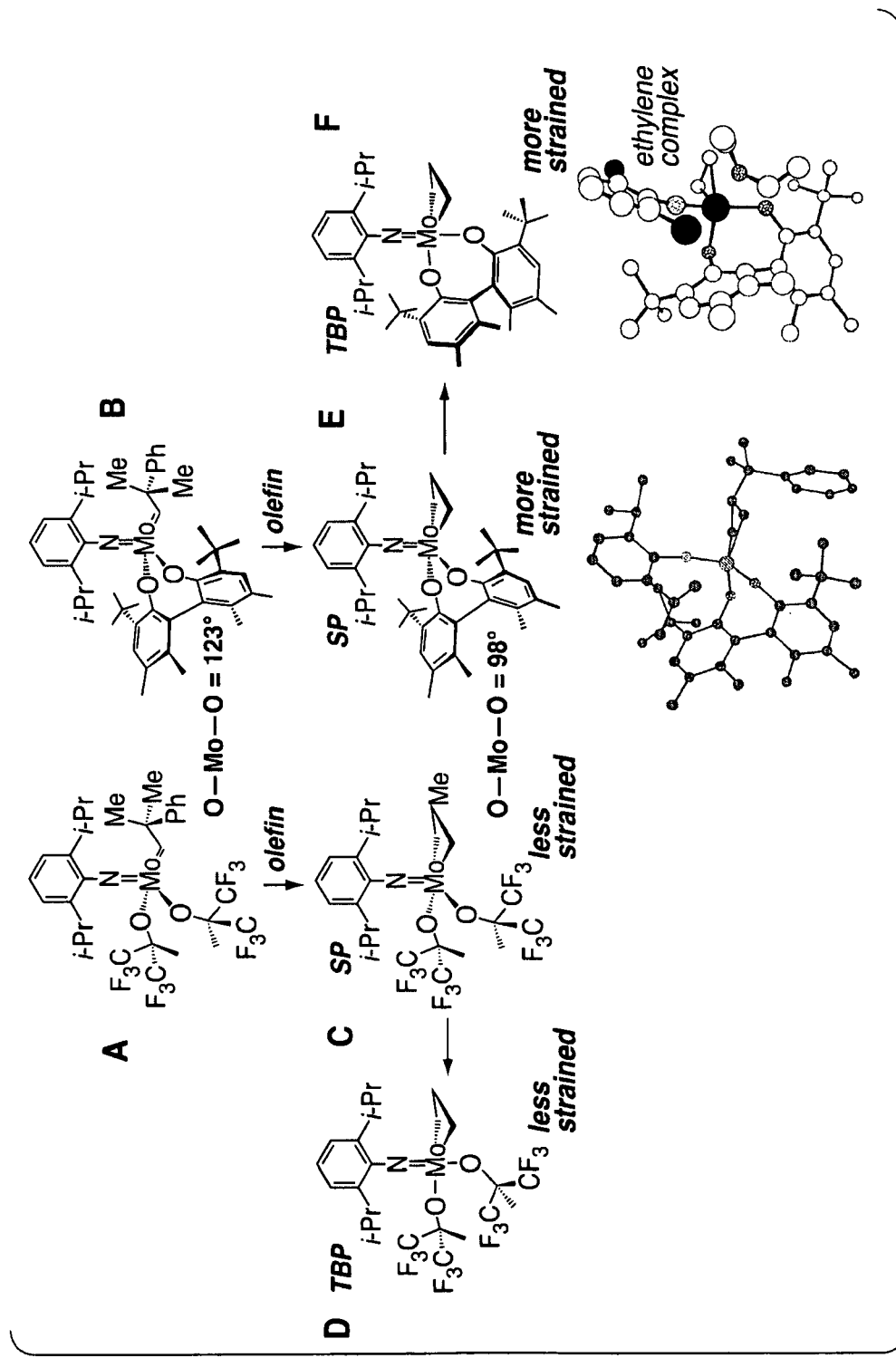
FIG. 17 shows examples of Mo complexes comprising monodentate alkoxides (A) or bidentate alkoxides (B), and the geometry of the complexes (C), (D), (E), (F) following reaction with an olefin.

In some cases, catalysts comprising a stereogenic metal center may exhibit improved catalytic activity and/or stereoselectivity, relative to catalysts comprising non-stereogenic metal centers. Without wishing to be bound by theory, this may be attributed to the energetically accessibly metallacyclobutane intermediate formed during, for example, a metathesis reaction. As shown in FIG. 17, metal catalyst A may adopt a conformation (e.g., C or D, FIG. 17) having relatively lower strain than catalyst B (e.g., E for F, FIG. 17), since catalyst A comprises monodentate ligands while catalyst B comprises a bidentate ligand. Also, the presence of a stereogenic metal center may provide electronic dissymmetry at the metal center, which may lead to improved catalyst activity, as shown in FIG. 17.

Example 17

Table 13-18 provide crystal data and structure information for Mo complex 28b (07190) which is shown in FIG. 22.

TABLE 13

Crystal data and structure refinement for 07190.

| | |
|---|---|
| Identification code | 07190 |
| Empirical formula | $MoC_{59}H_{82}N_2O_2SiBr_2$ |
| Formula weight | 1135.12 |
| Temperature | 100(2) K |
| Wavelength | 0.71073 Å |
| Crystal system | Monoclinic |
| Space group | P2(1) |
| Unit cell dimensions | a = 14.8369(12) Å   $\alpha$ = 90° |
| | b = 14.6098(12) Å   $\beta$ = 103.2760(10)° |
| | c = 27.373(2) Å   $\gamma$ = 90° |
| Volume | 5774.8(8) Å$^3$ |
| Z | 4 |
| Density (calculated) | 1.306 Mg/m$^3$ |
| Absorption coefficient | 1.672 mm$^{-1}$ |
| F(000) | 2368 |
| Crystal size | 0.80 × 0.60 × 0.30 mm$^3$ |
| Theta range for data collection | 0.76 to 29.57° |
| Index ranges | −20 <= h <= 20, −20 <= k <= 20, −38 <= l <= 38 |
| Reflections collected | 128277 |
| Independent reflections | 32378 [R(int) = 0.0388] |
| Completeness to theta = 29.57° | 100.0% |
| Absorption correction | Semi-empirical from equivalents |
| Max. and min. transmission | 0.6338 and 0.3480 |
| Refinement method | Full-matrix least-squares on F$^2$ |
| Data/restraints/parameters | 32378/161/1232 |
| Goodness-of-fit on F$^2$ | 1.023 |
| Final R indices [I > 2sigma(I)] | R1 = 0.0318, wR2 = 0.0722 |
| R indices (all data) | R1 = 0.0418, wR2 = 0.0764 |
| Absolute structure parameter | 0.002(3) |
| Largest diff. peak and hole | 1.288 and −0.489 e · Å$^{-3}$ |

TABLE 14

Atomic coordinates (×10$^4$) and equivalent isotropic displacement parameters (Å$^2$ × 10$^3$) for 07190. U(eq) is defined as one third of the trace of the orthogonalized U$^{ij}$ tensor.

| | x | y | z | U(eq) |
|---|---|---|---|---|
| Mo(1A) | 6369(1) | −289(1) | 6539(1) | 14(1) |
| C(1A) | 6747(2) | −1446(2) | 6357(1) | 19(1) |
| C(2A) | 7203(2) | −2350(2) | 6544(1) | 23(1) |
| C(3A) | 7369(2) | −2405(2) | 7122(1) | 27(1) |
| C(4A) | 6532(2) | −3136(2) | 6325(1) | 34(1) |
| C(5A) | 8104(2) | −2418(2) | 6360(1) | 29(1) |
| C(6A) | 8960(2) | −2205(2) | 6677(1) | 35(1) |
| C(7A) | 9760(2) | −2217(2) | 6501(2) | 49(1) |
| C(8A) | 9727(3) | −2435(3) | 6009(2) | 63(1) |
| C(9A) | 8874(3) | −2646(3) | 5690(2) | 62(1) |
| C(10A) | 8080(3) | −2635(2) | 5866(1) | 44(1) |
| N(1A) | 6855(1) | −255(1) | 7177(1) | 16(1) |
| C(11A) | 7270(2) | −193(2) | 7689(1) | 17(1) |
| C(12A) | 8247(2) | −154(2) | 7839(1) | 19(1) |
| C(13A) | 8648(2) | −180(2) | 8350(1) | 23(1) |
| C(14A) | 8102(2) | −195(2) | 8699(1) | 23(1) |
| C(15A) | 7147(2) | −167(2) | 8546(1) | 23(1) |
| C(16A) | 6704(2) | −181(2) | 8036(1) | 18(1) |
| C(17A) | 8819(2) | −35(2) | 7451(1) | 23(1) |
| C(18A) | 9821(2) | −372(2) | 7623(1) | 37(1) |
| C(19A) | 8798(2) | 977(2) | 7295(1) | 30(1) |
| C(20A) | 5656(2) | −150(2) | 7868(1) | 22(1) |
| C(21A) | 5177(2) | −800(2) | 8163(1) | 40(1) |
| C(22A) | 5310(2) | 834(2) | 7904(1) | 34(1) |
| N(2A) | 7058(1) | 618(1) | 6202(1) | 19(1) |
| C(23A) | 6868(2) | 1547(2) | 6273(1) | 22(1) |
| C(24A) | 7461(2) | 2075(2) | 6077(1) | 29(1) |
| C(25A) | 8045(2) | 1470(2) | 5886(1) | 26(1) |
| C(26A) | 7796(2) | 598(2) | 5958(1) | 21(1) |
| C(27A) | 6115(2) | 1826(2) | 6526(1) | 32(1) |
| C(28A) | 8179(2) | −274(2) | 5812(1) | 29(1) |
| O(1A) | 5030(1) | −208(1) | 6344(1) | 18(1) |
| C(29A) | 4284(2) | −682(2) | 6094(1) | 15(1) |

TABLE 14-continued

Atomic coordinates (×10⁴) and equivalent isotropic displacement parameters ($Å^2 × 10^3$) for 07190. U(eq) is defined as one third of the trace of the orthogonalized $U^{ij}$ tensor.

| | x | y | z | U(eq) |
|---|---|---|---|---|
| C(30A) | 4034(2) | −1520(2) | 6274(1) | 16(1) |
| C(31A) | 3242(2) | −1980(2) | 6022(1) | 19(1) |
| C(32A) | 2675(2) | −1616(2) | 5587(1) | 17(1) |
| C(33A) | 1835(2) | −2147(2) | 5326(1) | 23(1) |
| C(34A) | 1094(2) | −1538(2) | 5007(1) | 25(1) |
| C(35A) | 1537(2) | −962(2) | 4663(1) | 24(1) |
| C(36A) | 2264(2) | −312(2) | 4961(1) | 20(1) |
| C(37A) | 2898(2) | −759(2) | 5411(1) | 16(1) |
| C(38A) | 3695(2) | −291(2) | 5670(1) | 16(1) |
| C(39A) | 3903(2) | 657(2) | 5512(1) | 15(1) |
| C(40A) | 3377(2) | 1384(2) | 5634(1) | 17(1) |
| C(41A) | 3539(2) | 2261(2) | 5472(1) | 23(1) |
| C(42A) | 4232(2) | 2420(2) | 5222(1) | 24(1) |
| C(43A) | 4779(2) | 1711(2) | 5113(1) | 22(1) |
| C(44A) | 5522(2) | 1925(2) | 4830(1) | 26(1) |
| C(45A) | 6120(3) | 1111(3) | 4764(2) | 25(1) |
| C(46A) | 5507(3) | 269(3) | 4630(2) | 23(1) |
| C(45B) | 5720(8) | 1070(6) | 4524(4) | 27(2) |
| C(46B) | 5922(7) | 262(6) | 4888(4) | 26(2) |
| C(47A) | 5094(2) | 11(2) | 5078(1) | 20(1) |
| C(48A) | 4590(2) | 815(2) | 5245(1) | 17(1) |
| O(2A) | 2668(1) | 1222(1) | 5867(1) | 18(1) |
| Si(1A) | 2627(1) | 1296(1) | 6473(1) | 17(1) |
| C(49A) | 3075(2) | 225(2) | 6817(1) | 26(1) |
| C(50A) | 3356(2) | 2271(2) | 6778(1) | 29(1) |
| C(51A) | 1358(2) | 1429(2) | 6457(1) | 21(1) |
| C(52A) | 1244(2) | 1643(2) | 6991(1) | 30(1) |
| C(53A) | 920(2) | 2214(2) | 6109(1) | 33(1) |
| C(54A) | 845(2) | 529(2) | 6278(1) | 34(1) |
| Br(1A) | 4699(1) | −1999(1) | 6893(1) | 24(1) |
| Br(2A) | 2755(1) | 3246(1) | 5559(1) | 33(1) |
| Mo(1) | 1471(1) | −195(1) | 1531(1) | 14(1) |
| C(1) | 1739(2) | −1229(2) | 1180(1) | 17(1) |
| C(2) | 2101(2) | −2200(2) | 1209(1) | 19(1) |
| C(3) | 1281(2) | −2837(2) | 978(1) | 25(1) |
| C(4) | 2478(2) | −2491(2) | 1755(1) | 23(1) |
| C(5) | 2834(2) | −2238(2) | 892(1) | 21(1) |
| C(6) | 3772(2) | −2267(2) | 1102(1) | 26(1) |
| C(7) | 4417(2) | −2251(2) | 804(1) | 32(1) |
| C(8) | 4134(2) | −2221(2) | 291(1) | 33(1) |
| C(9) | 3196(2) | −2192(2) | 72(1) | 30(1) |
| C(10) | 2558(2) | −2200(2) | 368(1) | 26(1) |
| N(1) | 1995(1) | −443(1) | 2145(1) | 17(1) |
| C(11) | 2463(2) | −510(2) | 2648(1) | 18(1) |
| C(12) | 3441(2) | −524(2) | 2772(1) | 22(1) |
| C(13) | 3885(2) | −568(2) | 3281(1) | 25(1) |
| C(14) | 3378(2) | −584(2) | 3648(1) | 28(1) |
| C(15) | 2421(2) | −555(2) | 3521(1) | 26(1) |
| C(16) | 1936(2) | −530(2) | 3020(1) | 20(1) |
| C(17) | 3994(2) | −441(2) | 2375(1) | 24(1) |
| C(18) | 4309(2) | 554(2) | 2343(1) | 33(1) |
| C(19) | 4807(2) | −1109(2) | 2451(1) | 39(1) |
| C(20) | 888(2) | −504(2) | 2882(1) | 24(1) |
| C(21) | 534(2) | 428(2) | 3015(1) | 33(1) |
| C(22) | 465(2) | −1279(2) | 3132(1) | 35(1) |
| N(2) | 2224(1) | 829(1) | 1316(1) | 17(1) |
| C(23) | 2034(2) | 1711(2) | 1474(1) | 20(1) |
| C(24) | 2638(2) | 2317(2) | 1348(1) | 30(1) |
| C(25) | 3239(2) | 1813(2) | 1113(1) | 27(1) |
| C(26) | 2987(2) | 916(2) | 1095(1) | 22(1) |
| C(27) | 1235(2) | 1873(2) | 1714(1) | 23(1) |
| C(28) | 3434(2) | 115(2) | 909(1) | 26(1) |
| O(1) | 134(1) | −82(1) | 1393(1) | 18(1) |
| C(29) | −653(2) | −442(2) | 1109(1) | 15(1) |
| C(30) | −978(2) | −1305(2) | 1204(1) | 17(1) |
| C(31) | −1796(2) | −1647(2) | 916(1) | 19(1) |
| C(32) | −2336(2) | −1132(2) | 525(1) | 18(1) |
| C(33) | −3231(2) | −1536(2) | 220(1) | 23(1) |
| C(34) | −3595(2) | −1030(2) | −272(1) | 26(1) |
| C(35) | −3598(2) | −2(2) | −176(1) | 24(1) |
| C(36) | −2612(2) | 350(2) | 27(1) | 21(1) |
| C(37) | −2042(2) | −247(2) | 433(1) | 17(1) |
| C(38) | −1197(2) | 90(2) | 724(1) | 16(1) |
| C(39) | −851(2) | 1031(2) | 645(1) | 15(1) |
| C(40) | −1193(2) | 1780(2) | 867(1) | 16(1) |
| C(41) | −826(2) | 2643(2) | 810(1) | 17(1) |
| C(42) | −133(2) | 2763(2) | 555(1) | 19(1) |
| C(43) | 205(2) | 2026(2) | 331(1) | 18(1) |
| C(44) | 985(2) | 2187(2) | 65(1) | 24(1) |
| C(45) | 1114(2) | 1399(2) | −280(1) | 27(1) |
| C(46) | 1095(2) | 486(2) | −18(1) | 24(1) |
| C(47) | 150(2) | 338(2) | 106(1) | 20(1) |
| C(48) | −161(2) | 1149(2) | 371(1) | 16(1) |
| O(2) | −1916(1) | 1673(1) | 1093(1) | 18(1) |
| Si(1) | −2071(1) | 1512(1) | 1670(1) | 20(1) |
| C(49) | −1850(2) | 303(2) | 1878(1) | 32(1) |
| C(50) | −1283(2) | 2248(2) | 2131(1) | 35(1) |
| C(51) | −3325(2) | 1812(2) | 1602(1) | 30(1) |
| C(52) | −3929(2) | 1090(2) | 1267(2) | 63(1) |
| C(53) | −3564(2) | 1816(2) | 2113(1) | 45(1) |
| C(54) | −3544(2) | 2756(2) | 1363(1) | 45(1) |
| Br(1) | −341(1) | −1986(1) | 1771(1) | 22(1) |
| Br(2) | −1292(1) | 3692(1) | 1084(1) | 23(1) |
| C(1S) | −3560(3) | −4903(3) | 581(2) | 63(1) |
| C(2S) | −3029(2) | −4548(2) | 1083(1) | 41(1) |
| C(3S) | −3412(2) | −3649(2) | 1229(1) | 30(1) |
| C(4S) | −2889(2) | −3259(2) | 1726(1) | 36(1) |
| C(5S) | −3227(2) | −2315(2) | 1840(1) | 42(1) |
| C(6S) | 419(2) | 5612(2) | 5224(1) | 39(1) |
| C(7S) | 777(3) | 5245(3) | 5762(2) | 66(1) |
| C(8S) | 1753(3) | 5416(3) | 5983(1) | 53(1) |
| C(9S) | 2100(3) | 5045(3) | 6513(1) | 57(1) |
| C(10S) | 3133(3) | 5204(3) | 6698(2) | 77(1) |

TABLE 15

Bond lengths [Å] and angles [°] for 07190

| | |
|---|---|
| Mo(1A)—N(1A) | 1.7317(17) |
| Mo(1A)—C(1A) | 1.884(2) |
| Mo(1A)—O(1A) | 1.9397(15) |
| Mo(1A)—N(2A) | 2.020(2) |
| C(1A)—C(2A) | 1.518(3) |
| C(2A)—C(5A) | 1.537(4) |
| C(2A)—C(3A) | 1.547(3) |
| C(2A)—C(4A) | 1.548(4) |
| C(5A)—C(10A) | 1.380(4) |
| C(5A)—C(6A) | 1.398(4) |
| C(6A)—C(7A) | 1.380(4) |
| C(7A)—C(8A) | 1.375(5) |
| C(8A)—C(9A) | 1.398(6) |
| C(9A)—C(10A) | 1.372(5) |
| N(1A)—C(11A) | 1.397(3) |
| C(11A)—C(16A) | 1.406(3) |
| C(11A)—C(12A) | 1.414(3) |
| C(12A)—C(13A) | 1.390(3) |
| C(12A)—C(17A) | 1.514(3) |
| C(13A)—C(14A) | 1.387(3) |
| C(14A)—C(15A) | 1.383(4) |
| C(15A)—C(16A) | 1.401(3) |
| C(16A)—C(20A) | 1.518(3) |
| C(17A)—C(18A) | 1.534(3) |
| C(17A)—C(19A) | 1.537(4) |
| C(20A)—C(21A) | 1.523(4) |
| C(20A)—C(22A) | 1.537(4) |
| N(2A)—C(26A) | 1.409(3) |
| N(2A)—C(23A) | 1.409(3) |
| C(23A)—C(24A) | 1.371(4) |
| C(23A)—C(27A) | 1.498(4) |
| C(24A)—C(25A) | 1.419(4) |
| C(25A)—C(26A) | 1.354(4) |
| C(26A)—C(28A) | 1.486(4) |
| O(1A)—C(29A) | 1.350(3) |
| C(29A)—C(30A) | 1.402(3) |
| C(29A)—C(38A) | 1.405(3) |

TABLE 15-continued

Bond lengths [Å] and angles [°] for 07190

| | |
|---|---|
| C(30A)—C(31A) | 1.391(3) |
| C(30A)—Br(1A) | 1.887(2) |
| C(31A)—C(32A) | 1.396(3) |
| C(32A)—C(37A) | 1.408(3) |
| C(32A)—C(33A) | 1.504(3) |
| C(33A)—C(34A) | 1.523(4) |
| C(34A)—C(35A) | 1.520(4) |
| C(35A)—C(36A) | 1.525(3) |
| C(36A)—C(37A) | 1.515(3) |
| C(37A)—C(38A) | 1.408(3) |
| C(38A)—C(39A) | 1.503(3) |
| C(39A)—C(48A) | 1.403(3) |
| C(39A)—C(40A) | 1.403(3) |
| C(40A)—O(2A) | 1.370(3) |
| C(40A)—C(41A) | 1.395(3) |
| C(41A)—C(42A) | 1.381(4) |
| C(41A)—Br(2A) | 1.900(2) |
| C(42A)—C(43A) | 1.391(4) |
| C(43A)—C(48A) | 1.403(3) |
| C(43A)—C(44A) | 1.519(3) |
| C(44A)—C(45A) | 1.518(5) |
| C(44A)—C(45B) | 1.568(9) |
| C(45A)—C(46A) | 1.523(6) |
| C(46A)—C(47A) | 1.537(4) |
| C(45B)—C(46B) | 1.528(11) |
| C(46B)—C(47A) | 1.485(8) |
| C(47A)—C(48A) | 1.519(3) |
| O(2A)—Si(1A) | 1.6749(17) |
| Si(1A)—C(50A) | 1.866(3) |
| Si(1A)—C(49A) | 1.868(3) |
| Si(1A)—C(51A) | 1.885(2) |
| C(51A)—C(53A) | 1.536(4) |
| C(51A)—C(52A) | 1.539(3) |
| C(51A)—C(54A) | 1.542(4) |
| Mo(1)—N(1) | 1.7220(18) |
| Mo(1)—C(1) | 1.881(2) |
| Mo(1)—O(1) | 1.9390(16) |
| Mo(1)—N(2) | 2.034(2) |
| C(1)—C(2) | 1.513(3) |
| C(2)—C(4) | 1.531(3) |
| C(2)—C(5) | 1.540(3) |
| C(2)—C(3) | 1.546(3) |
| C(5)—C(6) | 1.379(4) |
| C(5)—C(10) | 1.399(3) |
| C(6)—C(7) | 1.394(4) |
| C(7)—C(8) | 1.372(4) |
| C(8)—C(9) | 1.384(4) |
| C(9)—C(10) | 1.383(4) |
| N(1)—C(11) | 1.394(3) |
| C(11)—C(12) | 1.414(3) |
| C(11)—C(16) | 1.420(3) |
| C(12)—C(13) | 1.398(3) |
| C(12)—C(17) | 1.509(4) |
| C(13)—C(14) | 1.386(4) |
| C(14)—C(15) | 1.383(4) |
| C(15)—C(16) | 1.394(3) |
| C(16)—C(20) | 1.514(4) |
| C(17)—C(19) | 1.528(4) |
| C(17)—C(18) | 1.536(4) |
| C(20)—C(22) | 1.528(4) |
| C(20)—C(21) | 1.533(4) |
| N(2)—C(26) | 1.406(3) |
| N(2)—C(23) | 1.409(3) |
| C(23)—C(24) | 1.360(4) |
| C(23)—C(27) | 1.500(4) |
| C(24)—C(25) | 1.421(4) |
| C(25)—C(26) | 1.360(4) |
| C(26)—C(28) | 1.491(4) |
| O(1)—C(29) | 1.352(3) |
| C(29)—C(30) | 1.396(3) |
| C(29)—C(38) | 1.405(3) |
| C(30)—C(31) | 1.381(3) |
| C(30)—Br(1) | 1.902(3) |
| C(31)—C(32) | 1.399(3) |
| C(32)—C(37) | 1.406(3) |
| C(32)—C(33) | 1.517(3) |
| C(33)—C(34) | 1.523(3) |
| C(34)—C(35) | 1.526(4) |
| C(35)—C(36) | 1.530(3) |
| C(36)—C(37) | 1.510(3) |
| C(37)—C(38) | 1.411(3) |
| C(38)—C(39) | 1.500(3) |
| C(39)—C(40) | 1.402(3) |
| C(39)—C(48) | 1.412(3) |
| C(40)—O(2) | 1.365(3) |
| C(40)—C(41) | 1.397(3) |
| C(41)—C(42) | 1.380(3) |
| C(41)—Br(2) | 1.904(2) |
| C(42)—C(43) | 1.387(3) |
| C(43)—C(48) | 1.406(3) |
| C(43)—C(44) | 1.520(3) |
| C(44)—C(45) | 1.529(4) |
| C(45)—C(46) | 1.518(4) |
| C(46)—C(47) | 1.532(3) |
| C(47)—C(48) | 1.516(3) |
| O(2)—Si(1) | 1.6656(17) |
| Si(1)—C(50) | 1.853(3) |
| Si(1)—C(49) | 1.862(3) |
| Si(1)—C(51) | 1.878(3) |
| C(51)—C(53) | 1.520(4) |
| C(51)—C(54) | 1.530(4) |
| C(51)—C(52) | 1.542(4) |
| C(1S)—C(2S) | 1.511(5) |
| C(2S)—C(3S) | 1.520(4) |
| C(3S)—C(4S) | 1.514(4) |
| C(4S)—C(5S) | 1.524(4) |
| C(6S)—C(7S) | 1.542(5) |
| C(7S)—C(8S) | 1.458(5) |
| C(8S)—C(9S) | 1.523(5) |
| C(9S)—C(10S) | 1.517(5) |
| N(1A)—Mo(1A)—C(1A) | 102.29(10) |
| N(1A)—Mo(1A)—O(1A) | 115.99(8) |
| C(1A)—Mo(1A)—O(1A) | 109.29(9) |
| N(1A)—Mo(1A)—N(2A) | 107.73(9) |
| C(1A)—Mo(1A)—N(2A) | 104.80(9) |
| O(1A)—Mo(1A)—N(2A) | 115.38(8) |
| C(2A)—C(1A)—Mo(1A) | 145.86(18) |
| C(1A)—C(2A)—C(5A) | 107.3(2) |
| C(1A)—C(2A)—C(3A) | 110.2(2) |
| C(5A)—C(2A)—C(3A) | 112.7(2) |
| C(1A)—C(2A)—C(4A) | 108.6(2) |
| C(5A)—C(2A)—C(4A) | 110.8(2) |
| C(3A)—C(2A)—C(4A) | 107.2(2) |
| C(10A)—C(5A)—C(6A) | 118.3(3) |
| C(10A)—C(5A)—C(2A) | 120.5(3) |
| C(6A)—C(5A)—C(2A) | 121.1(3) |
| C(7A)—C(6A)—C(5A) | 120.8(3) |
| C(8A)—C(7A)—C(6A) | 120.3(4) |
| C(7A)—C(8A)—C(9A) | 119.1(3) |
| C(10A)—C(9A)—C(8A) | 120.4(4) |
| C(9A)—C(10A)—C(5A) | 121.1(4) |
| C(11A)—N(1A)—Mo(1A) | 177.40(18) |
| N(1A)—C(11A)—C(16A) | 119.0(2) |
| N(1A)—C(11A)—C(12A) | 118.7(2) |
| C(16A)—C(11A)—C(12A) | 122.3(2) |
| C(13A)—C(12A)—C(11A) | 117.7(2) |
| C(13A)—C(12A)—C(17A) | 122.0(2) |
| C(11A)—C(12A)—C(17A) | 120.2(2) |
| C(14A)—C(13A)—C(12A) | 120.8(2) |
| C(15A)—C(14A)—C(13A) | 120.8(2) |
| C(14A)—C(15A)—C(16A) | 121.0(2) |
| C(15A)—C(16A)—C(11A) | 117.3(2) |
| C(15A)—C(16A)—C(20A) | 121.0(2) |
| C(11A)—C(16A)—C(20A) | 121.68(19) |
| C(12A)—C(17A)—C(18A) | 114.1(2) |
| C(12A)—C(17A)—C(19A) | 109.0(2) |
| C(18A)—C(17A)—C(19A) | 110.5(2) |
| C(16A)—C(20A)—C(21A) | 113.0(2) |
| C(16A)—C(20A)—C(22A) | 110.1(2) |
| C(21A)—C(20A)—C(22A) | 110.3(2) |
| C(26A)—N(2A)—C(23A) | 106.8(2) |
| C(26A)—N(2A)—Mo(1A) | 137.10(17) |
| C(23A)—N(2A)—Mo(1A) | 115.47(16) |
| C(24A)—C(23A)—N(2A) | 108.7(2) |
| C(24A)—C(23A)—C(27A) | 129.9(2) |
| N(2A)—C(23A)—C(27A) | 121.4(2) |

TABLE 15-continued

Bond lengths [Å] and angles [°] for 07190

| | |
|---|---|
| C(23A)—C(24A)—C(25A) | 107.2(2) |
| C(26A)—C(25A)—C(24A) | 108.8(2) |
| C(25A)—C(26A)—N(2A) | 108.5(2) |
| C(25A)—C(26A)—C(28A) | 129.4(2) |
| N(2A)—C(26A)—C(28A) | 122.2(2) |
| C(29A)—O(1A)—Mo(1A) | 141.02(15) |
| O(1A)—C(29A)—C(30A) | 121.5(2) |
| O(1A)—C(29A)—C(38A) | 119.5(2) |
| C(30A)—C(29A)—C(38A) | 118.8(2) |
| C(31A)—C(30A)—C(29A) | 120.6(2) |
| C(31A)—C(30A)—Br(1A) | 118.30(17) |
| C(29A)—C(30A)—Br(1A) | 120.85(17) |
| C(30A)—C(31A)—C(32A) | 120.9(2) |
| C(31A)—C(32A)—C(37A) | 119.3(2) |
| C(31A)—C(32A)—C(33A) | 118.7(2) |
| C(37A)—C(32A)—C(33A) | 122.0(2) |
| C(32A)—C(33A)—C(34A) | 112.4(2) |
| C(35A)—C(34A)—C(33A) | 108.7(2) |
| C(34A)—C(35A)—C(36A) | 111.5(2) |
| C(37A)—C(36A)—C(35A) | 113.4(2) |
| C(32A)—C(37A)—C(38A) | 119.6(2) |
| C(32A)—C(37A)—C(36A) | 120.8(2) |
| C(38A)—C(37A)—C(36A) | 119.5(2) |
| C(29A)—C(38A)—C(37A) | 120.7(2) |
| C(29A)—C(38A)—C(39A) | 118.8(2) |
| C(37A)—C(38A)—C(39A) | 120.5(2) |
| C(48A)—C(39A)—C(40A) | 120.6(2) |
| C(48A)—C(39A)—C(38A) | 121.6(2) |
| C(40A)—C(39A)—C(38A) | 117.8(2) |
| O(2A)—C(40A)—C(41A) | 120.8(2) |
| O(2A)—C(40A)—C(39A) | 120.6(2) |
| C(41A)—C(40A)—C(39A) | 118.3(2) |
| C(42A)—C(41A)—C(40A) | 121.0(2) |
| C(42A)—C(41A)—Br(2A) | 118.79(18) |
| C(40A)—C(41A)—Br(2A) | 120.12(19) |
| C(41A)—C(42A)—C(43A) | 121.3(2) |
| C(42A)—C(43A)—C(48A) | 118.6(2) |
| C(42A)—C(43A)—C(44A) | 118.9(2) |
| C(48A)—C(43A)—C(44A) | 122.4(2) |
| C(45A)—C(44A)—C(43A) | 114.2(2) |
| C(45A)—C(44A)—C(45B) | 29.2(4) |
| C(43A)—C(44A)—C(45B) | 110.7(4) |
| C(44A)—C(45A)—C(46A) | 109.2(3) |
| C(45A)—C(46A)—C(47A) | 109.3(3) |
| C(46B)—C(45B)—C(44A) | 107.6(7) |
| C(47A)—C(46B)—C(45B) | 111.3(7) |
| C(46B)—C(47A)—C(48A) | 114.8(4) |
| C(46B)—C(47A)—C(46A) | 31.5(4) |
| C(48A)—C(47A)—C(46A) | 111.4(2) |
| C(39A)—C(48A)—C(43A) | 120.1(2) |
| C(39A)—C(48A)—C(47A) | 119.8(2) |
| C(43A)—C(48A)—C(47A) | 120.1(2) |
| C(40A)—O(2A)—Si(1A) | 130.98(15) |
| O(2A)—Si(1A)—C(50A) | 110.09(11) |
| O(2A)—Si(1A)—C(49A) | 110.85(10) |
| C(50A)—Si(1A)—C(49A) | 108.11(13) |
| O(2A)—Si(1A)—C(51A) | 104.35(10) |
| C(50A)—Si(1A)—C(51A) | 113.85(12) |
| C(49A)—Si(1A)—C(51A) | 109.58(12) |
| C(53A)—C(51A)—C(52A) | 108.3(2) |
| C(53A)—C(51A)—C(54A) | 109.4(2) |
| C(52A)—C(51A)—C(54A) | 108.7(2) |
| C(53A)—C(51A)—Si(1A) | 111.63(18) |
| C(52A)—C(51A)—Si(1A) | 109.06(17) |
| C(54A)—C(51A)—Si(1A) | 109.66(18) |
| N(1)—Mo(1)—C(1) | 103.22(10) |
| N(1)—Mo(1)—O(1) | 114.84(8) |
| C(1)—Mo(1)—O(1) | 107.25(8) |
| N(1)—Mo(1)—N(2) | 106.42(8) |
| C(1)—Mo(1)—N(2) | 104.36(9) |
| O(1)—Mo(1)—N(2) | 119.12(7) |
| C(2)—C(1)—Mo(1) | 147.17(17) |
| C(1)—C(2)—C(4) | 110.98(19) |
| C(1)—C(2)—C(5) | 106.95(19) |
| C(4)—C(2)—C(5) | 113.1(2) |
| C(1)—C(2)—C(3) | 107.84(19) |
| C(4)—C(2)—C(3) | 108.0(2) |
| C(5)—C(2)—C(3) | 109.9(2) |
| C(6)—C(5)—C(10) | 117.3(2) |
| C(6)—C(5)—C(2) | 122.8(2) |
| C(10)—C(5)—C(2) | 119.8(2) |
| C(5)—C(6)—C(7) | 121.2(2) |
| C(8)—C(7)—C(6) | 120.7(3) |
| C(7)—C(8)—C(9) | 119.1(3) |
| C(10)—C(9)—C(8) | 120.1(3) |
| C(9)—C(10)—C(5) | 121.6(3) |
| C(11)—N(1)—Mo(1) | 171.50(17) |
| N(1)—C(11)—C(12) | 119.3(2) |
| N(1)—C(11)—C(16) | 118.6(2) |
| C(12)—C(11)—C(16) | 122.1(2) |
| C(13)—C(12)—C(11) | 117.6(2) |
| C(13)—C(12)—C(17) | 120.7(2) |
| C(11)—C(12)—C(17) | 121.5(2) |
| C(14)—C(13)—C(12) | 120.8(2) |
| C(15)—C(14)—C(13) | 120.9(2) |
| C(14)—C(15)—C(16) | 121.1(3) |
| C(15)—C(16)—C(11) | 117.4(2) |
| C(15)—C(16)—C(20) | 121.0(2) |
| C(11)—C(16)—C(20) | 121.6(2) |
| C(12)—C(17)—C(19) | 113.2(2) |
| C(12)—C(17)—C(18) | 109.8(2) |
| C(19)—C(17)—C(18) | 111.8(2) |
| C(16)—C(20)—C(22) | 111.9(2) |
| C(16)—C(20)—C(21) | 110.6(2) |
| C(22)—C(20)—C(21) | 110.8(2) |
| C(26)—N(2)—C(23) | 106.71(19) |
| C(26)—N(2)—Mo(1) | 137.85(16) |
| C(23)—N(2)—Mo(1) | 114.93(16) |
| C(24)—C(23)—N(2) | 109.1(2) |
| C(24)—C(23)—C(27) | 129.9(2) |
| N(2)—C(23)—C(27) | 120.9(2) |
| C(23)—C(24)—C(25) | 107.2(2) |
| C(26)—C(25)—C(24) | 108.7(2) |
| C(25)—C(26)—N(2) | 108.3(2) |
| C(25)—C(26)—C(28) | 128.9(2) |
| N(2)—C(26)—C(28) | 122.7(2) |
| C(29)—O(1)—Mo(1) | 142.00(15) |
| O(1)—C(29)—C(30) | 122.3(2) |
| O(1)—C(29)—C(38) | 119.2(2) |
| C(30)—C(29)—C(38) | 118.4(2) |
| C(31)—C(30)—C(29) | 121.1(2) |
| C(31)—C(30)—Br(1) | 118.95(18) |
| C(29)—C(30)—Br(1) | 119.76(17) |
| C(30)—C(31)—C(32) | 121.0(2) |
| C(31)—C(32)—C(37) | 119.0(2) |
| C(31)—C(32)—C(33) | 119.1(2) |
| C(37)—C(32)—C(33) | 121.8(2) |
| C(32)—C(33)—C(34) | 112.7(2) |
| C(33)—C(34)—C(35) | 109.8(2) |
| C(34)—C(35)—C(36) | 110.7(2) |
| C(37)—C(36)—C(35) | 113.6(2) |
| C(32)—C(37)—C(38) | 119.5(2) |
| C(32)—C(37)—C(36) | 121.3(2) |
| C(38)—C(37)—C(36) | 119.3(2) |
| C(29)—C(38)—C(37) | 120.9(2) |
| C(29)—C(38)—C(39) | 117.2(2) |
| C(37)—C(38)—C(39) | 121.9(2) |
| C(40)—C(39)—C(48) | 120.9(2) |
| C(40)—C(39)—C(38) | 118.9(2) |
| C(48)—C(39)—C(38) | 120.2(2) |
| O(2)—C(40)—C(41) | 121.5(2) |
| O(2)—C(40)—C(39) | 120.4(2) |
| C(41)—C(40)—C(39) | 117.8(2) |
| C(42)—C(41)—C(40) | 121.8(2) |
| C(42)—C(41)—Br(2) | 118.54(17) |
| C(40)—C(41)—Br(2) | 119.70(18) |
| C(41)—C(42)—C(43) | 120.8(2) |
| C(42)—C(43)—C(48) | 119.2(2) |
| C(42)—C(43)—C(44) | 118.9(2) |
| C(48)—C(43)—C(44) | 121.9(2) |
| C(43)—C(44)—C(45) | 113.4(2) |
| C(46)—C(45)—C(44) | 110.5(2) |
| C(45)—C(46)—C(47) | 110.2(2) |
| C(48)—C(47)—C(46) | 112.9(2) |
| C(43)—C(48)—C(39) | 119.6(2) |
| C(43)—C(48)—C(47) | 120.6(2) |

TABLE 15-continued

Bond lengths [Å] and angles [°] for 07190

| | |
|---|---|
| C(39)—C(48)—C(47) | 119.7(2) |
| C(40)—O(2)—Si(1) | 137.77(15) |
| O(2)—Si(1)—C(50) | 111.17(11) |
| O(2)—Si(1)—C(49) | 111.71(11) |
| C(50)—Si(1)—C(49) | 107.68(14) |
| O(2)—Si(1)—C(51) | 102.82(11) |
| C(50)—Si(1)—C(51) | 112.87(14) |
| C(49)—Si(1)—C(51) | 110.63(13) |
| C(53)—C(51)—C(54) | 108.6(2) |
| C(53)—C(51)—C(52) | 108.9(3) |
| C(54)—C(51)—C(52) | 109.0(3) |
| C(53)—C(51)—Si(1) | 110.2(2) |
| C(54)—C(51)—Si(1) | 111.1(2) |
| C(52)—C(51)—Si(1) | 109.1(2) |
| C(1S)—C(2S)—C(3S) | 112.8(3) |
| C(4S)—C(3S)—C(2S) | 114.5(2) |
| C(3S)—C(4S)—C(5S) | 113.6(2) |
| C(8S)—C(7S)—C(6S) | 115.3(3) |
| C(7S)—C(8S)—C(9S) | 114.8(3) |
| C(10S)—C(9S)—C(8S) | 111.0(3) |

Symmetry transformations used to generate equivalent atoms:

TABLE 16

Anisotropic displacement parameters (Å² × 10³) for 07190.
The anisotropic displacement factor exponent takes the form:
$-2p^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| Mo(1A) | 15(1) | 11(1) | 14(1) | 1(1) | 1(1) | −1(1) |
| C(1A) | 22(1) | 16(1) | 19(1) | 1(1) | 3(1) | −1(1) |
| C(2A) | 28(1) | 15(1) | 24(1) | 1(1) | 1(1) | 3(1) |
| C(3A) | 31(1) | 19(1) | 27(1) | 7(1) | 0(1) | 8(1) |
| C(4A) | 42(2) | 14(1) | 42(2) | −3(1) | 2(1) | 2(1) |
| C(5A) | 34(2) | 20(1) | 32(1) | 3(1) | 5(1) | 15(1) |
| C(6A) | 35(2) | 26(2) | 45(2) | 11(1) | 9(1) | 9(1) |
| C(7A) | 35(2) | 47(2) | 71(2) | 23(2) | 21(2) | 16(2) |
| C(8A) | 55(3) | 66(3) | 80(3) | 25(2) | 40(2) | 31(2) |
| C(9A) | 77(3) | 65(3) | 53(2) | 11(2) | 34(2) | 38(2) |
| C(10A) | 53(2) | 42(2) | 38(2) | 5(1) | 13(2) | 23(2) |
| N(1A) | 18(1) | 15(1) | 15(1) | 1(1) | 2(1) | −2(1) |
| C(11A) | 22(1) | 11(1) | 15(1) | 0(1) | 0(1) | −1(1) |
| C(12A) | 24(1) | 12(1) | 20(1) | 0(1) | 1(1) | 1(1) |
| C(13A) | 24(1) | 18(1) | 22(1) | −1(1) | −4(1) | −1(1) |
| C(14A) | 33(1) | 18(1) | 15(1) | 0(1) | −2(1) | −1(1) |
| C(15A) | 35(1) | 16(1) | 18(1) | −1(1) | 7(1) | −6(1) |
| C(16A) | 22(1) | 12(1) | 20(1) | 0(1) | 4(1) | −2(1) |
| C(17A) | 20(1) | 27(1) | 22(1) | −2(1) | 3(1) | −2(1) |
| C(18A) | 23(1) | 53(2) | 35(2) | 0(1) | 6(1) | 3(1) |
| C(19A) | 29(1) | 32(2) | 29(1) | 1(1) | 6(1) | −8(1) |
| C(20A) | 23(1) | 26(1) | 18(1) | −2(1) | 7(1) | −6(1) |
| C(21A) | 38(2) | 50(2) | 36(2) | 6(1) | 14(1) | −17(2) |
| C(22A) | 26(2) | 27(1) | 47(2) | −7(1) | 4(1) | 2(1) |
| N(2A) | 20(1) | 14(1) | 20(1) | 1(1) | 3(1) | −1(1) |
| C(23A) | 28(1) | 13(1) | 25(1) | 0(1) | 6(1) | −1(1) |
| C(24A) | 36(2) | 18(1) | 33(1) | 5(1) | 8(1) | −7(1) |
| C(25A) | 21(1) | 28(1) | 28(1) | 9(1) | 5(1) | −5(1) |
| C(26A) | 20(1) | 26(1) | 17(1) | 4(1) | 4(1) | 0(1) |
| C(27A) | 43(2) | 14(1) | 44(2) | −1(1) | 21(1) | 0(1) |
| C(28A) | 30(1) | 30(1) | 33(1) | 7(1) | 17(1) | 4(1) |
| O(1A) | 17(1) | 15(1) | 21(1) | 1(1) | −1(1) | −2(1) |
| C(29A) | 14(1) | 14(1) | 18(1) | 0(1) | 5(1) | 0(1) |
| C(30A) | 18(1) | 14(1) | 16(1) | 0(1) | 3(1) | 0(1) |
| C(31A) | 21(1) | 13(1) | 22(1) | −1(1) | 6(1) | −3(1) |
| C(32A) | 18(1) | 15(1) | 19(1) | −5(1) | 4(1) | −2(1) |
| C(33A) | 23(1) | 19(1) | 26(1) | −1(1) | 2(1) | −7(1) |
| C(34A) | 20(1) | 25(1) | 27(1) | −4(1) | −1(1) | −5(1) |
| C(35A) | 25(1) | 26(1) | 19(1) | −3(1) | 1(1) | 0(1) |
| C(36A) | 21(1) | 19(1) | 17(1) | 1(1) | 1(1) | −1(1) |
| C(37A) | 17(1) | 17(1) | 15(1) | −1(1) | 4(1) | 2(1) |
| C(38A) | 17(1) | 13(1) | 17(1) | 0(1) | 4(1) | 0(1) |
| C(39A) | 16(1) | 13(1) | 15(1) | 3(1) | 0(1) | −1(1) |
| C(40A) | 20(1) | 16(1) | 15(1) | 0(1) | 4(1) | −1(1) |
| C(41A) | 30(1) | 13(1) | 26(1) | 1(1) | 7(1) | 4(1) |
| C(42A) | 32(1) | 16(1) | 26(1) | 3(1) | 8(1) | −2(1) |
| C(43A) | 27(1) | 19(1) | 19(1) | 3(1) | 5(1) | −3(1) |
| C(44A) | 29(1) | 24(1) | 29(1) | 5(1) | 13(1) | −3(1) |
| C(45A) | 23(2) | 28(2) | 26(2) | 6(2) | 8(2) | −2(2) |
| C(46A) | 20(2) | 30(2) | 21(2) | 0(2) | 9(2) | 3(2) |
| C(45B) | 29(5) | 26(4) | 27(5) | 10(3) | 12(4) | 3(4) |
| C(46B) | 27(5) | 30(4) | 25(5) | 5(4) | 12(4) | 14(4) |
| C(47A) | 21(1) | 18(1) | 23(1) | 1(1) | 8(1) | 1(1) |
| C(48A) | 18(1) | 16(1) | 16(1) | 0(1) | 2(1) | 2(1) |
| O(2A) | 21(1) | 15(1) | 19(1) | 0(1) | 5(1) | 0(1) |
| Si(1A) | 17(1) | 17(1) | 18(1) | −2(1) | 4(1) | 1(1) |
| C(49A) | 30(1) | 27(1) | 23(1) | 3(1) | 8(1) | 10(1) |
| C(50A) | 30(2) | 29(1) | 27(1) | −8(1) | 5(1) | −7(1) |
| C(51A) | 16(1) | 23(1) | 23(1) | −3(1) | 4(1) | −1(1) |
| C(52A) | 21(1) | 43(2) | 30(1) | −3(1) | 12(1) | 2(1) |
| C(53A) | 24(1) | 38(2) | 37(2) | 6(1) | 7(1) | 9(1) |
| C(54A) | 26(1) | 34(2) | 40(2) | −7(1) | 5(1) | −5(1) |
| Br(1A) | 27(1) | 20(1) | 22(1) | 8(1) | −1(1) | −3(1) |
| Br(2A) | 46(1) | 15(1) | 44(1) | 6(1) | 22(1) | 9(1) |
| Mo(1) | 15(1) | 11(1) | 15(1) | 1(1) | 0(1) | −1(1) |
| C(1) | 15(1) | 18(1) | 16(1) | 0(1) | 0(1) | −3(1) |
| C(2) | 20(1) | 14(1) | 19(1) | 1(1) | 0(1) | −2(1) |
| C(3) | 28(1) | 17(1) | 29(1) | −3(1) | 4(1) | −3(1) |
| C(4) | 28(1) | 17(1) | 22(1) | 2(1) | 2(1) | 3(1) |
| C(5) | 25(1) | 10(1) | 25(1) | −2(1) | 2(1) | 0(1) |
| C(6) | 29(1) | 24(1) | 24(1) | 1(1) | −1(1) | 5(1) |
| C(7) | 21(1) | 33(2) | 42(2) | 2(1) | 6(1) | 4(1) |
| C(8) | 33(2) | 29(2) | 41(2) | 0(1) | 15(1) | 0(1) |
| C(9) | 37(2) | 29(2) | 25(1) | −3(1) | 9(1) | −4(1) |
| C(10) | 28(1) | 24(1) | 25(1) | −4(1) | 2(1) | −3(1) |
| N(1) | 20(1) | 15(1) | 16(1) | 1(1) | 2(1) | 1(1) |
| C(11) | 22(1) | 12(1) | 16(1) | 2(1) | −1(1) | −1(1) |
| C(12) | 24(1) | 12(1) | 25(1) | −1(1) | −2(1) | 1(1) |
| C(13) | 26(1) | 17(1) | 26(1) | 1(1) | −8(1) | 0(1) |
| C(14) | 40(2) | 18(1) | 19(1) | 4(1) | −8(1) | −4(1) |
| C(15) | 40(2) | 21(1) | 15(1) | 2(1) | 1(1) | −8(1) |
| C(16) | 26(1) | 13(1) | 19(1) | 0(1) | 0(1) | −3(1) |
| C(17) | 20(1) | 23(1) | 28(1) | −3(1) | 1(1) | 0(1) |
| C(18) | 31(2) | 32(2) | 37(2) | −1(1) | 6(1) | −10(1) |
| C(19) | 28(2) | 41(2) | 43(2) | −8(1) | 0(1) | 9(1) |
| C(20) | 28(1) | 26(1) | 18(1) | 1(1) | 6(1) | −6(1) |
| C(21) | 32(2) | 28(2) | 39(2) | −3(1) | 6(1) | 0(1) |
| C(22) | 39(2) | 33(2) | 32(2) | 5(1) | 6(1) | −13(1) |
| N(2) | 18(1) | 13(1) | 18(1) | 0(1) | 0(1) | −1(1) |
| C(23) | 20(1) | 15(1) | 20(1) | 0(1) | −3(1) | −1(1) |
| C(24) | 27(1) | 14(1) | 43(2) | 2(1) | −3(1) | −4(1) |
| C(25) | 18(1) | 23(1) | 40(2) | 5(1) | 4(1) | −4(1) |
| C(26) | 18(1) | 19(1) | 26(1) | 6(1) | 0(1) | −1(1) |
| C(27) | 27(1) | 18(1) | 22(1) | −4(1) | 0(1) | 0(1) |
| C(28) | 22(1) | 23(1) | 31(1) | 4(1) | 6(1) | 0(1) |
| O(1) | 16(1) | 16(1) | 20(1) | 0(1) | −2(1) | −1(1) |
| C(29) | 14(1) | 15(1) | 17(1) | −2(1) | 3(1) | −1(1) |
| C(30) | 16(1) | 16(1) | 18(1) | 1(1) | 4(1) | 2(1) |
| C(31) | 22(1) | 16(1) | 18(1) | −1(1) | 5(1) | −2(1) |
| C(32) | 19(1) | 18(1) | 17(1) | −2(1) | 5(1) | −3(1) |
| C(33) | 22(1) | 23(1) | 22(1) | 2(1) | −1(1) | −8(1) |
| C(34) | 24(1) | 26(1) | 21(1) | −1(1) | −2(1) | −9(1) |
| C(35) | 20(1) | 26(1) | 22(1) | 1(1) | −3(1) | 0(1) |
| C(36) | 21(1) | 19(1) | 19(1) | 3(1) | 1(1) | −2(1) |
| C(37) | 16(1) | 18(1) | 16(1) | 0(1) | 2(1) | 2(1) |
| C(38) | 18(1) | 12(1) | 18(1) | −1(1) | 4(1) | 0(1) |
| C(39) | 15(1) | 13(1) | 15(1) | 0(1) | −2(1) | 0(1) |
| C(40) | 15(1) | 16(1) | 15(1) | 1(1) | 1(1) | −1(1) |
| C(41) | 20(1) | 13(1) | 16(1) | −1(1) | −2(1) | 3(1) |
| C(42) | 20(1) | 16(1) | 20(1) | 3(1) | 2(1) | −4(1) |
| C(43) | 15(1) | 23(1) | 16(1) | 4(1) | 2(1) | −1(1) |
| C(44) | 21(1) | 26(1) | 27(1) | 3(1) | 10(1) | −5(1) |
| C(45) | 26(1) | 28(1) | 28(1) | 4(1) | 12(1) | 2(1) |
| C(46) | 22(1) | 26(1) | 23(1) | 0(1) | 6(1) | 4(1) |
| C(47) | 21(1) | 20(1) | 18(1) | 0(1) | 5(1) | 3(1) |
| C(48) | 15(1) | 17(1) | 14(1) | 2(1) | −1(1) | 2(1) |
| O(2) | 18(1) | 17(1) | 20(1) | −2(1) | 5(1) | 0(1) |
| Si(1) | 24(1) | 17(1) | 22(1) | −2(1) | 9(1) | −2(1) |
| C(49) | 44(2) | 21(1) | 36(2) | 6(1) | 19(1) | 3(1) |

TABLE 16-continued

Anisotropic displacement parameters (Å² × 10³) for 07190.
The anisotropic displacement factor exponent takes the form:
$-2p^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| C(50) | 46(2) | 34(2) | 23(1) | −2(1) | 2(1) | −9(1) |
| C(51) | 28(1) | 30(2) | 34(2) | −6(1) | 17(1) | 0(1) |
| C(52) | 23(2) | 71(3) | 93(3) | −45(2) | 12(2) | −9(2) |
| C(53) | 48(2) | 45(2) | 52(2) | 5(2) | 35(2) | 3(2) |
| C(54) | 41(2) | 46(2) | 56(2) | 16(2) | 30(2) | 25(2) |
| Br(1) | 23(1) | 18(1) | 23(1) | 6(1) | −1(1) | −1(1) |
| Br(2) | 30(1) | 13(1) | 27(1) | −2(1) | 7(1) | 2(1) |
| C(1S) | 61(3) | 42(2) | 76(3) | −20(2) | −3(2) | 7(2) |
| C(2S) | 36(2) | 31(2) | 53(2) | −1(2) | 2(2) | 5(1) |
| C(3S) | 29(1) | 27(1) | 33(2) | 6(1) | 7(1) | 1(1) |
| C(4S) | 38(2) | 37(2) | 32(2) | 10(1) | 7(1) | −3(1) |
| C(5S) | 52(2) | 44(2) | 29(2) | 1(1) | 9(1) | 5(2) |
| C(6S) | 35(2) | 41(2) | 38(2) | −9(1) | 5(1) | −11(1) |
| C(7S) | 52(2) | 63(3) | 76(3) | 13(2) | 1(2) | −14(2) |
| C(8S) | 57(2) | 32(2) | 62(2) | −1(2) | −4(2) | −5(2) |
| C(9S) | 60(2) | 51(2) | 52(2) | 7(2) | −3(2) | 13(2) |
| C(10S) | 72(3) | 56(3) | 89(3) | −15(2) | −8(2) | 9(2) |

TABLE 17

Hydrogen coordinates (×10⁴) and isotropic displacement parameters
(Å² × 10³) for 07190

| | x | y | z | U(eq) |
|---|---|---|---|---|
| H(1A) | 6426(17) | −1469(19) | 5984(6) | 23 |
| H(3AA) | 7797 | −1919 | 7275 | 40 |
| H(3AB) | 7637 | −3003 | 7237 | 40 |
| H(3AC) | 6779 | −2330 | 7221 | 40 |
| H(4AA) | 6407 | −3120 | 5958 | 51 |
| H(4AB) | 5950 | −3062 | 6432 | 51 |
| H(4AC) | 6814 | −3725 | 6446 | 51 |
| H(6AA) | 8991 | −2051 | 7017 | 42 |
| H(7AA) | 10337 | −2073 | 6721 | 59 |
| H(8AA) | 10278 | −2442 | 5887 | 76 |
| H(9AA) | 8843 | −2797 | 5349 | 74 |
| H(10A) | 7504 | −2780 | 5645 | 52 |
| H(13A) | 9303 | −189 | 8462 | 28 |
| H(14A) | 8388 | −224 | 9047 | 28 |
| H(15A) | 6786 | −138 | 8791 | 27 |
| H(17A) | 8516 | −398 | 7148 | 28 |
| H(18A) | 9822 | −1018 | 7719 | 56 |
| H(18B) | 10144 | −9 | 7911 | 56 |
| H(18C) | 10137 | −305 | 7347 | 56 |
| H(19A) | 8153 | 1180 | 7183 | 45 |
| H(19B) | 9115 | 1049 | 7020 | 45 |
| H(19C) | 9111 | 1348 | 7582 | 45 |
| H(20A) | 5481 | −338 | 7507 | 26 |
| H(21A) | 5403 | −1424 | 8137 | 60 |
| H(21B) | 4507 | −780 | 8025 | 60 |
| H(21C) | 5314 | −613 | 8516 | 60 |
| H(22A) | 5622 | 1245 | 7712 | 51 |
| H(22B) | 5447 | 1026 | 8256 | 51 |
| H(22C) | 4640 | 858 | 7765 | 51 |
| H(24A) | 7478 | 2725 | 6069 | 35 |
| H(25A) | 8531 | 1648 | 5732 | 31 |
| H(27A) | 6087 | 2495 | 6540 | 48 |
| H(27B) | 6246 | 1577 | 6867 | 48 |
| H(27C) | 5520 | 1588 | 6335 | 48 |
| H(28A) | 8692 | −141 | 5652 | 44 |
| H(28B) | 7693 | −607 | 5576 | 44 |
| H(28C) | 8405 | −650 | 6112 | 44 |
| H(31A) | 3085 | −2550 | 6148 | 22 |
| H(33A) | 1571 | −2467 | 5580 | 28 |
| H(33B) | 2023 | −2618 | 5108 | 28 |
| H(34A) | 593 | −1920 | 4805 | 30 |
| H(34B) | 821 | −1136 | 5226 | 30 |
| H(35A) | 1051 | −602 | 4434 | 29 |
| H(35B) | 1831 | −1370 | 4456 | 29 |
| H(36A) | 2643 | −69 | 4736 | 24 |
| H(36B) | 1946 | 212 | 5078 | 24 |

TABLE 17-continued

Hydrogen coordinates (×10⁴) and isotropic displacement parameters
(Å² × 10³) for 07190

| | x | y | z | U(eq) |
|---|---|---|---|---|
| H(42A) | 4337 | 3026 | 5122 | 29 |
| H(44A) | 5221 | 2166 | 4494 | 32 |
| H(44B) | 5927 | 2414 | 5011 | 32 |
| H(44C) | 6099 | 2110 | 5071 | 32 |
| H(44D) | 5318 | 2443 | 4597 | 32 |
| H(45A) | 6590 | 1000 | 5079 | 30 |
| H(45B) | 6446 | 1239 | 4494 | 30 |
| H(46A) | 5878 | −247 | 4547 | 28 |
| H(46B) | 5003 | 400 | 4333 | 28 |
| H(45C) | 5175 | 934 | 4249 | 32 |
| H(45D) | 6258 | 1188 | 4377 | 32 |
| H(46C) | 6119 | −271 | 4715 | 32 |
| H(46D) | 6437 | 424 | 5174 | 32 |
| H(47A) | 4657 | −505 | 4981 | 24 |
| H(47B) | 5597 | −193 | 5361 | 24 |
| H(47C) | 5289 | −413 | 5365 | 24 |
| H(47D) | 4655 | −323 | 4810 | 24 |
| H(49A) | 3734 | 155 | 6823 | 39 |
| H(49B) | 2732 | −302 | 6647 | 39 |
| H(49C) | 2994 | 261 | 7162 | 39 |
| H(50A) | 4004 | 2158 | 6771 | 43 |
| H(50B) | 3302 | 2329 | 7127 | 43 |
| H(50C) | 3145 | 2838 | 6596 | 43 |
| H(52A) | 585 | 1713 | 6985 | 46 |
| H(52B) | 1572 | 2212 | 7110 | 46 |
| H(52C) | 1503 | 1140 | 7216 | 46 |
| H(53A) | 262 | 2266 | 6112 | 50 |
| H(53B) | 981 | 2087 | 5767 | 50 |
| H(53C) | 1236 | 2789 | 6226 | 50 |
| H(54A) | 186 | 599 | 6273 | 50 |
| H(54B) | 1106 | 33 | 6509 | 50 |
| H(54C) | 918 | 383 | 5940 | 50 |
| H(1) | 1437(17) | −1061(18) | 848(7) | 20 |
| H(3A) | 1028 | −2663 | 628 | 38 |
| H(3B) | 798 | −2779 | 1168 | 38 |
| H(3C) | 1498 | −3472 | 993 | 38 |
| H(4A) | 2998 | −2095 | 1910 | 34 |
| H(4B) | 2690 | −3128 | 1765 | 34 |
| H(4C) | 1988 | −2437 | 1940 | 34 |
| H(6A) | 3982 | −2298 | 1457 | 32 |
| H(7A) | 5060 | −2262 | 958 | 38 |
| H(8A) | 4576 | −2219 | 89 | 40 |
| H(9A) | 2991 | −2168 | −284 | 36 |
| H(10B) | 1916 | −2179 | 213 | 31 |
| H(13B) | 4542 | −588 | 3376 | 30 |
| H(14B) | 3693 | −614 | 3991 | 34 |
| H(15B) | 2089 | −551 | 3779 | 32 |
| H(17B) | 3568 | −593 | 2046 | 29 |
| H(18D) | 4667 | 604 | 2085 | 50 |
| H(18E) | 4695 | 740 | 2668 | 50 |
| H(18F) | 3765 | 954 | 2256 | 50 |
| H(19D) | 4581 | −1735 | 2471 | 59 |
| H(19E) | 5257 | −958 | 2763 | 59 |
| H(19F) | 5106 | −1061 | 2168 | 59 |
| H(20B) | 683 | −586 | 2511 | 29 |
| H(21D) | 815 | 914 | 2853 | 50 |
| H(21E) | 701 | 513 | 3379 | 50 |
| H(21F) | −141 | 451 | 2896 | 50 |
| H(22D) | 700 | −1868 | 3042 | 52 |
| H(22E) | −210 | −1265 | 3016 | 52 |
| H(22F) | 636 | −1201 | 3497 | 52 |
| H(24B) | 2655 | 2959 | 1406 | 36 |
| H(25B) | 3735 | 2060 | 989 | 33 |
| H(27D) | 1211 | 2522 | 1799 | 35 |
| H(27E) | 1317 | 1504 | 2020 | 35 |
| H(27F) | 657 | 1697 | 1480 | 35 |
| H(28D) | 3950 | 326 | 769 | 38 |
| H(28E) | 2979 | −202 | 648 | 38 |
| H(28F) | 3668 | −306 | 1188 | 38 |
| H(31B) | −1996 | −2242 | 984 | 22 |
| H(33C) | −3706 | −1515 | 422 | 28 |
| H(33D) | −3127 | −2186 | 147 | 28 |
| H(34C) | −4232 | −1239 | −426 | 31 |
| H(34D) | −3198 | −1167 | −508 | 31 |
| H(35C) | −3978 | 131 | 70 | 28 |

TABLE 17-continued

Hydrogen coordinates (×10⁴) and isotropic displacement parameters ($\text{Å}^2 \times 10^3$) for 07190

| | x | y | z | U(eq) |
|---|---|---|---|---|
| H(35D) | −3880 | 320 | −493 | 28 |
| H(36C) | −2296 | 392 | −254 | 25 |
| H(36D) | −2643 | 975 | 162 | 25 |
| H(42B) | 117 | 3356 | 532 | 22 |
| H(44E) | 1569 | 2278 | 320 | 29 |
| H(44F) | 856 | 2755 | −136 | 29 |
| H(45E) | 613 | 1415 | −590 | 32 |
| H(45F) | 1713 | 1470 | −377 | 32 |
| H(46E) | 1586 | 475 | 296 | 28 |
| H(46F) | 1219 | −15 | −237 | 28 |
| H(47E) | −317 | 220 | −210 | 24 |
| H(47F) | 181 | −211 | 321 | 24 |
| H(49D) | −1192 | 161 | 1915 | 48 |
| H(49E) | −2223 | −106 | 1627 | 48 |
| H(49F) | −2019 | 216 | 2201 | 48 |
| H(50D) | −640 | 2060 | 2154 | 53 |
| H(50E) | −1430 | 2186 | 2461 | 53 |
| H(50F) | −1362 | 2888 | 2022 | 53 |
| H(52D) | −4584 | 1245 | 1228 | 94 |
| H(52E) | −3808 | 485 | 1424 | 94 |
| H(52F) | −3777 | 1080 | 937 | 94 |
| H(53D) | −4220 | 1972 | 2073 | 67 |
| H(53E) | −3182 | 2271 | 2329 | 67 |
| H(53F) | −3446 | 1209 | 2266 | 67 |
| H(54D) | −4202 | 2892 | 1328 | 67 |
| H(54E) | −3400 | 2761 | 1031 | 67 |
| H(54F) | −3170 | 3220 | 1576 | 67 |
| H(1SA) | −3286 | −5481 | 505 | 94 |
| H(1SB) | −3531 | −4453 | 320 | 94 |
| H(1SC) | −4208 | −5005 | 593 | 94 |
| H(2SA) | −2373 | −4459 | 1071 | 50 |
| H(2SB) | −3049 | −5011 | 1345 | 50 |
| H(3SA) | −3405 | −3193 | 962 | 36 |
| H(3SB) | −4066 | −3744 | 1245 | 36 |
| H(4SA) | −2224 | −3218 | 1724 | 43 |
| H(4SB) | −2949 | −3684 | 1998 | 43 |
| H(5SA) | −2864 | −2104 | 2166 | 63 |
| H(5SB) | −3883 | −2351 | 1850 | 63 |
| H(5SC) | −3153 | −1884 | 1578 | 63 |
| H(6SA) | −241 | 5468 | 5109 | 58 |
| H(6SB) | 764 | 5323 | 5000 | 58 |
| H(6SC) | 506 | 6276 | 5222 | 58 |
| H(7SA) | 406 | 5524 | 5981 | 79 |
| H(7SB) | 669 | 4576 | 5760 | 79 |
| H(8SA) | 1862 | 6085 | 5988 | 64 |
| H(8SB) | 2125 | 5139 | 5763 | 64 |
| H(9SA) | 1767 | 5352 | 6741 | 68 |
| H(9SB) | 1969 | 4381 | 6516 | 68 |
| H(10C) | 3336 | 4974 | 7042 | 115 |
| H(10D) | 3264 | 5860 | 6691 | 115 |
| H(10E) | 3465 | 4879 | 6479 | 115 |

TABLE 18

Torsion angles [°] for 07190

| | |
|---|---|
| N(1A)—Mo(1A)—C(1A)—C(2A) | 8.8 (3) |
| O(1A)—Mo(1A)—C(1A)—C(2A) | −114.6 (3) |
| N(2A)—Mo(1A)—C(1A)—C(2A) | 121.2 (3) |
| Mo(1A)—C(1A)—C(2A)—C(5A) | −115.7 (3) |
| Mo(1A)—C(1A)—C(2A)—C(3A) | 7.4 (4) |
| Mo(1A)—C(1A)—C(2A)—C(4A) | 124.5 (3) |
| C(1A)—C(2A)—C(5A)—C(10A) | −76.6 (3) |
| C(3A)—C(2A)—C(5A)—C(10A) | 161.9 (3) |
| C(4A)—C(2A)—C(5A)—C(10A) | 41.8 (3) |
| C(1A)—C(2A)—C(5A)—C(6A) | 99.3 (3) |
| C(3A)—C(2A)—C(5A)—C(6A) | −22.2 (3) |
| C(4A)—C(2A)—C(5A)—C(6A) | −142.3 (3) |
| C(10A)—C(5A)—C(6A)—C(7A) | −0.3 (4) |
| C(2A)—C(5A)—C(6A)—C(7A) | −176.3 (3) |
| C(5A)—C(6A)—C(7A)—C(8A) | 0.3 (5) |
| C(6A)—C(7A)—C(8A)—C(9A) | −0.1 (6) |

TABLE 18-continued

Torsion angles [°] for 07190

| | |
|---|---|
| C(7A)—C(8A)—C(9A)—C(10A) | 0.0 (6) |
| C(8A)—C(9A)—C(10A)—C(5A) | 0.0 (6) |
| C(6A)—C(5A)—C(10A)—C(9A) | 0.1 (5) |
| C(2A)—C(5A)—C(10A)—C(9A) | 176.2 (3) |
| C(1A)—Mo(1A)—N(1A)—C(11A) | 118 (4) |
| O(1A)—Mo(1A)—N(1A)—C(11A) | −123 (4) |
| N(2A)—Mo(1A)—N(1A)—C(11A) | 8 (4) |
| Mo(1A)—N(1A)—C(11A)—C(16A) | 129 (4) |
| Mo(1A)—N(1A)—C(11A)—C(12A) | −52 (4) |
| N(1A)—C(11A)—C(12A)—C(13A) | −174.0 (2) |
| C(16A)—C(11A)—C(12A)—C(13A) | 5.3 (4) |
| N(1A)—C(11A)—C(12A)—C(17A) | 9.3 (3) |
| C(16A)—C(11A)—C(12A)—C(17A) | −171.4 (2) |
| C(11A)—C(12A)—C(13A)—C(14A) | −3.4 (4) |
| C(17A)—C(12A)—C(13A)—C(14A) | 173.3 (2) |
| C(12A)—C(13A)—C(14A)—C(15A) | −1.1 (4) |
| C(13A)—C(14A)—C(15A)—C(16A) | 4.0 (4) |
| C(14A)—C(15A)—C(16A)—C(11A) | −2.1 (4) |
| C(14A)—C(15A)—C(16A)—C(20A) | −180.0 (2) |
| N(1A)—C(11A)—C(16A)—C(15A) | 176.7 (2) |
| C(12A)—C(11A)—C(16A)—C(15A) | −2.6 (4) |
| N(1A)—C(11A)—C(16A)—C(20A) | −5.5 (3) |
| C(12A)—C(11A)—C(16A)—C(20A) | 175.3 (2) |
| C(13A)—C(12A)—C(17A)—C(18A) | 26.2 (4) |
| C(11A)—C(12A)—C(17A)—C(18A) | −157.2 (2) |
| C(13A)—C(12A)—C(17A)—C(19A) | −97.9 (3) |
| C(11A)—C(12A)—C(17A)—C(19A) | 78.7 (3) |
| C(15A)—C(16A)—C(20A)—C(21A) | −45.7 (3) |
| C(11A)—C(16A)—C(20A)—C(21A) | 136.6 (3) |
| C(15A)—C(16A)—C(20A)—C(22A) | 78.1 (3) |
| C(11A)—C(16A)—C(20A)—C(22A) | −99.6 (3) |
| N(1A)—Mo(1A)—N(2A)—C(26A) | 96.0 (2) |
| C(1A)—Mo(1A)—N(2A)—C(26A) | −12.4 (3) |
| O(1A)—Mo(1A)—N(2A)—C(26A) | −132.6 (2) |
| N(1A)—Mo(1A)—N(2A)—C(23A) | −73.23 (18) |
| C(1A)—Mo(1A)—N(2A)—C(23A) | 178.38 (17) |
| O(1A)—Mo(1A)—N(2A)—C(23A) | 58.14 (19) |
| C(26A)—N(2A)—C(23A)—C(24A) | 0.5 (3) |
| Mo(1A)—N(2A)—C(23A)—C(24A) | 172.87 (17) |
| C(26A)—N(2A)—C(23A)—C(27A) | −179.9 (2) |
| Mo(1A)—N(2A)—C(23A)—C(27A) | −7.5 (3) |
| N(2A)—C(23A)—C(24A)—C(25A) | −0.9 (3) |
| C(27A)—C(23A)—C(24A)—C(25A) | 179.5 (3) |
| C(23A)—C(24A)—C(25A)—C(26A) | 1.1 (3) |
| C(24A)—C(25A)—C(26A)—N(2A) | −0.8 (3) |
| C(24A)—C(25A)—C(26A)—C(28A) | 178.2 (3) |
| C(23A)—N(2A)—C(26A)—C(25A) | 0.2 (3) |
| Mo(1A)—N(2A)—C(26A)—C(25A) | −169.68 (19) |
| C(23A)—N(2A)—C(26A)—C(28A) | −178.9 (2) |
| Mo(1A)—N(2A)—C(26A)—C(28A) | 11.2 (4) |
| N(1A)—Mo(1A)—O(1A)—C(29A) | −120.5 (2) |
| C(1A)—Mo(1A)—O(1A)—C(29A) | −5.6 (2) |
| N(2A)—Mo(1A)—O(1A)—C(29A) | 112.2 (2) |
| Mo(1A)—O(1A)—C(29A)—C(30A) | 65.8 (3) |
| Mo(1A)—O(1A)—C(29A)—C(38A) | −119.9 (2) |
| O(1A)—C(29A)—C(30A)—C(31A) | 177.5 (2) |
| C(38A)—C(29A)—C(30A)—C(31A) | 3.2 (3) |
| O(1A)—C(29A)—C(30A)—Br(1A) | 3.1 (3) |
| C(38A)—C(29A)—C(30A)—Br(1A) | −171.18 (16) |
| C(29A)—C(30A)—C(31A)—C(32A) | −0.4 (4) |
| Br(1A)—C(30A)—C(31A)—C(32A) | 174.07 (17) |
| C(30A)—C(31A)—C(32A)—C(37A) | −1.7 (3) |
| C(30A)—C(31A)—C(32A)—C(33A) | 179.1 (2) |
| C(31A)—C(32A)—C(33A)—C(34A) | 156.3 (2) |
| C(37A)—C(32A)—C(33A)—C(34A) | −22.8 (3) |
| C(32A)—C(33A)—C(34A)—C(35A) | 51.7 (3) |
| C(33A)—C(34A)—C(35A)—C(36A) | −63.8 (3) |
| C(34A)—C(35A)—C(36A)—C(37A) | 44.3 (3) |
| C(31A)—C(32A)—C(37A)—C(38A) | 1.1 (3) |
| C(33A)—C(32A)—C(37A)—C(38A) | −179.8 (2) |
| C(31A)—C(32A)—C(37A)—C(36A) | −175.8 (2) |
| C(33A)—C(32A)—C(37A)—C(36A) | 3.3 (3) |
| C(35A)—C(36A)—C(37A)—C(32A) | −13.9 (3) |
| C(35A)—C(36A)—C(37A)—C(38A) | 169.3 (2) |
| O(1A)—C(29A)—C(38A)—C(37A) | −178.2 (2) |
| C(30A)—C(29A)—C(38A)—C(37A) | −3.8 (3) |
| O(1A)—C(29A)—C(38A)—C(39A) | −1.4 (3) |
| C(30A)—C(29A)—C(38A)—C(39A) | 173.0 (2) |

TABLE 18-continued

Torsion angles [°] for 07190

| | |
|---|---|
| C(32A)—C(37A)—C(38A)—C(29A) | 1.7 (3) |
| C(36A)—C(37A)—C(38A)—C(29A) | 178.6 (2) |
| C(32A)—C(37A)—C(38A)—C(39A) | −175.0 (2) |
| C(36A)—C(37A)—C(38A)—C(39A) | 1.8 (3) |
| C(29A)—C(38A)—C(39A)—C(48A) | 79.0 (3) |
| C(37A)—C(38A)—C(39A)—C(48A) | −104.1 (3) |
| C(29A)—C(38A)—C(39A)—C(40A) | −101.9 (3) |
| C(37A)—C(38A)—C(39A)—C(40A) | 74.9 (3) |
| C(48A)—C(39A)—C(40A)—O(2A) | 176.0 (2) |
| C(38A)—C(39A)—C(40A)—O(2A) | −3.1 (3) |
| C(48A)—C(39A)—C(40A)—C(41A) | 1.6 (3) |
| C(38A)—C(39A)—C(40A)—C(41A) | −177.4 (2) |
| O(2A)—C(40A)—C(41A)—C(42A) | −177.7 (2) |
| C(39A)—C(40A)—C(41A)—C(42A) | −3.4 (4) |
| O(2A)—C(40A)—C(41A)—Br(2A) | −1.5 (3) |
| C(39A)—C(40A)—C(41A)—Br(2A) | 172.85 (17) |
| C(40A)—C(41A)—C(42A)—C(43A) | 1.4 (4) |
| Br(2A)—C(41A)—C(42A)—C(43A) | −174.89 (19) |
| C(41A)—C(42A)—C(43A)—C(48A) | 2.4 (4) |
| C(41A)—C(42A)—C(43A)—C(44A) | 179.2 (2) |
| C(42A)—C(43A)—C(44A)—C(45A) | 175.9 (3) |
| C(48A)—C(43A)—C(44A)—C(45A) | −7.5 (4) |
| C(42A)—C(43A)—C(44A)—C(45B) | −152.7 (5) |
| C(48A)—C(43A)—C(44A)—C(45B) | 23.9 (5) |
| C(43A)—C(44A)—C(45A)—C(46A) | 41.8 (5) |
| C(45B)—C(44A)—C(45A)—C(46A) | −47.6 (7) |
| C(44A)—C(45A)—C(46A)—C(47A) | −66.1 (5) |
| C(45A)—C(44A)—C(45B)—C(46B) | 50.2 (7) |
| C(43A)—C(44A)—C(45B)—C(46B) | −52.7 (9) |
| C(44A)—C(45B)—C(46B)—C(47A) | 65.4 (11) |
| C(45B)—C(46B)—C(47A)—C(48A) | −45.8 (10) |
| C(45B)—C(46B)—C(47A)—C(46A) | 45.1 (7) |
| C(45A)—C(46A)—C(47A)—C(46B) | −48.3 (7) |
| C(45A)—C(46A)—C(47A)—C(48A) | 54.5 (4) |
| C(40A)—C(39A)—C(48A)—C(43A) | 2.2 (3) |
| C(38A)—C(39A)—C(48A)—C(43A) | −178.8 (2) |
| C(40A)—C(39A)—C(48A)—C(47A) | −174.7 (2) |
| C(38A)—C(39A)—C(48A)—C(47A) | 4.3 (3) |
| C(42A)—C(43A)—C(48A)—C(39A) | −4.2 (4) |
| C(44A)—C(43A)—C(48A)—C(39A) | 179.2 (2) |
| C(42A)—C(43A)—C(48A)—C(47A) | 172.7 (2) |
| C(44A)—C(43A)—C(48A)—C(47A) | −3.9 (4) |
| C(46B)—C(47A)—C(48A)—C(39A) | −168.7 (5) |
| C(46A)—C(47A)—C(48A)—C(39A) | 157.1 (3) |
| C(46B)—C(47A)—C(48A)—C(43A) | 14.4 (6) |
| C(46A)—C(47A)—C(48A)—C(43A) | −19.8 (4) |
| C(41A)—C(40A)—O(2A)—Si(1A) | −87.1 (3) |
| C(39A)—C(40A)—O(2A)—Si(1A) | 98.7 (2) |
| C(40A)—O(2A)—Si(1A)—C(50A) | 35.8 (2) |
| C(40A)—O(2A)—Si(1A)—C(49A) | −83.8 (2) |
| C(40A)—O(2A)—Si(1A)—C(51A) | 158.3 (2) |
| O(2A)—Si(1A)—C(51A)—C(53A) | −52.3 (2) |
| C(50A)—Si(1A)—C(51A)—C(53A) | 67.8 (2) |
| C(49A)—Si(1A)—C(51A)—C(53A) | −171.02 (19) |
| O(2A)—Si(1A)—C(51A)—C(52A) | −171.93 (18) |
| C(50A)—Si(1A)—C(51A)—C(52A) | −51.9 (2) |
| C(49A)—Si(1A)—C(51A)—C(52A) | 69.3 (2) |
| O(2A)—Si(1A)—C(51A)—C(54A) | 69.11 (19) |
| C(50A)—Si(1A)—C(51A)—C(54A) | −170.84 (18) |
| C(49A)—Si(1A)—C(51A)—C(54A) | −49.6 (2) |
| N(1)—Mo(1)—C(1)—C(2) | 11.8 (3) |
| O(1)—Mo(1)—C(1)—C(2) | −109.9 (3) |
| N(2)—Mo(1)—C(1)—C(2) | 122.9 (3) |
| Mo(1)—C(1)—C(2)—C(4) | −5.8 (4) |
| Mo(1)—C(1)—C(2)—C(5) | −129.6 (3) |
| Mo(1)—C(1)—C(2)—C(3) | 112.2 (3) |
| C(1)—C(2)—C(5)—C(6) | 104.8 (3) |
| C(4)—C(2)—C(5)—C(6) | −17.7 (3) |
| C(3)—C(2)—C(5)—C(6) | −138.4 (2) |
| C(1)—C(2)—C(5)—C(10) | −72.3 (3) |
| C(4)—C(2)—C(5)—C(10) | 165.3 (2) |
| C(3)—C(2)—C(5)—C(10) | 44.5 (3) |
| C(10)—C(5)—C(6)—C(7) | 0.6 (4) |
| C(2)—C(5)—C(6)—C(7) | −176.5 (2) |
| C(5)—C(6)—C(7)—C(8) | −1.0 (4) |
| C(6)—C(7)—C(8)—C(9) | 0.9 (4) |
| C(7)—C(8)—C(9)—C(10) | −0.3 (4) |
| C(8)—C(9)—C(10)—C(5) | −0.1 (4) |
| C(6)—C(5)—C(10)—C(9) | 0.0 (4) |
| C(2)—C(5)—C(10)—C(9) | 177.2 (2) |
| C(1)—Mo(1)—N(1)—C(11) | 137.5 (12) |
| O(1)—Mo(1)—N(1)—C(11) | −106.1 (12) |
| N(2)—Mo(1)—N(1)—C(11) | 27.9 (12) |
| Mo(1)—N(1)—C(11)—C(12) | −73.1 (12) |
| Mo(1)—N(1)—C(11)—C(16) | 104.8 (12) |
| N(1)—C(11)—C(12)—C(13) | 178.5 (2) |
| C(16)—C(11)—C(12)—C(13) | 0.7 (3) |
| N(1)—C(11)—C(12)—C(17) | 1.8 (3) |
| C(16)—C(11)—C(12)—C(17) | −176.0 (2) |
| C(11)—C(12)—C(13)—C(14) | −1.0 (4) |
| C(17)—C(12)—C(13)—C(14) | 175.7 (2) |
| C(12)—C(13)—C(14)—C(15) | 0.0 (4) |
| C(13)—C(14)—C(15)—C(16) | 1.5 (4) |
| C(14)—C(15)—C(16)—C(11) | −1.7 (4) |
| C(14)—C(15)—C(16)—C(20) | 179.6 (2) |
| N(1)—C(11)—C(16)—C(15) | −177.1 (2) |
| C(12)—C(11)—C(16)—C(15) | 0.7 (3) |
| N(1)—C(11)—C(16)—C(20) | 1.5 (3) |
| C(12)—C(11)—C(16)—C(20) | 179.3 (2) |
| C(13)—C(12)—C(17)—C(19) | 46.6 (3) |
| C(11)—C(12)—C(17)—C(19) | −136.8 (2) |
| C(13)—C(12)—C(17)—C(18) | −79.1 (3) |
| C(11)—C(12)—C(17)—C(18) | 97.5 (3) |
| C(15)—C(16)—C(20)—C(22) | −53.1 (3) |
| C(11)—C(16)—C(20)—C(22) | 128.3 (2) |
| C(15)—C(16)—C(20)—C(21) | 70.9 (3) |
| C(11)—C(16)—C(20)—C(21) | −107.6 (3) |
| N(1)—Mo(1)—N(2)—C(26) | 90.2 (2) |
| C(1)—Mo(1)—N(2)—C(26) | −18.5 (3) |
| O(1)—Mo(1)—N(2)—C(26) | −138.0 (2) |
| N(1)—Mo(1)—N(2)—C(23) | −80.10 (17) |
| C(1)—Mo(1)—N(2)—C(23) | 171.14 (16) |
| O(1)—Mo(1)—N(2)—C(23) | 51.61 (18) |
| C(26)—N(2)—C(23)—C(24) | 1.1 (3) |
| Mo(1)—N(2)—C(23)—C(24) | 174.39 (17) |
| C(26)—N(2)—C(23)—C(27) | 178.1 (2) |
| Mo(1)—N(2)—C(23)—C(27) | −8.7 (3) |
| N(2)—C(23)—C(24)—C(25) | −1.1 (3) |
| C(27)—C(23)—C(24)—C(25) | −177.7 (2) |
| C(23)—C(24)—C(25)—C(26) | 0.7 (3) |
| C(24)—C(25)—C(26)—N(2) | 0.0 (3) |
| C(24)—C(25)—C(26)—C(28) | −176.4 (3) |
| C(23)—N(2)—C(26)—C(25) | −0.7 (3) |
| Mo(1)—N(2)—C(26)—C(25) | −171.57 (19) |
| C(23)—N(2)—C(26)—C(28) | 176.0 (2) |
| Mo(1)—N(2)—C(26)—C(28) | 5.2 (4) |
| N(1)—Mo(1)—O(1)—C(29) | −120.8 (2) |
| C(1)—Mo(1)—O(1)—C(29) | −6.7 (3) |
| N(2)—Mo(1)—O(1)—C(29) | 111.3 (2) |
| Mo(1)—O(1)—C(29)—C(30) | 73.0 (3) |
| Mo(1)—O(1)—C(29)—C(38) | −111.2 (2) |
| O(1)—C(29)—C(30)—C(31) | 178.4 (2) |
| C(38)—C(29)—C(30)—C(31) | 2.6 (3) |
| O(1)—C(29)—C(30)—Br(1) | 3.2 (3) |
| C(38)—C(29)—C(30)—Br(1) | −172.52 (17) |
| C(29)—C(30)—C(31)—C(32) | −1.4 (4) |
| Br(1)—C(30)—C(31)—C(32) | 173.80 (17) |
| C(30)—C(31)—C(32)—C(37) | −1.1 (3) |
| C(30)—C(31)—C(32)—C(33) | −179.7 (2) |
| C(31)—C(32)—C(33)—C(34) | −163.8 (2) |
| C(37)—C(32)—C(33)—C(34) | 17.7 (3) |
| C(32)—C(33)—C(34)—C(35) | −48.8 (3) |
| C(33)—C(34)—C(35)—C(36) | 63.5 (3) |
| C(34)—C(35)—C(36)—C(37) | −45.0 (3) |
| C(31)—C(32)—C(37)—C(38) | 2.3 (3) |
| C(33)—C(32)—C(37)—C(38) | −179.2 (2) |
| C(31)—C(32)—C(37)—C(36) | −178.1 (2) |
| C(33)—C(32)—C(37)—C(36) | 0.4 (3) |
| C(35)—C(36)—C(37)—C(32) | 13.5 (3) |
| C(35)—C(36)—C(37)—C(38) | −166.9 (2) |
| O(1)—C(29)—C(38)—C(37) | −177.3 (2) |
| C(30)—C(29)—C(38)—C(37) | −1.4 (3) |
| O(1)—C(29)—C(38)—C(39) | 1.4 (3) |
| C(30)—C(29)—C(38)—C(39) | 177.3 (2) |
| C(32)—C(37)—C(38)—C(29) | −1.0 (3) |
| C(36)—C(37)—C(38)—C(29) | 179.4 (2) |

TABLE 18-continued

Torsion angles [°] for 07190

| | |
|---|---|
| C(32)—C(37)—C(38)—C(39) | −179.7 (2) |
| C(36)—C(37)—C(38)—C(39) | 0.7 (3) |
| C(29)—C(38)—C(39)—C(40) | −96.6 (3) |
| C(37)—C(38)—C(39)—C(40) | 82.1 (3) |
| C(29)—C(38)—C(39)—C(48) | 80.5 (3) |
| C(37)—C(38)—C(39)—C(48) | −100.7 (3) |
| C(48)—C(39)—C(40)—O(2) | 174.18 (19) |
| C(38)—C(39)—C(40)—O(2) | −8.7 (3) |
| C(48)—C(39)—C(40)—C(41) | −0.3 (3) |
| C(38)—C(39)—C(40)—C(41) | 176.8 (2) |
| O(2)—C(40)—C(41)—C(42) | −176.0 (2) |
| C(39)—C(40)—C(41)—C(42) | −1.5 (3) |
| O(2)—C(40)—C(41)—Br(2) | 3.5 (3) |
| C(39)—C(40)—C(41)—Br(2) | 178.00 (16) |
| C(40)—C(41)—C(42)—C(43) | 2.1 (3) |
| Br(2)—C(41)—C(42)—C(43) | −177.41 (17) |
| C(41)—C(42)—C(43)—C(48) | −0.8 (3) |
| C(41)—C(42)—C(43)—C(44) | −178.5 (2) |
| C(42)—C(43)—C(44)—C(45) | −164.5 (2) |
| C(48)—C(43)—C(44)—C(45) | 17.9 (3) |
| C(43)—C(44)—C(45)—C(46) | −45.8 (3) |
| C(44)—C(45)—C(46)—C(47) | 62.8 (3) |
| C(45)—C(46)—C(47)—C(48) | −50.2 (3) |
| C(42)—C(43)—C(48)—C(39) | −1.1 (3) |
| C(44)—C(43)—C(48)—C(39) | 176.6 (2) |
| C(42)—C(43)—C(48)—C(47) | 176.3 (2) |
| C(44)—C(43)—C(48)—C(47) | −6.0 (3) |
| C(40)—C(39)—C(48)—C(43) | 1.6 (3) |
| C(38)—C(39)—C(48)—C(43) | −175.5 (2) |
| C(40)—C(39)—C(48)—C(47) | −175.8 (2) |
| C(38)—C(39)—C(48)—C(47) | 7.1 (3) |
| C(46)—C(47)—C(48)—C(43) | 22.1 (3) |
| C(46)—C(47)—C(48)—C(39) | −160.5 (2) |
| C(41)—C(40)—O(2)—Si(1) | −88.9 (3) |
| C(39)—C(40)—O(2)—Si(1) | 96.8 (3) |
| C(40)—O(2)—Si(1)—C(50) | 42.1 (3) |
| C(40)—O(2)—Si(1)—C(49) | −78.2 (3) |
| C(40)—O(2)—Si(1)—C(51) | 163.2 (2) |
| O(2)—Si(1)—C(51)—C(53) | −173.1 (2) |
| C(50)—Si(1)—C(51)—C(53) | −53.2 (2) |
| C(49)—Si(1)—C(51)—C(53) | 67.5 (2) |
| O(2)—Si(1)—C(51)—C(54) | −52.7 (2) |
| C(50)—Si(1)—C(51)—C(54) | 67.2 (2) |
| C(49)—Si(1)—C(51)—C(54) | −172.1 (2) |
| O(2)—Si(1)—C(51)—C(52) | 67.5 (3) |
| C(50)—Si(1)—C(51)—C(52) | −172.7 (2) |
| C(49)—Si(1)—C(51)—C(52) | −51.9 (2) |
| C(1S)—C(2S)—C(3S)—C(4S) | −178.9 (3) |
| C(2S)—C(3S)—C(4S)—C(5S) | 174.5 (3) |
| C(6S)—C(7S)—C(8S)—C(9S) | −179.7 (3) |
| C(7S)—C(8S)—C(9S)—C(10S) | 176.5 (4) |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A composition, comprising: a metal complex comprising a stereogenic metal atom and two or more ligands, wherein each ligand associated with the metal complex comprises an organic group and binds the stereogenic metal atom via one site of the ligand, wherein the composition comprises the metal complex in a diastereomeric ratio greater than 1:1;
wherein the metal complex has the structure,

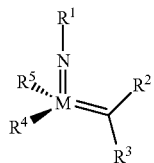

wherein:
M is Mo or W;
R$^1$ is aryl or alkyl, optionally substituted with one or more of R$^5$;
R$^2$ is hydrogen, alkyl, or aryl, optionally substituted;
R$^3$ is alkyl, optionally substituted;
R$^4$ is a chiral biaryl group, optionally substituted; and
R$^5$ is alkyl, heteroalkyl, aryl, heteroaryl, halogen, or a silyl group, optionally substituted; wherein the chiral biaryl group is

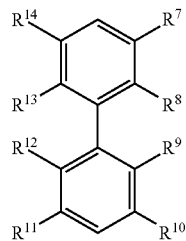

wherein R$^7$ is aryl, heteroaryl, alkyl, or heteroalkyl, optionally substituted;
R$^8$ is —OP;
R$^9$ is —OH;
R$^{10}$ is hydrogen, halogen, alkyl, heteroalkyl, aryl, heteroaryl, or acyl, optionally substituted;
each R$^{11}$, R$^{12}$, R$^{13}$, and R$^{14}$ can be the same or different and is aryl, heteroaryl, alkyl, heteroalkyl, or acyl, optionally substituted; or,
together R$^{11}$ and R$^{12}$ are joined to form a ring, optionally substituted; or
together R$^{13}$ and R$^{14}$ are joined to form a ring, optionally substituted; and
P is a protecting group;
wherein R$^4$ coordinates the metal atom M via the hydroxyl group R$^9$ of the chiral biaryl group, and
wherein the hydroxyl group is deprotonated upon coordination to the metal center.

2. A composition, comprising: a metal complex comprising a stereogenic metal atom and two or more ligands, wherein each ligand associated with the metal complex comprises an organic group and binds the stereogenic metal atom via one site of the ligand, wherein the composition comprises the metal complex in a diastereomeric ratio greater than 1:1;
wherein the metal complex has the structure,

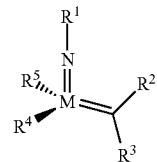

wherein:
M is Mo or W;
R$^1$ is aryl or alkyl, optionally substituted with one or more of R$^5$;
R$^2$ is hydrogen, alkyl, or aryl, optionally substituted;
R$^3$ is alkyl, optionally substituted;
R$^4$ is a chiral biaryl group, optionally substituted; and
R$^5$ is alkyl, heteroalkyl, aryl, heteroaryl, halogen, or a silyl group, optionally substituted; wherein the chiral biaryl group is a hydroxyl-containing chiral biaryl group and is selected from

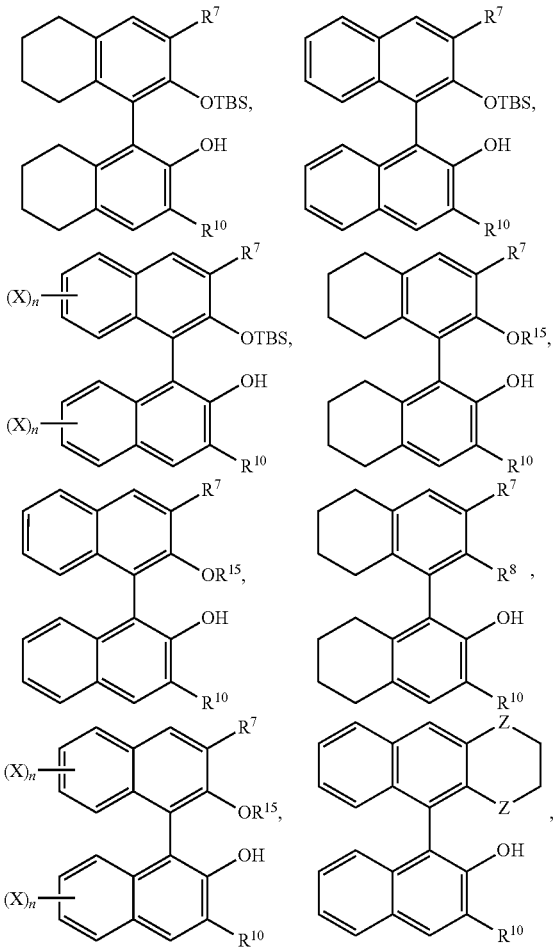

-continued

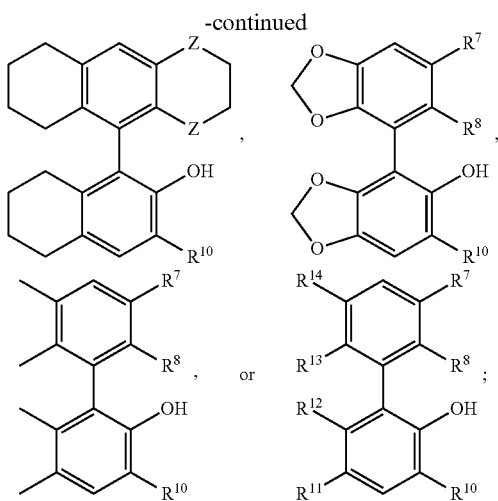

wherein each $R^7$ and $R^8$ can be the same or different and is hydrogen, halogen, alkyl, alkoxy, aryl, $CF_3$, —OSi-tri-alkyl, —OSi-tri-aryl, —OSi-alkyl-diphenyl, —OSi-phenyl-dialkyl, or acyl;

$R^{10}$ is hydrogen, halogen, alkyl, heteroalkyl, aryl, heteroaryl, or acyl, optionally substituted;

each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted;

$R^{15}$ is alkyl, aryl, —Si-trialkyl, —Si-triaryl, —Si-alkyl-diphenyl, —Si-phenyldialkyl, or acyl;

X can be methyl, ethyl or a protecting group;

each Z can be the same or different and is $(CH_2)_m$, N, O, optionally substituted;

n is 0-5; and m is 1-4;

wherein said hydroxyl group of the chiral biaryl group coordinates the metal atom M, and wherein the hydroxyl group is deprotonated upon coordination to the metal center.

3. The composition of claim 1, wherein $R^1$ is

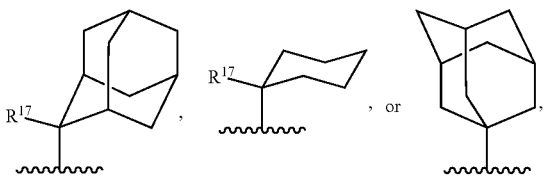

wherein each $R^{17}$ can be the same or different and is hydrogen, halogen, alkyl, heteroalkyl, aryl, acyl, or —OP, optionally substituted;

and P is a protecting group.

4. The composition of claim 1, wherein $R^1$ is

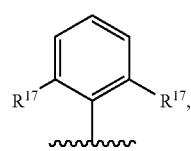

wherein each $R^{17}$ can be the same or different and is hydrogen, halogen, alkyl, heteroalkyl, aryl, acyl, or —OP, optionally substituted; and P is a protecting group.

5. The composition of claim 1, wherein $R^5$ is

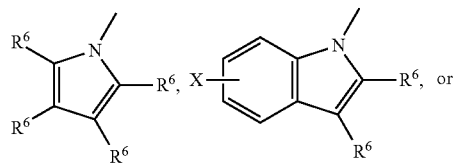

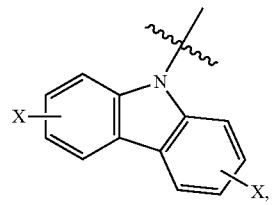

wherein each $R^6$ can be the same or different and is hydrogen, alkyl, heteroalkyl, aryl, heteroaryl, and X may be present or absent and is methyl, ethyl or a protecting group.

6. A composition, comprising:

a metal complex comprising a stereogenic metal atom and two or more ligands, wherein each ligand associated with the metal complex comprises an organic group and binds the stereogenic metal atom via one site of the ligand, wherein the composition comprises the metal complex in a diastereomeric ratio greater than 1:1;

wherein the metal complex has the structure,

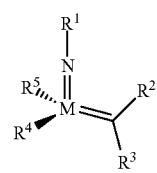

wherein

M is Mo or W;

$R^1$ is

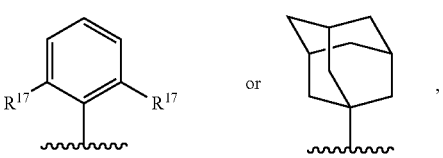

$R^{17}$ can be the same or different and is hydrogen, halogen, alkyl, heteroalkyl, aryl, acyl, or —OP, optionally substituted;

$R^2$ is $CMe_2Ph$ or $CMe_3$;
$R^3$ is hydrogen;
$R^4$ is an enantiomer of the following structure,

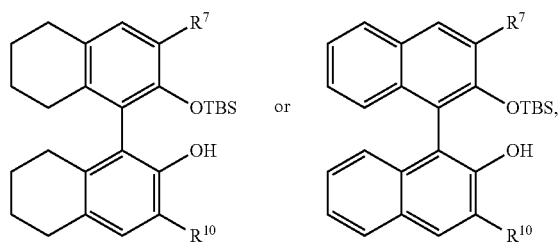

wherein each $R^7$ and $R^{10}$ is the same or different and is halogen, methyl, t-butyl, $CF_3$, or aryl, optionally substituted; and TBS is tert-butyldimethylsilyl;
wherein said hydroxyl group of said enantiomer $R^4$ coordinates the metal atom M, and wherein the hydroxyl group is deprotonated upon coordination to the metal center;
$R^5$ is

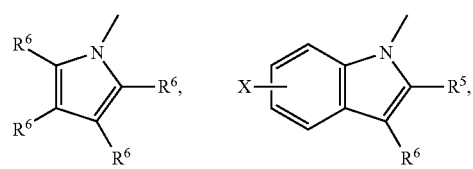

wherein $R^6$ can be the same or different and is hydrogen, alkyl, heteroalkyl, aryl, heteroaryl, and X may be present or absent and is methyl, ethyl or a protecting group.

7. The composition of claim 6, wherein:
M=Mo
$R^7$=$R^{10}$ selected from halogen, methyl
$R^5$=

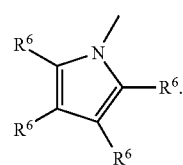

8. The composition of claim 6, wherein the metal complex has the structure,

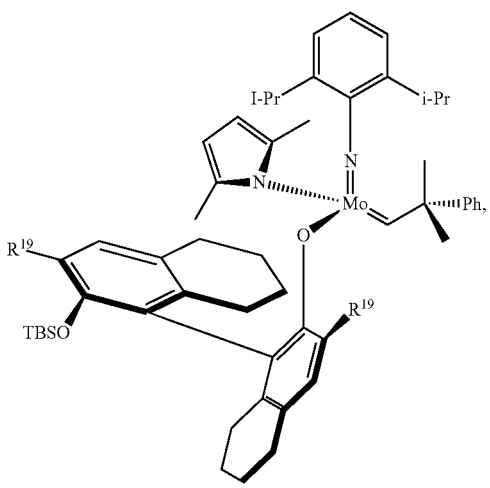

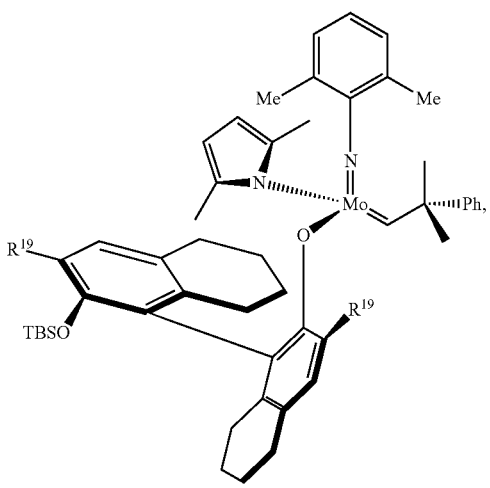

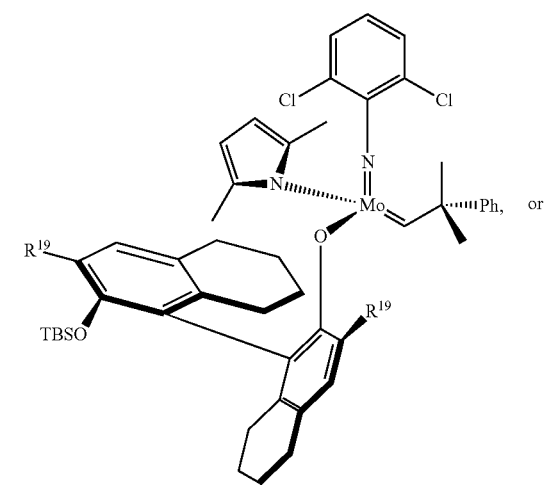

-continued

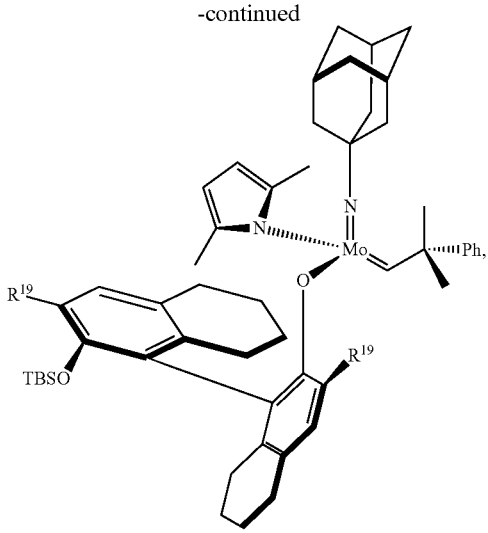

wherein R¹⁹ is F, Cl, Br, or I.

9. The composition of claim 2, wherein $R^7$ and $R^{10}$ are the same or different and are selected from the group consisting of F, Cl, Br, or I.

10. The composition of claim 1, wherein M is Mo.

11. The composition of claim 2, wherein $R^1$ is

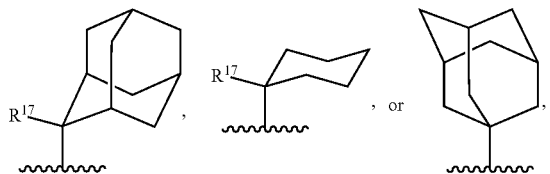

wherein each $R^{17}$ can be the same or different and is hydrogen, halogen, alkyl, heteroalkyl, aryl, acyl, or —OP, optionally substituted; and P is a protecting group.

12. The composition of claim 2, wherein $R^1$ is

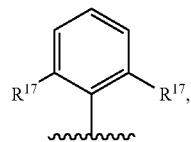

wherein each $R^{17}$ can be the same or different and is hydrogen, halogen, alkyl, heteroalkyl, aryl, acyl, or —OP, optionally substituted; and
P is a protecting group.

13. The composition of claim 2, wherein $R^5$ is

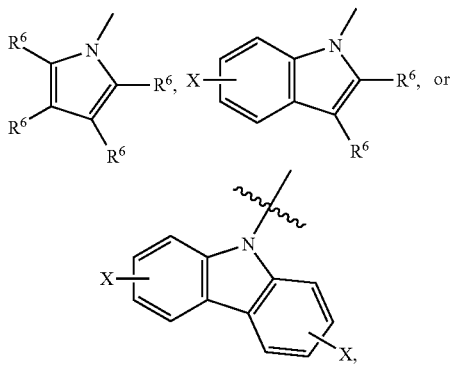

wherein each $R^6$ can be the same or different and is hydrogen, alkyl, heteroalkyl, aryl, heteroaryl, and X may be present or absent and is methyl, ethyl or a protecting group.

14. The composition of claim 6, wherein $R^7$ and $R^{10}$ are the same or different and are selected from the group consisting of F, Cl, Br, or I.

15. The composition of claim 2, wherein M is Mo.

16. The composition of claim 6, wherein M is Mo.

* * * * *

UNITED STATES PATENT AND TRADEMARK OFFICE
CERTIFICATE OF CORRECTION

PATENT NO. : 9,687,834 B2  
APPLICATION NO. : 12/864261  
DATED : June 27, 2017  
INVENTOR(S) : Steven J. Malcolmson et al.

Page 1 of 2

It is certified that error appears in the above-identified patent and that said Letters Patent is hereby corrected as shown below:

Column 12, Line 34 reads, ". . . to wherein each $R^{17}$ can be the same or different . . ." which should read, ". . . wherein each $R^{17}$ can be the same or different . . ."

Column 30, Line 17 reads, ". . . <2% cony, even at . . ." which should read, ". . . <2% conv, even at. . ."

Column 36, Line 57 reads, ". . . 96% cony,. . ." which should read, ". . . 96% conv,. . ."

Column 36, Line 62 reads, ". . . 95% cony,. . ." which should read, ". . . 95% conv,. . ."

Column 37, Line 55 reads, ". . . cony) in 92% e.e.; in 10 min only 70% cony. . ." which should read, ". . . conv) in 92% e.e.; in 10 min only 70% conv. . ."

Column 37, Line 62 reads, ". . . >98% cony, . . ." which should read, ". . . >98% conv,. . ."

Column 37, Line 65 reads, ". . . >98% cony) . . ." which should read, ". . . >98% conv). . ."

Column 38, Line 48 reads, ". . . >98% cony) . . ." which should read, ". . . >98% conv). . ."

Column 38, Line 50 reads, ". . . >98% cony) . . ." which should read, ". . . >98% conv). . ."

Column 38, Line 59 reads, ". . . >98% cony, . . ." which should read, ". . . >98% conv, . . ."

Column 38, Line 66 reads, ". . . 75% cony, . . ." which should read, ". . . 75% conv,. . ."

Column 38, Line 67 reads, ". . . >98% cony, . . ." which should read, ". . . >98% conv, . . ."

Column 40, Line 5 reads, ". . . 91% cony, . . ." which should read, ". . . 91% conv, . . ."

Column 41, Line 27 reads, ". . . >98% cony, . . ." which should read, ". . . >98% conv, . . ."

Signed and Sealed this  
Seventeenth Day of July, 2018

Andrei Iancu  
*Director of the United States Patent and Trademark Office*

CERTIFICATE OF CORRECTION (continued)
U.S. Pat. No. 9,687,834 B2

Column 42, Line 24 reads, "... >98% cony, ..." which should read, "... >98% conv, ..."

Column 42, Line 30 reads, "... (91% cony, ..." which should read, "... (91% conv, ..."

Column 48, Line 66 reads, "... 21% cony to 70a ..." which should read, "... 21% conv to 70a ..."

Column 57, Line 37 reads, "... 2.47. found: ..." which should read, "... 2.47; found: ..."

Column 62, Line 18 reads, "... $CDCl_3$ ..." which should read, "... $CHCl_3$ ..."

Column 83, Line 39 reads, "... wherein said hydroxyl croup of the chiral biaryl croup ..." which should read, "... wherein said hydroxyl group of the chiral biaryl group ..."